(12) United States Patent
Fairhurst et al.

(10) Patent No.: US 8,476,268 B2
(45) Date of Patent: *Jul. 2, 2013

(54) PYRROLIDINE-1,2-DICARBOXAMIDE DERIVATIVES

(75) Inventors: Robin Alec Fairhurst, Riehen (CH); Vito Guagnano, Basel (CH); Patricia Imbach-Weese, Kaiseraugst (CH); Giorgio Caravatti, Bottmingen (CH); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/488,589

(22) Filed: Jun. 5, 2012

(65) Prior Publication Data

US 2012/0263712 A1    Oct. 18, 2012

Related U.S. Application Data

(63) Continuation of application No. 12/556,964, filed on Sep. 10, 2009, now Pat. No. 8,227,462.

(60) Provisional application No. 61/096,674, filed on Sep. 12, 2008.

(30) Foreign Application Priority Data

Sep. 10, 2008  (EP) ..................................... 08164104

(51) Int. Cl.
  *C07D 417/14*  (2006.01)
  *A61K 31/4439*  (2006.01)

(52) U.S. Cl.
  USPC ........ 514/235.8; 514/256; 514/275; 544/122; 544/331; 544/332; 544/333

(58) Field of Classification Search
  USPC ............... 544/122, 331, 332, 333; 514/235.8, 514/256, 275
  See application file for complete search history.

(56) References Cited

U.S. PATENT DOCUMENTS

| | | | |
|---|---|---|---|
| 4,649,146 | A | 3/1987 | Takaya et al. |
| 4,735,957 | A | 4/1988 | Takaya et al. |
| 6,187,797 | B1 | 2/2001 | Pruitt et al. |
| 6,531,479 | B2 | 3/2003 | Wang et al. |
| 6,586,423 | B2 | 7/2003 | Bilodeau et al. |
| 7,232,838 | B2 | 6/2007 | Love et al. |
| 7,388,015 | B2 | 6/2008 | Wang et al. |
| 7,973,169 | B2 | 7/2011 | Hadida Ruah et al. |
| 8,227,462 | B2 * | 7/2012 | Fairhurst et al. ........... 514/235.8 |
| 2004/0122016 | A1 | 6/2004 | Cao et al. |
| 2007/0259855 | A1 | 11/2007 | Maier et al. |
| 2009/0036654 | A1 | 2/2009 | Jacobs et al. |
| 2009/0163469 | A1 | 6/2009 | Caravatti et al. |

FOREIGN PATENT DOCUMENTS

| | | |
|---|---|---|
| EP | 280873 A1 | 9/1988 |
| EP | 0 373 226 A1 | 6/1990 |
| EP | 1 256 578 A1 | 11/2002 |
| EP | 1 256 578 B1 | 11/2002 |
| WO | 98/27108 A2 | 6/1998 |
| WO | 99/21555 A2 | 5/1999 |
| WO | WO 99/65884 A1 | 12/1999 |
| WO | 02/32872 A1 | 4/2002 |
| WO | WO 03/015778 A1 | 2/2003 |
| WO | WO 03/072557 A1 | 9/2003 |
| WO | WO 2004/045518 A2 | 6/2004 |
| WO | WO 2004/078754 A1 | 9/2004 |
| WO | WO 2004/096797 A1 | 11/2004 |
| WO | WO 2005/021519 A2 | 3/2005 |
| WO | WO 2005/026137 A2 | 3/2005 |
| WO | WO 2005/068444 A2 | 7/2005 |
| WO | WO 2006/051270 A1 | 5/2006 |
| WO | WO 2006/125805 A1 | 11/2006 |
| WO | WO 2006/125807 A1 | 11/2006 |
| WO | WO 2007/033780 A2 | 3/2007 |
| WO | WO 2007/068473 A2 | 6/2007 |
| WO | WO 2007/070600 A2 | 6/2007 |
| WO | WO 2007/082956 A1 | 7/2007 |
| WO | 2007/129044 A1 | 11/2007 |
| WO | WO 2007/134827 A1 | 11/2007 |
| WO | 2008/000421 A2 | 1/2008 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*
Berge et al.; "Pharmaceutical Salts"; Journal of Pharmaceutical Sciences—Review Article; 66(1):1-19 (1977).
CA 106:67261; Kulkarni et al.; Indian Journal of Chemistry, Section B: Organic Chemistry Including Medicinal Chemistry; 25B(4):452-455 (1986).
CAPLUS 1986:439172; Reddy et al.; Indian Botanical Reporter; 4(2):144-147 (1985).
Fry; "Phosphoinositide 3-kinase signalling in breast cancer: how big a role might it play?"; Breast Cancer Res; 3:304-312 (2001).

(Continued)

*Primary Examiner* — Deepak Rao
(74) *Attorney, Agent, or Firm* — Scott W. Reid

(57) ABSTRACT

The present invention relates to a compound of formula (I)

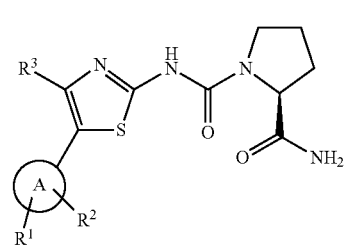

or a salt thereof, wherein the substituents are as defined in the description, to compositions and use of the compounds in the treatment of diseases ameliorated by inhibition of phosphatidylinositol 3-kinase.

5 Claims, No Drawings

FOREIGN PATENT DOCUMENTS

| WO | WO 2008/064218 A2 | 5/2008 |
|---|---|---|
| WO | WO 2008/124000 A2 | 10/2008 |
| WO | WO 2008/145616 A1 | 12/2008 |
| WO | WO 2009/003009 A1 | 12/2008 |
| WO | WO 2009/012482 A2 | 1/2009 |
| WO | WO 2009/080694 A1 | 7/2009 |
| WO | WO 2009/080705 A2 | 7/2009 |

OTHER PUBLICATIONS

Kulkarni et al.; "Reactions of o-Aminothiophenol, Guanidine, Thiourea, Hydrazine Hydrate & Hydroxylamine with Acryloylthiazoles & Microbial Activities of the Reaction Products"; Indian Journal of Chemistry; 25B:452-455 (1986).

Luo et al.; "Principles of Cancer Therapy: Oncogene and Non-oncogene Addiction"; Cell—Leading Edge Review; 136:823-837 (2009).

Simone; "Oncology: Introduction"; Cecil Textbook of Medicine; 20th Edition—vol. 1; pp. 1004-1010 (1996).

Simone, Oncology: Introduction, Cecil Textbook of Medicine, 20th Edition, vol. 1, pp. 1004-1010, 1996.

Fry et al., Phosphoinositide 3-Kinase signalling in breast cancer: how big a role might it play?, Breat Cancer Res, 3:304-312, 2001.

Luo et al., Principles of Cancer Therapy, Cell 136, Mar. 6, 2009, pp. 823-837.

Gura, Systems for identifying New Drugs Are Often Faulty, Cancer Models, Science, vol. 278, No. 5340, pp. 1041-1042, Nov. 1997.

Johnson et al., Relationships between drug activity in NCI preclinical in vitro and in vivo models and early clinical trials, British Journal of Cancer (2001) 64(10):1424-1431.

* cited by examiner

PYRROLIDINE-1,2-DICARBOXAMIDE DERIVATIVES

This application is a Continuation of U.S. Utility application Ser. No. 12/556,964 filed 10 Sep. 2009, which claims priority to U.S. Provisional Application Ser. No. 61/096,674 filed 12 Sep. 2008, and to EP Application Serial No. 08164104.5 filed 10 Sep. 2008, the contents of which are incorporated herein by reference in their entirety.

The present invention relates to specific 2-carboxamide cycloamino urea derivatives, as new, alpha-selective phosphatidylinositol (PI) 3-kinase inhibitor compounds, their pharmaceutically acceptable salts, prodrugs thereof and processes for their production. This invention also relates to compositions of these compounds, either alone or in combination with at least one additional therapeutic agent, and optionally in combination with a pharmaceutically acceptable carrier. This invention still further relates to methods of use of these compounds, either alone or in combination with at least one additional therapeutic agent, in the treatment of a number of diseases, in particular, those mediated by one or more of abnormal activity of growth factors, receptor tyrosine kinases, protein serine/heroine kinases, G protein coupled receptors and phospholipid kinases and phosphatases.

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem.* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit ($\alpha$, $\beta$, $\delta$ isoforms) constitutively associated with a regulatory subunit that can be p85$\alpha$, p55$\alpha$, p50$\alpha$, p85$\beta$ or p55$\gamma$. The Class 1B sub-class has one family member, a heterodimer composed of a catalytic p110$\gamma$ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Aid, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Aid activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110$\alpha$ isoform, PIK3CA, and for Akt are amplified and increased protein expression of their gene products has been demonstrated in several human cancers. Furthermore, mutations and translocation of p85$\alpha$ that serve to up-regulate the p85-p110 complex have been described in human cancers. Finally, somatic missense mutations in PIK3CA that activate downstream signaling pathways have been described at significant frequencies in a wide diversity of human cancers (Kang et al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey et al., *Nature Rev. Drug Disc.* 4:988-1004 (2005)).

In view of the above, inhibitors of PI3K alpha would be of particular value in the treatment of proliferative disease and other disorders.

WO2004/096797 discloses certain thiazole derivatives as inhibitors of PI3K gamma and their pharmaceutical use, particularly for the treatment of inflammatory and allergic conditions.

WO 2005/021519 also discloses certain thiazole derivatives as inhibitors of PI3K gamma and their pharmaceutical use, particularly for the treatment of inflammatory and allergic conditions.

WO 2006/051270 also discloses certain thiazole derivatives as inhibitors of PI3K alpha and their pharmaceutical use, particularly due to anti-tumor activity.

WO 2007/129044 also discloses certain thiazole derivatives as inhibitors of PI3K alpha and their pharmaceutical use, particularly due to anti-tumor activity.

In view of the prior art, there is a need to provide further compounds suitable for treatment of proliferative diseases, particularly to provide compounds having improved selectivity and/or higher/improved activity.

It has now been found that the 2-carboxamide cycloamino urea derivatives of the formula (I) given below have advantageous pharmacological properties and inhibit, for example, PI3K (phosphatidylinositol 3-kinase). In particular, these compounds preferably show an improved selectivity for PI3K alpha with respect to beta and/or, delta and/or gamma subtypes. Hence, the compounds of formula I are suitable, for example, to be used in the treatment of diseases depending on PI3 kinases (in particular PI3K alpha, such as those showing overexpression or amplification of PI3K alpha, somatic mutation of PIK3CA or germline mutations or somatic mutation of PTEN or mutations and translocation of p85 cc that serve to up-regulate the p85-p110 complex), especially proliferative diseases such as tumor diseases and leukaemias. Further, these compounds preferably show improved metabolic stability and hence reduced clearance, leading to improved pharmacokinetic profiles.

In a first aspect, the present invention provides compounds of the formula (I)

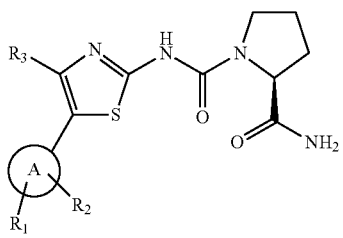

or a salt thereof, wherein
A represents heteroaryl;
$R^1$ represents (1) optionally substituted alkyl; (2) optionally substituted cycloalkyl; (3) optionally substituted aryl; (4) optionally substituted amine; (5) optionally substituted sulfonyl; (6) halo;
$R^2$ represents hydrogen, deuterium or a substituent as defined for $R^1$;
$R^3$ represents hydrogen, halo, optionally substituted alkyl; with the exception of (S)-Pyrrolidine-1,2-dicarboxylic acid 2-amide 1-({5-[2-(tert-butyl)-pyrimidin-4-yl]-4-methyl-thiazol-2-yl}-amide).

The invention may be more fully appreciated by reference to the following description, including the following glossary of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula (I), such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers.

Any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (haloalkyl) can be mono-, poly- or per-halogenated.

Hetero atoms are atoms other than Carbon and Hydrogen, preferably nitrogen (N), oxygen (O) or sulfur (S), in particular nitrogen.

Carbon containing groups, moieties or molecules contain 1 to 7, preferably 1 to 6, more preferably 1 to 4, most preferably 1 or 2, carbon atoms. Any non-cyclic carbon containing group or moiety with more than 1 carbon atom is straight-chain or branched.

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to deuterium, hydroxy, alkoxy, halo and amino. An example of a substituted alkyl is trifluoromethyl. Cycloalkyl may also be a substituent to alkyl. An example of such a case is the moiety (alkyl)-cyclopropyl or alkandiyl-cyclopropyl, e.g. —CH$_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl".

"Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—CH$_2$—), 1,2-ethanediyl (—CH$_2$—CH$_2$—), 1,1-ethanediyl ((—CH(CH$_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

"Alkendiyl" refers to a straight-chain or branched-chain alkendiyl group bound by two different Carbon atoms to the molecule, it preferably represents a straight-chain or branched-chain $C_{2-6}$ alkandiyl; for example, —CH=CH—, —CH=C(CH$_3$)—, —CH=CH—CH$_2$—, —C(CH$_3$)=CH—CH$_2$—, —CH=C(CH$_3$)—CH$_2$—, —CH=CH—C(CH$_3$)H—, —CH=CH—CH=CH—, —C(CH$_3$)=CH—CH=CH—, —CH=C(CH$_3$)—CH=CH—, with particular preference given to —CH=CH—CH$_2$—, —CH=CH—CH=CH—. Alkendiyl may be substituted or unsubstituted "Cycloalkyl" refers to a saturated or partially saturated, monocyclic, fused polyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl. Cycloalkyl may be unsubstituted or substituted; exemplary substituents are provided in the definition for alkyl and also include alkyl itself (e.g. methyl). A moiety like —(CH$_3$) cyclopropyl is considered substituted cycloalkyl.

"Aryl" refers to an aromatic homocyclic ring system (i.e. only Carbon as ring forming atoms) with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxopyrrolidino, $C_1$-$C_7$-alkyl-pyrrolidinyl, 2,5-di-($C_1$-$C_7$alkyl)pyrrolidinyl, such as 2,5-di-($C_1$-$C_7$-alkyl)-pyrrolidino, tetrahydrofuranyl, thiophenyl, $C_1$-$C_7$-alkylpyrazolidinyl, pyridinyl, $C_1$-$C_7$-alkylpiperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thio-morpholino, S-oxo-thiomorpholino or S,S-dioxothiomorpholino; $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halo-lower alkylmercapto, sulfo (—SO$_3$H), lower alkanesulfonyl, phenyl- or naphthyl-sulfonyl, phenyl- or naphthyl-lower alkylsulfonyl, alkylphenylsulfonyl, halo-lower alkylsulfonyl, such as trifluoromethanesulfonyl; sulfonamido, benzosulfonamido, azido, azido-$C_1$-$C_7$-alkyl, especially azidomethyl, $C_1$-$C_7$-alkanesulfonyl, sulfamoyl, N-mono- or N,N-di-($C_1$-$C_7$-alkyl)-sulfannoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxycarbonyl, carbamoyl, cyano and/or sulfamoyl.

"Heterocyclyl" refers to a heterocyclic radical that is unsaturated (=carrying the highest possible number of conjugated double bonds in the ring(s)), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl also includes heteroaryl. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (=O), thiocarbonyl (=S), imino(=NH), imino-lower alkyl. Further, heterocyclyl is especially a heterocyclyl radical selected from the group consisting of oxiranyl, aziridinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydro-benzo[1,4]dioxin-6-yl, each of these radicals being unsubstituted or substituted by one or more, preferably up to three, substituents selected from those mentioned above for substituted aryl and/or from one or more of the following substituents: oxo (=O), thiocarbonyl (=S), imino(=NH), imino-lower alkyl.

"Arylalkyl" refers to an aryl group bound to the molecule via an alkyl group, such as a methyl or ethyl group, preferably phenethyl or benzyl, in particular benzyl. Similarly, cycloalkyl-alkyl and heterocyclyl-alkyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Treatment" includes prophylactic (preventive) and therapeutic treatment as well as the delay of progression of a disease or disorder.

"PI3 kinase mediated diseases" (especially PI3K alpha mediated diseases or diseases mediated by overexpression or amplification of PI3K alpha, somatic mutation of PIK3CA or germline mutations or somatic mutation of PTEN or mutations and translocation of p85α that serve to up-regulate the p85-p110 complex), are especially such disorders that respond in a beneficial way (e.g. amelioration of one or more symptoms, delay of the onset of a disease, up to temporary or complete cure from a disease) to the inhibition of a PI3 kinase, especially inhibition of PI3Kalpha or a mutant form thereof (where among the diseases to be treated, proliferative diseases such as tumor diseases and leukaemias may be especially mentioned).

"Salts" (which, what is meant by "or salts thereof" or "or a salt thereof"), can be present alone or in mixture with free compound of the formula (I) and are preferably pharmaceutically acceptable salts. Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of compounds of formula (I) are preferably pharmaceutically acceptable salts; suitable counter-ions forming pharmaceutically acceptable salts are known in the field.

"Combination" refers to either a fixed combination in one dosage unit form, or a kit of parts for the combined administration where a compound of the formula (I) and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula (I), in free base form or in acid addition salt form, wherein the substituents are as defined herein.

In an advantageous embodiment, the invention relates to a compound of formula IA

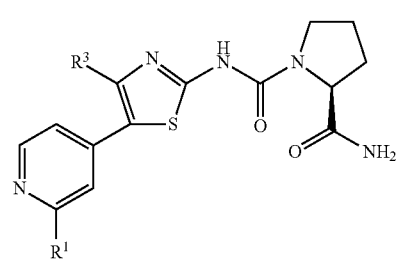

IA wherein the substituents are as defined for a compound of formula (I).

In a further advantageous embodiment, the invention relates to a compound of formula IB

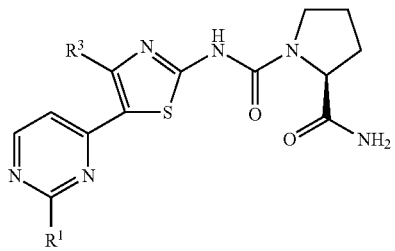
IB wherein the substituents are as defined for a compound of formula (I).

Thus, a compound of formula (I) also includes compounds of formula (IA) and (IB). In the context of this invention, the following definitions are also applicable.

A preferably represents heteroaryl with one or two nitrogen atoms and 5 to 10 ring forming atoms.

A particularly preferably represents a heteroaryl selected from the group consisting of:

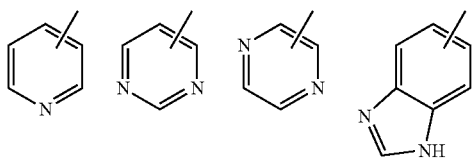

A very particularly preferably represents a heteroaryl selected from the group consisting of:

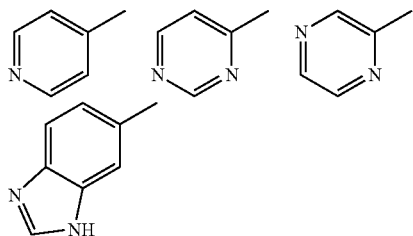

A most preferably represents a heteroaryl selected from the group consisting of:

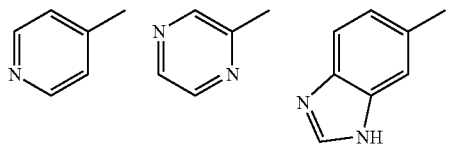

$R^1$ preferably represents one of the following substituents:
(1) unsubstituted or substituted, preferably substituted $C_1$-$C_7$-alkyl, wherein said substituents are independently selected from one or more, preferably one to nine of the following moieties: deuterium, halo, cyano, $C_3$-$C_{12}$-cycloalkyl, $C_1$-$C_7$-alkylamino, di($C_1$-$C_7$-alkyl)amino, $C_1$-$C_7$-alkylaminocarbonyl, di($C_1$-$C_7$-alkyl)aminocarbonyl, $C_1$-$C_7$-alkoxy, phenyl (which is unsubstituted or substituted by one or more, preferably one $C_1$-$C_7$-alkyl, $C_1$-$C_7$-alkoxy, di($C_1$-$C_7$-alkyl)amino-$C_1$-$C_7$-alkoxy), phenoxy, (which is unsubstituted or substituted by one or more, preferably one $C_1$-$C_7$-alkyl, $C_1$-$C_7$-alkoxy, di($C_1$-$C_7$-alkyl)amino-$C_1$-$C_7$-alkoxy);
(2) unsubstituted or substituted $C_3$-$C_{12}$-cycloalkyl wherein said substituents are independently selected from one or more, preferably one to four of the following moieties: deuterium, halo, cyano, $C_1$-$C_7$-alkyl, $C_1$-$C_7$-alkylamino, di($C_1$-$C_7$-alkyl)amino, aminocarbonyl, $C_1$-$C_7$-alkylaminocarbonyl, di($C_1$-$C_7$-alkyl)aminocarbonyl, $C_1$-$C_7$-alkoxy, phenyl (which is unsubstituted or substituted by one or more, preferably one $C_1$-$C_7$-alkyl, $C_1$-$C_7$-alkoxy, di($C_1$-$C_7$-alkyl)amino-$C_1$-$C_7$-alkoxy), phenoxy, (which is unsubstituted or substituted by one or more, preferably one $C_1$-$C_7$-alkyl, $C_1$-$C_7$-alkoxy, di($C_1$-$C_7$-alkyl)amino-$C_1$-$C_7$-alkoxy);
(3) unsubstituted or substituted phenyl wherein said substituents are independently selected from one or more, preferably one to two of the following moieties: deuterium, halo, cyano, $C_1$-$C_7$-alkyl, $C_1$-$C_7$-alkylamino, $C_1$-$C_7$-alkylaminocarbonyl, di($C_1$-$C_7$-alkyl)aminocarbonyl, $C_1$-$C_7$-alkoxy;
(4) unsubstituted, mono- or di-substituted amine; wherein said substituents are independently selected from the following moieties: deuterium, $C_1$-$C_7$-alkyl (which is unsubstituted or substituted by one or more substituents selected from the group of deuterium, fluoro, chloro, hydroxy), $C_1$-$C_7$-alkylcarbonyl, phenyl (which is unsubstituted or substituted by one or more, preferably one, $C_1$-$C_7$-alkyl, $C_1$-$C_7$-alkoxy, di($C_1$-$C_7$-alkyl)amino-$C_1$-$C_7$-alkoxy), phenylsulfonyl (which is unsubstituted or substituted by one or more, preferably one, $C_1$-$C_7$-alkyl, $C_1$-$C_7$-alkoxy, di($C_1$-$C_7$-alkyl)amino-$C_1$-$C_7$-alkoxy),
(5) substituted sulfonyl; wherein said substituent is selected from the following moieties: $C_1$-$C_7$-alkyl (which is unsubstituted or substituted by one or more substituents selected from the group of deuterium, fluoro, chloro, hydroxy), $C_1$-$C_7$-alkylamino (wherein the alkyl part is unsubstituted or substituted by one or more substituents selected from the group of deuterium, fluoro, chloro, hydroxyl) di-$C_1$-$C_7$-alkylamino (wherein the alkyl part is unsubstituted or substituted by one or more substituents selected from the group of deuterium, fluoro, chloro, hydroxyl);
(6) fluoro, chloro.

$R^1$ particularly preferably represents one of the following substituents:
(1) unsubstituted or substituted, preferably substituted $C_1$-$C_7$-alkyl, wherein said substituents are independently selected from one or more, preferably one to nine of the following moieties: deuterium, fluoro, or one to two of the following moieties: $C_3$-$C_5$-cycloalkyl;
(2) optionally substituted $C_3$-$C_5$-cycloalkyl wherein said substituents are independently selected from one or more, preferably one to four of the following moieties: deuterium, $C_1$-$C_4$-alkyl (preferably methyl), fluoro, cyano, aminocarbonyl;
(3) optionally substituted phenyl wherein said substituents are independently selected from one or more, preferably one to two of the following moieties: deuterium, halo, cyano, $C_1$-$C_7$-alkylamino, di($C_1$-$C_7$-alkyl)amino, $C_1$-$C_7$-alkylaminocarbonyl, di($C_1$-$C_7$-alkyl)aminocarbonyl, $C_1$-$C_7$-alkoxy;
(4) optionally mono- or di-substituted amine; wherein said substituents are independently selected from the following moieties: deuterium, $C_1$-$C_7$-alkyl (which is unsubstituted or substituted by one or more substituents selected from the group of deuterium, fluoro, chloro, hydroxy), phenylsulfonyl (which is unsubstituted or substituted by one or more, preferably one, $C_1$-$C_7$-alkyl, $C_1$-$C_7$-alkoxy, di($C_1$-$C_7$-alkyl)amino-$C_1$-$C_7$-alkoxy), (5) substituted sulfonyl; wherein said substituent is selected from the following moieties: $C_1$-$C_7$-alkyl (which is unsubstituted or substituted by one or more substituents selected from the group of deuterium, fluoro), pyrrolidino, (which is unsubstituted or substituted by one or more substituents selected from the group of deuterium, hydroxy, oxo; particularly one oxo), (6) fluoro, chloro.

$R^1$ very particularly preferably represents:

(1) cyclopropylmethyl or optionally substituted, branched $C_3$-$C_7$-alkyl, wherein said substituents are independently selected from one or more, preferably one to nine of the following moieties: deuterium, fluoro;

(2) optionally substituted cyclopropyl or cyclobutyl wherein said substituents are independently selected from one or more, preferably one to four of the following moieties: methyl, deuterium, fluoro, cyano, aminocarbonyl;

(3) optionally substituted phenyl wherein said substituents are independently selected from one or more, preferably one to two of the following moieties: deuterium, halo, cyano, $C_1$-$C_7$-alkylamino, di($C_1$-$C_7$-alkyl)amino, $C_1$-$C_7$-alkylaminocarbonyl, di($C_1$-$C_7$-alkyl)aminocarbonyl, $C_1$-$C_7$-alkoxy;

(4) optionally mono- or di-substituted amine; wherein said substituents are independently selected from the following moieties: deuterium, $C_1$-$C_7$-alkyl (which is unsubstituted or substituted by one or more substituents selected from the group of deuterium, fluoro, chloro, hydroxy), phenylsulfonyl (which is unsubstituted or substituted by one or more, preferably one, $C_1$-$C_7$-alkyl, $C_1$-$C_7$-alkoxy, di($C_1$-$C_7$-alkyl)amino-$C_1$-$C_7$-alkoxy), (5) substituted sulfonyl; wherein said substituent is selected from the following moieties: $C_1$-$C_7$-alkyl (which is unsubstituted or substituted by one or more substituents selected from the group of deuterium, fluoro), pyrrolidino, (which is unsubstituted or substituted by one or more substituents selected from the group of deuterium, hydroxy, oxo; particularly one oxo), (6) fluoro, chloro.

$R^1$ very particularly preferably represents, one of the following substituents: —C(CH$_3$)$_2$CF$_3$, C(CD$_3$)$_3$, 1-methylcyclopropyl; preferably in the context of (I-A) and (I-B).

$R^2$ preferably represents a substituent as defined for $R^1$.

$R^2$ further preferably represents hydrogen or deuterium.

$R^2$ particularly preferably represents hydrogen.

$R^2$ in an alternative embodiment represents methyl.

$R^3$ preferably represents (1) hydrogen, (2) halo, (3) optionally substituted $C_1$-$C_7$-alkyl, wherein said substituents are independently selected from one or more, preferably one to three of the following moieties: deuterium, halo, $C_1$-$C_7$-alkylamino, di($C_1$-$C_7$-alkyl)amino.

$R^3$ particularly preferably represents (1) hydrogen, (2) fluoro, chloro, (3) optionally substituted methyl, wherein said substituents are independently selected from one or more, preferably one to three of the following moieties: deuterium, fluoro, chloro, dimethylamino.

$R^3$ very particularly preferably represents hydrogen, methyl, CD$_3$, CH$_2$Cl, CH$_2$F, CH$_2$N(CH$_3$)$_2$; preferably methyl.

The invention further relates to a compound of formula (I) as defined herein with the exception of such compounds where $R^1$ and/or $R^2$ represents tert-butyl.

The invention further relates to pharmaceutically acceptable prodrugs of a compound of formula (I).

The invention further relates to pharmaceutically acceptable metabolites of a compound of formula (I).

The invention relates especially to the compounds of the formula (I) given in the Examples, as well as the methods of manufacture described therein.

The present invention also relates to processes for the production of a compound of formula (I). In principle all known processes which convert two different amines into a corresponding urea derivative are suitable and may be applied by using the respective starting material.

Thus, the invention in particular relates to a process for manufacturing a compound of formula (I), which comprises reacting a compound of formula (II)

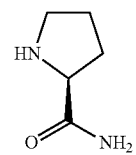

(II)

either with a compound of formula (IIIA)

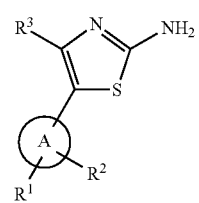

(IIIA)

wherein the substituents are as defined herein and $R^3$ may additionally represent Chloro, in the presence of an activating agent ("method A"), or with a compound of formula (IIIB)

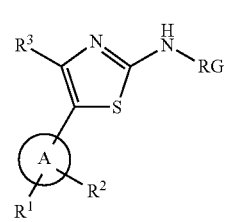

(IIIB)

wherein $R^1$ and $R^2$ are as defined herein, $R^3$ is as defined herein and may additionally represent Chloro and RG represents a reactive group, such as imidazolylcarbonyl, which can react directly or via the formation of the isocyanate intermediate of formula (IIIE) ("method B"),

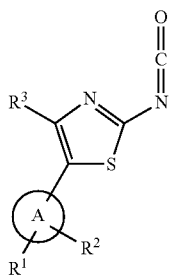

(IIIE)

wherein the substituents are as defined in (IIIB),
in each case optionally in the presence of a diluent and optionally in the presence of a reaction aid and
recovering the resulting compound of formula (I) in free form or in form of a salt and, optionally converting a compound of the formula (I) obtainable according to method A or method B into a different compound of the formula (I), and/or converting an obtainable salt of a compound of the formula (I) into a different salt thereof, and/or converting an obtainable free compound of the formula (I) into a salt thereof, and/or separating an obtainable isomer of a compound of the formula (I) from one or more different obtainable isomers of the formula I.

Reaction Conditions

The process may be performed according to methods known in the art, or as disclosed below in the Examples. For example a compound of formula II may be reacted with a compound of formula III in a solvent, e.g. dimethylformamide, in the presence of a base e.g. an organic amine, e.g. triethylamine.

Where temperatures are given hereinbefore or hereinafter, "about" has to be added, as minor deviations from the numeric values given, e.g. variations of ±10%, are tolerable.

All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates.

Reaction aids, such as acids, bases or catalysts may be added in suitable amounts, as known in the field, required by a reaction and in line with generally known procedures.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Optional Reactions and Conversions

A compound of the formula (I) may be converted into a different compound of the formula I.

In a compound of the formula (I) wherein $R^3$ represents fluoro; such compound may be obtained by converting the corresponding chlorine derivative into the fluoro compound. Such reactions are known and referred to as substitution reactions. This conversion may take place at the step of the starting material of formula (IIIA or B) or by converting a corresponding compound of formula I.

In a compound of the formula (I) wherein a substituent carries an amino or amino-$C_1$-$C_7$-alkyl substituent, the amino can be converted into acylamino, e.g. $C_1$-$C_7$-alkanoylamino or $C_1$-$C_7$-alkanesulfonylamino, by reaction with a corresponding $C_1$-$C_7$-alkanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula (I) wherein a substituent carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

Salts of a compound of formula (I) with a salt-forming group may be prepared in a manner known per se. Acid addition salts of compounds of formula (I) may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I. Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates (and are thus useful in the preparation of corresponding starting materials).

Starting Materials:

The starting materials of the formulae II and III, as well as other starting materials mentioned herein, e.g. below, can be prepared according to or in analogy to methods that are known in the art, are known in the art and/or are commercially available. Insofar as the production of the starting materials is not particularly described, the compounds are either known or may be prepared analogously to methods known in the art, e.g. in WO 05/021519 or WO04/096797, or as disclosed hereinafter. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, the substituents are preferably as defined for a compound of the formula (I).

The invention also relates to compounds of formula (IIIA) or a salt thereof

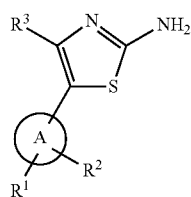

(IIIA)

wherein the substituents are as defined for a compound of formula (I).

The present invention further relates to processes for the production of a compound of formula (IIIA). In principle, all known processes which couple two aryl/heteroaryl components (such as Heck-type reactions) into a corresponding urea derivative are suitable and may be applied by using the respective starting material. The invention thus also relates to a process for preparing a compound of formula (IIIA), which comprises (Step 1) reacting a compound of formula (IV)

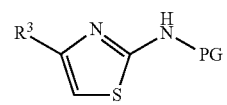

(IV)

wherein $R^3$ is as defined herein and may additionally represent halo, PG represents a protection group, such as an acyl group, with a compound of formula (V)

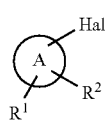

(V)

wherein $R^1$, $R^2$, A are as defined herein and Hal represents halo, such as bromo, under Heck conditions; optionally in the presence of a diluent and optionally in the presence of a reaction aid;

(Step 2) followed by removal of the protective group, e.g. under acidic conditions; optionally in the presence of a diluent and optionally in the presence of a reaction aid; and recovering the resulting compound of formula (IIIA) in free form or in form of a salt and, optionally converting a compound of the formula (IIIA) obtained into a different compound of the formula (IIIA), and/or converting an obtained salt of a compound of the formula (IIIA) into a different salt thereof, and/or converting an obtainable free compound of the formula (IIIA) into a salt thereof, and/or separating an obtainable isomer of a compound of the formula (IIIA) from one or more different obtained isomers of the formula (IIIA).

The invention further relates to compounds of formula (IIIB) or a salt thereof

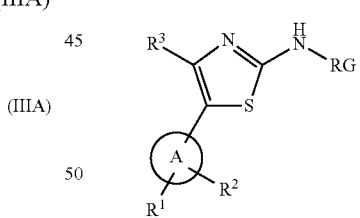

(IIIB)

wherein $R^1$, $R^2$, A are as defined for a compound of formula (I), RG represents a reactive group, particularly imidazolylcarbonyl which can react directly or via the formation of the isocyanate intermediate of formula (IIIE), and $R^3$ is as defined herein and may additionally represent halo.

The present invention further relates to processes for the production of a compound of formula (IIIB). In principle, all known processes which convert an amine or salt thereof into a corresponding activated derivative are suitable and may be applied by using the respective starting material. The invention thus also relates to a process for preparing a compound of formula (IIIB), which comprises reacting a compound of formula (IIIA)

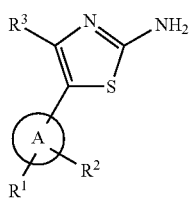

(IIIA)

wherein the substituents are as defined herein, with an activating reagent, such as 1,1'-carbonyldiimidazole, optionally in the presence of a diluent and optionally in the presence of a reaction aid; and recovering the resulting compound of formula (IIIB) in free form or in form of a salt, and optionally converting a compound of the formula (IIIB) obtained into a different compound of the formula (IIIB), and/or converting an obtained salt of a compound of the formula (IIIB) into a different salt thereof, and/or converting an obtainable free compound of the formula (IIIB) into a salt thereof, and/or separating an obtainable isomer of a compound of the formula (IIIB) from one or more different obtained isomers of the formula (IIIB).

The invention also relates to compounds of formula (IIIC) or a salt thereof

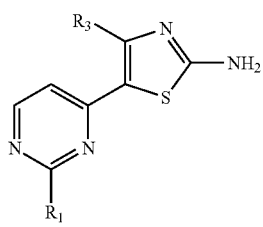

(IIIC)

wherein the substituents are as defined for a compound of formula (I).

The present invention further relates to processes for the production of a compound of formula (IIIC). In principle, all ring closing reactions are suitable and may be applied by using the respective starting material. The invention thus also relates to a process for preparing a compound of formula (IIIC), which comprises reacting a compound of formula (VI)

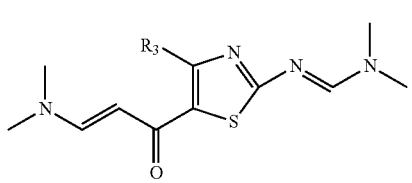

(VI)

wherein R³ is as defined herein and may additionally represent halo, with a compound of formula (VII)

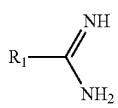

(VII)

wherein R¹ is as defined herein; optionally in the presence of a diluent and optionally in the presence of a reaction aid; and recovering the resulting compound of formula (IIIC) in free form or in form of a salt, and optionally converting a compound of the formula (IIIC) obtained into a different compound of the formula (IIIC), and/or converting an obtained salt of a compound of the formula (IIIC) into a different salt thereof, and/or converting an obtainable free compound of the formula (IIIC) into a salt thereof, and/or separating an obtainable isomer of a compound of the formula (IIIC) from one or more different obtained isomers of the formula (IIIC).

The invention further relates to compounds of formula (IIID) or a salt thereof

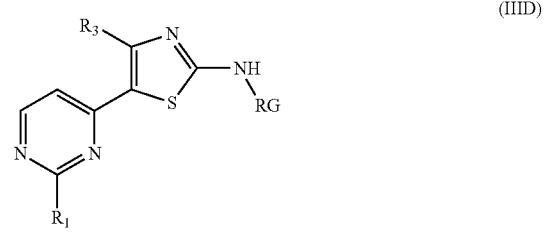

(IIID)

wherein R¹ is as defined herein, RG represents a reactive group, particularly imidazolylcarbonyl, R³ is as defined herein and may additionally represent halo.

The present invention further relates to processes for the production of a compound of formula (IIID). In principle, all known processes which convert an amine or salt thereof into a corresponding activated derivative are suitable and may be applied by using the respective starting material. The invention thus also relates to a process for preparing a compound of formula (IIID), which comprises reacting a compound of formula (IIIC)

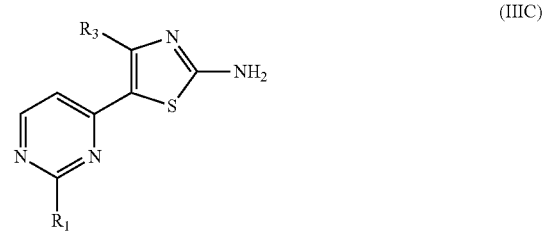

(IIIC)

wherein the substituents are as defined above, with an activating reagent, such as 1,1'-carbonyldiimidazole, optionally in the presence of a diluent and optionally in the presence of a reaction aid; and recovering the resulting compound of formula (IIID) in free form or in form of a salt, and optionally converting a compound of the formula (IIID) obtained into a different compound of the formula (IIID), and/or converting an obtained salt of a compound of the formula (IIID) into a different salt thereof, and/or converting an obtainable free compound of the formula (IIID) into a salt thereof, and/or separating an obtainable isomer of a compound of the formula (IIID) from one or more different obtained isomers of the formula (IIID).

The invention further relates to compounds of formula (VI) or a salt thereof

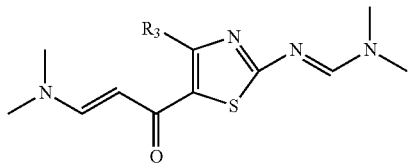

(VI)

wherein R³ is as defined herein and may additionally represent halo.

The present invention further relates to processes for the production of a compound of formula (VI). In principle, all known processes suitable for such a conversion may be applied by using the respective starting material. The invention thus also relates to a process for preparing a compound of formula (IIID), which comprises reacting a compound of formula (IIX)

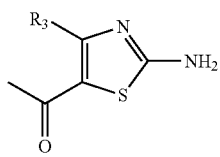

(IIX)

wherein R³ is as defined in formula (I) and may additionally represent halo, with an acetal of dimethylformamide, such as DMF-dimethylacetal, to obtain a compound of formula (VI); recovering the resulting compound of formula (IIID) in free form or in form of a salt, and optionally converting a compound of the formula (IIX) obtained into a different compound of the formula (IIX), and/or converting an obtained salt of a compound of the formula (IIX) into a different salt thereof, and/or converting an obtainable free compound of the formula (IIX) into a salt thereof, and/or separating an obtainable isomer of a compound of the formula (IIX) from one or more different obtained isomers of the formula (IIX).

The compounds of the formula (I),

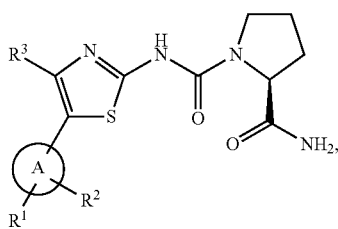

(I)

also including the sub-formulae (IA), (IB), and pharmaceutically acceptable salts thereof, wherein
A represents heteroaryl;
R¹ represents (1) optionally substituted alkyl; (2) optionally substituted cycloalkyl; (3) optionally substituted aryl; (4) optionally substituted amine; (5) optionally substituted sulfonyl; (6) halo;
R² represents hydrogen, deuterium or a substituent as defined for R¹;
R³ represents hydrogen, halo, optionally substituted alkyl;

are useful as pharmaceuticals. The invention therefore relates in one embodiment to compositions for human or veterinary use where inhibition of PI3K is indicated. This embodiment also includes the compound (S)-Pyrrolidine-1,2-dicarboxylic acid 2-amide 1-{5-[2-(tert-butyl)-pyrimidin-4-yl]-4-methyl-thiazol-2-yl}-amide, but alternatively, excludes said compound.

In one embodiment, the invention relates to the treatment of cellular proliferative diseases such as tumor and/or cancerous cell growth mediated by PI3K. Diseases may include those showing overexpression or amplification of PI3K alpha, somatic mutation of PIK3CA or germline mutations or somatic mutation of PTEN or mutations and translocation of p85α that serve to up-regulate the p85-p110 complex. In particular, the compounds are useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Walden stroem disease.

In other embodiments, the condition or disorder (e.g. PI3K-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

For the above uses the required dosage will of course vary depending on the mode of administration, the particular condition to be treated and the effect desired. In general, satisfactory results are indicated to be obtained systemically at daily dosages of from about 0.03 to about 100.0 mg/kg per body weight, e.g. about 0.03 to about 10.0 mg/kg per body weight. An indicated daily dosage in the larger mammal, e.g. humans, is in the range from about 0.5 mg to about 3 g, e.g. about 5 mg to about 1.5 g, conveniently administered, for example, in divided doses up to four times a day or in retard form. Suitable unit dosage forms for oral administration comprise from ca. 0.1 to about 500 mg, e.g. about 1.0 to about 500 mg active ingredient.

The compounds of formula (I) may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, by inhalation, intranasally, or in a suppository form.

The compounds of formula (I) may be administered in free form or in pharmaceutically acceptable salt form e.g. as indicated above. Such salts may be prepared in conventional manner and exhibit the same order of activity as the free compounds.

Consequently, the invention also provides:
a method for preventing or treating conditions, disorders or diseases mediated by the activation of the PI3K (e.g. PI3 kinase alpha) enzyme e.g. such as indicated above, in a subject in need of such treatment, which method comprises administering to said subject an effective amount of a compound of formula (I) or a pharmaceutically acceptable salt thereof
a compound of formula (I), in free form or in a pharmaceutically acceptable salt form as a pharmaceutical, e.g. in any of the methods as indicated herein.
a compound of the formula (I) in free form or in pharmaceutically acceptable salt form for use as pharmaceutical, e.g. in any of the methods as indicated herein, in particular for the use in one or more phosphatidylinositol 3-kinase mediated diseases.
the use of a compound of formula (I) in free form or in pharmaceutically acceptable salt form in any of the methods as indicated herein, in particular for the treatment of one or more phosphatidylinositol 3-kinase mediated diseases.
the use of a compound of formula (I) in free form or in pharmaceutically acceptable salt form in any of the methods as indicated herein, in particular for the manufacture of a medicament for the treatment of one or more phosphatidylinositol 3-kinase mediated diseases.

PI3K serves as a second messenger node that integrates parallel signaling pathways, evidence is emerging that the combination of a PI3K inhibitor with inhibitors of other pathways will be useful in treating cancer and proliferative diseases in humans.

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., Breast Can. Res. Treat. 91:187 (2005), Woods Ignatoski et al., Brit. J. Cancer 82:666 (2000), Nagata et al., Cancer Cell 6:117 (2004)).

A variety of human malignancies express activitating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297 (2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Aid also abrogates its role to arrest the cell cycle (Viglietto et al., Nat. Med. 8:1145 (2002)).

Accordingly, in a further aspect, the compounds of formulas I are used in the treatment of hormone dependent cancers, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Ab1 employs the Ras-Raf kinase pathway to elicit its effects. In addition, inhibiting more than one kinase in the same pathway provides additional protection against resistance-conferring mutations.

Accordingly, in another aspect, the compounds of formulas I are used in combination with at least one additional agent selected from the group of kinase inhibitors, such as Gleevec®, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer. Ther. 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., Nature Medicine 11:507-514 (2005)). Thus, a PI3K inhibitor that inhibits p110β would be useful as a single agent or in combination in anti-thrombotic therapy. The isoform p110δ, the product of the PIK3CD gene, is important in B cell function and differentiation (Clayton et al., J. Exp. Med. 196:753-763 (2002)), T-cell dependent and independent antigen responses (Jou et al., Mol. Cell. Biol. 22:8580-8590 (2002)) and mast cell differentiation (Ali et al., Nature 431:1007-1011 (2004)). Thus, it is expected that p110δ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

The invention further provides pharmaceutical compositions comprising at least one compound of formula (I), together with a pharmaceutically acceptable excepient suitable for administration to a human or animal subject, either alone or together with other anticancer agents.

The invention further provides methods of treating human or animal subjects suffering from a cellular proliferative disease, such as cancer. The invention thus provides methods of treating a human or animal subject in need of such treatment, comprising administering to the subject a therapeutically effective amount of a compound of formula (I) either alone or in combination with one or more other anticancer agents. In particular, compositions will either be formulated together as a combination therapeutic or administered separately. Suitable anticancer agents for use with a compound of formula (I) include, but are not limited to, one or more compounds selected from the group consisting of kinase inhibitors, anti-estrogens, anti androgens, other inhibitors, cancer chemotherapeutic drugs, alkylating agents, chelating agents, biological response modifiers, cancer vaccines, agents for antisense therapy as set forth below:

A. Kinase Inhibitors:

Kinase inhibitors for use as anticancer agents in conjunction with the compound of the formula (I) include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883, 113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-t][1,2,4]triazines, ZK-304709, Veglin®, VMDA-3601, EG-004, CEP-701 (U.S. Pat. No. 5,621,100), Candy (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens:

Estrogen-targeting agents for use in anticancer therapy in conjunction with the compound of formula (I) include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens:

Androgen-targeting agents for use in anticancer therapy in conjunction with the compound of formula (I) include flutamide, bicalutamide, finasteride, aminoglutethamide, ketoconazole, and corticosteroids.

D. Other Inhibitors:

Other inhibitors for use as anticancer agents in conjunction with the compound of formula (I) include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs:

Particular cancer chemotherapeutic agents for use as anticancer agents in conjunction with the compound of formula (I) include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepeside®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex, teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents:

Alkylating agents for use in conjunction with the compound of formula (I) include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents:

Chelating agents for use in conjunction with the compound of formula (I) include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers:

Biological response modifiers, such as immune modulators, for use in conjunction with the compound of formula (I) include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04164759, and WO 04/60308).

I. Cancer Vaccines:

Anticancer vaccines for use in conjunction with the compound of formula (I) include Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compound of formula (I) also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

The compound of formula (I) can also be combined in a pharmaceutical composition with bronchiodilatory or antihistamine drugs substances. Such bronchiodilatory drugs include anticholinergic or antimuscarinic agents, in particular ipratropium bromide, oxitropium bromide, and tiotropium bromide, and β-2-adrenoreceptor agonists such as salbutamol, terbutaline, salmeterol, carmoterol, milveterol and, especially, formoterol or indacaterol. Co-therapeutic antihistamine drug substances include cetirizine hydrochloride, clemastine fumarate, promethazine, loratadine, desloratadine diphenhydramine and fexofenadine hydrochloride.

The invention provides in a further aspect a combination comprising a compound of formula (I) and one or more compounds that are useful for the treatment of a thrombolytic disease, heart disease, stroke, etc. Such compounds include aspirin, a streptokinase, a tissue plasminogen activator, a urokinase, a anticoagulant, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The invention provides in a further aspect a combination comprising a compound of formula (I) and one or more compounds that are useful for the treatment of antihypertension. Such compounds include ACE inhibitors, lipid lowering agents such as statins, LIPITOR (Atorvastatin calcium), calcium channel blockers such as NORVASC (amlodipine besylate).

The invention provides in a further aspect a combination comprising a compound of formula (I) and one or more compounds selected from the group consisting of fibrates, beta-blockers, NEPI inhibitors, Angiotensin-2 receptor antagonists and platelet aggregation inhibitors.

The invention provides in a further aspect a combination comprising a compound of formula (I) and a compound suitable for the treatment of inflammatory diseases, including rheumatoid arthritis. Such compound may be selected from the group consisting of TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2×7 inhibitors, α2αinhibitors, NEUROTIN, pregabalin, low dose methotrexate, leflunomide, hydroxyxchloroquine, d-penicillamine, auranofin or parenteral or oral gold.

The invention provides in a further aspect a combination comprising a compound of formula (I) and a compound suitable for the treatment of osteoarthritis. Such compound may be selected from the group consisting of standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The invention provides in a further aspect a combination comprising a compound of formula (I) and an antiviral agent and/or an antisepsis compound. Such antiviral agent may be selected from the group consisting of Viracept, AZT, acyclovir and famciclovir. Such antisepsis compound may be selected from the group consisting of Valant.

The invention provides in a further aspect a combination comprising a compound of formula (I) and one or more agents selected from the group consisting of CNS agents such as antidepressants (sertraline), anti-Parkinsonian drugs (such as deprenyl, L-dopa, Requip, Mirapex; MAOB inhibitors (such as selegine and rasagiline); comP inhibitors (such as Tasmar); A-2 inhibitors; dopamine reuptake inhibitors; NMDA antagonists; Nicotine agonists; Dopamine agonists; and inhibitors of neuronal nitric oxide synthase).

The invention provides in a further aspect a combination comprising a compound of formula (I) and one or more anti-Alzheimer's drugs. Such anti-Alzheimer Drug may be selected from the group consisting of donepezil, tacrine, α2δinhibitors, NEUROTIN, pregabalin, COX-2 inhibitors, propentofylline or metrifonate.

The invention provides in a further aspect a combination comprising a compound of formula (I) and anosteoporosis agents and/or an immunosuppressant agent. Such osteoporosis agents may be selected from the group consisting of EVISTA (raloxifene hydrochloride), droloxifene, lasofoxifene or fosomax. Such immunosuppressant agents may be selected from the group consisting of FK-506 and rapamycin.

In another aspect of the preferred embodiments, kits that include one or more compound of formula (I) an a combination partner as disclosed herein are provided. Representative kits include a PI3K inhibitor compound (e.g., a compound of formula (I)) and a package insert or other labeling including directions for treating a cellular proliferative disease by administering a PI3K inhibitory amount of the compound(s).

In general, the compounds of formula (I) will be administered in a therapeutically effective amount by any of the accepted modes of administration for agents that serve similar utilities. The actual amount of the compound of formula (I), i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician. Therapeutically effective amounts of compounds of formulas I may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of formula (I) will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the formula (I) is inhalation. This is an effective method for delivering a therapeutic agent directly to the respiratory tract.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

The invention also relates to formulations wherein the particle size of a compound of formula (I) between 10-1000 nm, preferably 10-400 nm. Such pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Both documents are included by reference.

In a further aspect, the invention provides pharmaceutical compositions comprising a (therapeutically effective amount) of a compound of formula (I), and at least one pharmaceutically acceptable excipient. Acceptable excipients are non-toxic, aid administration, and do not adversely affect the therapeutic benefit of the compound of formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the formula (I) in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The invention further relates to pharmaceutical compositions comprising (i.e. containing or consisting of) at least one compound of formula (I) and at least one pharmaceutically acceptable excipient.

Pharmaceutical compositions comprising a compound of formula (I) in free form or in pharmaceutically acceptable salt form in association with at least one pharmaceutical acceptable excipient (such as a carrier and/or diluent) may be manufactured in conventional manner by mixing the components.

Combined pharmaceutical compositions comprising a compound of formula (I) in free form or in pharmaceutically acceptable salt form and further comprising a combination partner (either in one dosage unit form or as a kit of parts) in association with at least one pharmaceutical acceptable carrier and/or diluent may be manufactured in conventional manner by mixing with a pharmaceutically acceptable carrier and/or diluent with said active ingredients.

Consequently, the invention provides in further aspects

- a combined pharmaceutical composition, e.g. for use in any of the methods described herein, comprising a compound of formula (I) in free form or pharmaceutically acceptable salt form in association with a pharmaceutically acceptable diluent and/or carrier.
- a combined pharmaceutical composition comprising a compound of formula (I) in free form or in pharmaceutically acceptable salt form as active ingredient; one or more pharmaceutically acceptable carrier material(s) and/or diluents and optionally one or more further drug substances. Such combined pharmaceutical composition may be in the form of one dosage unit form or as a kit of parts.
- a combined pharmaceutical composition comprising a therapeutically effective amount of a compound of formula (I) in free form or in pharmaceutically acceptable salt form and a second drug substance, for simultaneous or sequential administration.
- a method as defined above comprising co-administration, e.g. concomitantly or in sequence, of a therapeutically effective non-toxic amount of a compound of formula (I) or a pharmaceutically acceptable salt thereof, and at least a second drug substance, e.g. as indicated above.
- a pharmaceutical combination, e.g. a kit, comprising a) a first agent which is a compound of formula (I) as disclosed herein, in free form or in pharmaceutically acceptable salt form, and b) at least one co-agent, e.g. as indicated above; whereby such kit may comprise instructions for its administration.

The following examples of compounds of formula (I) illustrate the invention without limiting the scope thereof. Methods for preparing such compounds are described hereinafter.

EXAMPLE 1

(S)-Pyrrolidine-1,2-dicarboxylic acid 2-amide 1-{[5-(2-tert-butyl-pyridin-4-yl)-4-methyl-thiazol-2-yl]-amide}

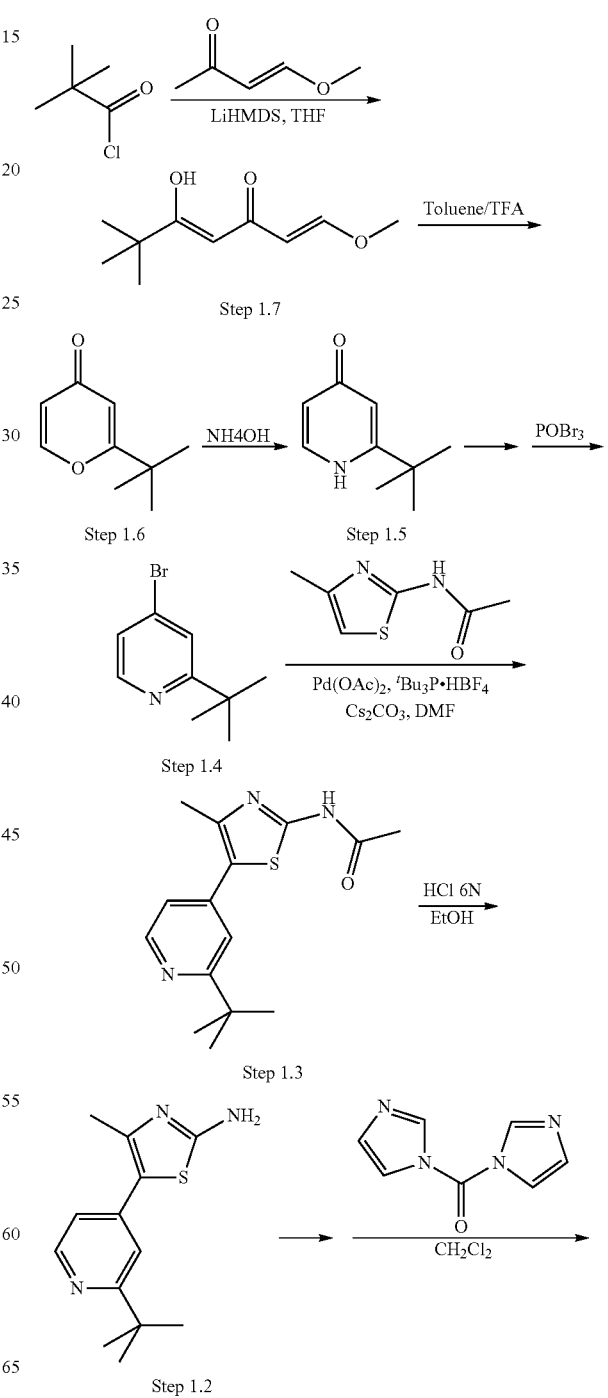

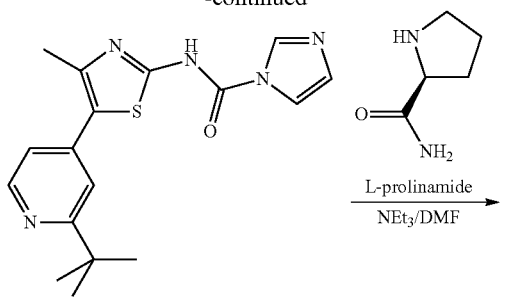

Step 1.1

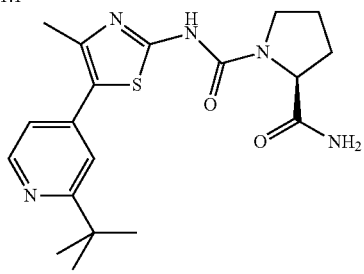

Example 1

Et₃N (1.54 mL, 11.1 mmol, 3 eq) is added to a solution of imidazole-1-carboxylic acid [5-(2-tert-butyl-pyridin-4-yl)-4-methyl-thiazol-2-yl]amide (Step 1.1) (1.26 g, 3.7 mmol) and L-prolinamide (0.548 g, 4.8 mmol, 1.3 eq) in DMF (25 mL), under an argon atmosphere. The reaction mixture is stirred for 14 h at rt, quenched by addition of a saturated solution of NaHCO₃, and extracted with EtOAc. The organic phase is washed with a saturated solution of NaHCO₃, dried (Na₂SO₄), filtered and concentrated. The residue is purified by silica gel column chromatography (DCM/MeOH, 1:0→94:6), followed by trituration in Et₂O to afford 1.22 g of the title compound as an off-white solid: ESI-MS: 388.1 [M+H]$^+$; $t_R$=2.35 min (System 1); TLC: $R_f$=0.36 (DCM/MeOH, 9:1). $^1$H NMR (400 MHz, DMSO-d6) δ(ppm): 1.32 (s, 9H) 1.75-1.95 (m, 3H) 1.97-2.13 (m, 1H) 2.39 (s, 3H) 3.38-3.50 (m, 1H) 3.52-3.65 (m., 1H) 4.10-4.40 (m, 1H) 6.94 (br. s., 1H) 7.22 (d, 1H) 7.30-7.48 (m, 2H) 8.49 (d, 1H) 10.87 (br. s., 1H)

Step 1.1: Imidazole-1-carboxylic acid [5-(2-tert-butyl-pyridin-4-yl)-4-methyl-thiazol-2-yl]-amide

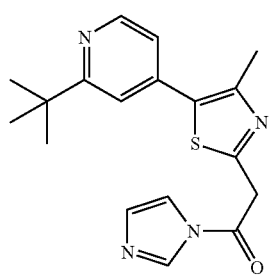 [SMILES: Cc1nc(CC(=O)n2ccnc2)sc1-c1ccnc(C(C)(C)C)c1]

A mixture of 5-(2-tert-butyl-pyridin-4-yl)-4-methyl-thiazol-2-ylamine (Step 1.2) (1 g, 4.05 mmol) and 1,1'-carbonyl-diimidazole (0.984 g, 6.07 mmol, 1.5 eq) in DCM (50 mL) is stirred for 4 h at reflux and allowed to cool. The resulting precipitate is collected by filtration to provide 1.26 g of the title compound as white solid: ESI-MS: 340.2 [M–H]$^–$; $t_R$=2.85 min (System 1).

Step 1.2: 5-(2-tert-Butyl-pyridin-4-yl)-4-methyl-thiazol-2-ylamine

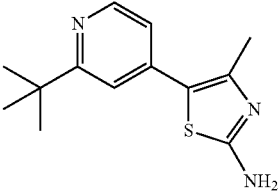 [SMILES: Cc1nc(N)sc1-c1ccnc(C(C)(C)C)c1]

A mixture of N-[5-(2-tert-butyl-pyridin-4-yl)-4-methyl-thiazol-2-yl]-acetamide (Step 1.3) (2 g, 7 mmol), a 6N aqueous solution of HCl (10 mL) and EtOH (50 mL) is stirred for 2 h at 85° C., allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (DCM/MeOH, 1:0→96:4) to afford 1.21 g of the title compound as a yellow solid: ESI-MS: 248.1 [M+H]$^+$; TLC: $R_f$=0.36 (DCM/MeOH, 9:1).

Step 1.3: N-[5-(2-tert-Butyl-pyridin-4-yl)-4-methyl-thiazol-2-yl]-acetamide

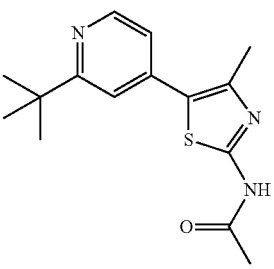 [SMILES: CC(=O)Nc1nc(C)c(-c2ccnc(C(C)(C)C)c2)s1]

A mixture of 2-acetamido-4-methylthiazole (1.2 g, 7.7 mmol, 1.1 eq), cesium carbonate (4.55 g, 14 mmol, 2 eq), tri-tert-butylphosphinium tetrafluoroborate (0.406 g, 1.4 mmol, 0.2 eq), palladium (II) acetate (0.15 g, 0.7 mmol, 0.1 eq) and 4-bromo-2-tert-butyl-pyridine (Step 1.4) (1.5 g, 7 mmol) in DMF (50 mL) is stirred for 1.5 h at 90° C. under an argon atmosphere, allowed to cool, quenched by addition of a saturated solution of NaHCO₃ and filtered through a pad of celite. The filtrate is extracted with EtOAc. The organic phase is washed with a saturated solution of NaHCO₃, dried (Na₂SO₄), filtered and concentrated. The residue is purified by silica gel column chromatography (DCM/MeOH, 1:0→97:3) to afford 2.02 g of the title compound as a yellow solid: ESI-MS: 290.1 [M+H]⁺; TLC: $R_f$=0.35 (DCM/MeOH, 9:1).

Step 1.4: 4-Bromo-2-tert-butyl-pyridine

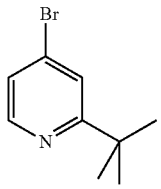

A mixture of 2-tert-butyl-1H-pyridin-4-one (Step 1.5) (4.25 g, 28 mmol) and POBr₃ (8.88 g, 31 mmol, 1.1 eq) is heated to 120° C., stirred for 15 min, allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (Hex/EtOAc, 95:5) to afford 5.18 g of the title compound as a yellow oil: ESI-MS: 214.0/216.0 [M+H]⁺; $t_R$=2.49 min (System 1); TLC: $R_f$=0.35 (Hex/EtOAc, 1:1).

Step 1.5: 2-tert-Butyl-1H-pyridin-4-one

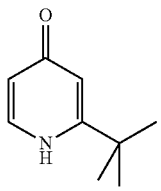

A mixture of 2-tert-butyl-pyran-4-one (Step 1.6) (5.74 g, 37.7 mmol) and a 30% aqueous solution of ammonium hydroxide (100 mL) is stirred for 1 h at reflux, allowed to cool and concentrated. The residue is triturated with MeOH (200 mL) and filtered. The filtrate is concentrated and the residue purified by silica gel column chromatography (DCM/MeOH/NH₃$^{aq}$, 94:5:1→92:7:1) to afford 4.46 g of the title compound as a yellow solid: ESI-MS: 152.0 [M+H]⁺; $t_R$=1.45 min (System 1); TLC: $R_f$=0.11 (DCM/MeOH, 9:1).

Step 1.6: 2-tent-Butyl-pyran-4-one

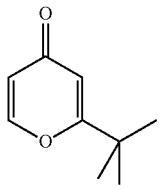

A mixture of 5-hydroxy-1-methoxy-6,6-dimethyl-hepta-1, 4-dien-3-one (Step 1.7) (6.8 g, 36.9 mmol) and TFA (5.65 mL, 74 mmol, 2 eq) in benzene (250 mL) is stirred for 14 h at it and concentrated. Purification of the residue by silica gel column chromatography (Hex/EtOAc, 1:0→75:25) provides 5.74 g of the title compound as a yellow oil: ESI-MS: 153.1 [M+H]⁺; $t_R$=3.21 min (System 1); TLC: $R_f$=0.22 (Hex/EtOAc, 1:1).

Step 1.7: 5-Hydroxy-1-methoxy-6,6-dimethyl-hepta-1,4-dien-3-one

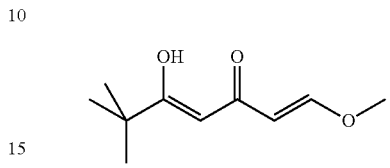

LiHMDS (1M in THF, 100 mL, 2 eq) is added dropwise to a cold (−78° C.) solution of 4-methoxy-3-buten-2-one (10 mL, 100 mmol, 2 eq) in THF (400 mL). After a 30 min stirring at −78° C., a solution of pivaloyl chloride (6.12 mL, 50 mmol) in THF (100 mL) is added. The resulting mixture is allowed to warm to it over 2 h and quenched by addition of a saturated solution of NH₄Cl. THF is removed under vacuum. The concentrated mixture is extracted with Et₂O. The organic phase is washed with brine, dried (Na₂SO₄), filtered and concentrated. The residue is purified by silica gel column chromatography (Hex/EtOAc, 1:0→85:15) to afford 6.83 g of the title compound as a yellow oil: ESI-MS: 185.1 [M+H]⁺; TLC: $R_f$=0.87 (Hex/EtOAc, 1:1).

EXAMPLE 2

(S)-Pyrrolidine-1,2-dicarboxylic acid 2-amide 1-{[5-(2-cyclopropyl-pyridin-4-yl)-4-methyl-thiazol-2-yl] amide}

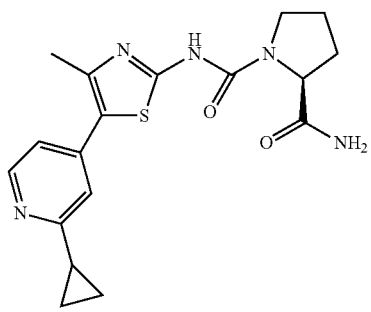 [SMILES: Cc1nc(NC(=O)N2CCC[C@H]2C(N)=O)sc1-c1ccnc(C2CC2)c1]

The title compound is prepared in analogy to the procedure described in Example 1 but with the following modifications. In Step 1.1, the reaction mixture is stirred for 4 h at reflux. In Step 1.2, the reaction mixture is stirred for 2 h at 85° C. In Step 1.3, 4-chloro-2-(1-methyl-cyclopropyl)-pyridine (Step 2.1) is used and the reaction mixture is stirred for 2 h at 150° C.

Title compound: ESI-MS: 372.1 [M+H]⁺; TLC: R₁=0.35 (DCM/MeOH, 9:1).

Step 2.1: 4-Chloro-2-cyclopropyl-pyridine

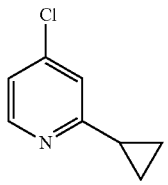

The title compound is prepared according to a modification of a procedure described in the literature [Comins, D. L.; Mantlo, N. B., Journal of Organic Chemistry, (1985), 50, 4410-4411]

Cyclopropylmagnesium bromide (0.5M in THF, 100 mL, 50 mmol, 2.2 eq) is added in one portion to a cold (−78° C.) suspension of 4-chloropyridine hydrochloride (3.4 g, 22 mmol) in THF (68 mL). After a 10 min stirring at −78° C., phenyl chloroformate (2.76 mL, 22 mmol) is added dropwise. The reaction mixture is stirred at −78° C. for 15 min, allowed to warm to rt, quenched by addition of a 20% aqueous solution of NH₄Cl and extracted with Et₂O (2×100 mL). The organic phase is washed with a saturated solution of NaHCO₃ (50 mL), dried (Na₂SO₄), filtered and concentrated. To the residue dissolved in toluene (100 mL), a solution of o-chloranil (6 g, 24.2 mmol, 1.1 eq) in glacial AcOH (50 mL) is added. The reaction mixture is stirred for 14 h at rt, cooled to 0° C., basified by addition of a 10% aqueous solution of NaOH and filtered through a pad of celite. The organic layer from the filtrate is washed with H₂O (20 mL) and extracted with a 10% aqueous solution of HCl (3×25 mL). The combined acidic layers are basified by addition of 20% aqueous solution of NaOH and extracted with DCM (3×25 mL). The organic phase is washed with H₂O (50 mL), dried (Na₂SO₄), filtered and concentrated. The residue purified by silica gel column chromatography (DCM/MeOH, 1:0→99:1) to afford 0.951 g of the title compound as a colorless oil: ESI-MS: 154.1 [M+H]⁺; $t_R$=1.41 min (System 1); TLC: R$_f$=0.85 (DCM/MeOH, 9:1).

EXAMPLE 3

(S)-Pyrrolidine-1,2-dicarboxylic acid 2-amide 1-({5-[2-(2-fluoro-phenyl)-pyridin-4-yl]-4-methyl-thiazol-2-yl}-amide)

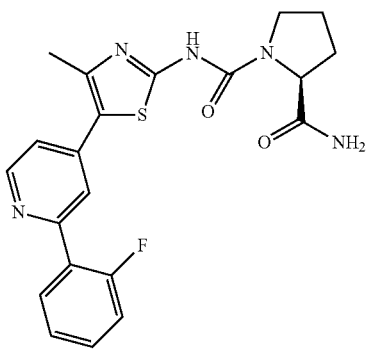 [SMILES: Cc1nc(NC(=O)N2CCC[C@H]2C(N)=O)sc1-c1ccnc(-c2ccccc2F)c1]

The title compound is prepared in analogy to the procedure described in Example 1 but using 4-chloro-2-(2-fluoro-phenyl)-pyridine (Step 3.1) and stirring the corresponding mixture for 2 h at 150° C. in Step 1.3: ESI-MS: 426.1 [M+H]⁺; $t_R$=2.60 min (System 1); TLC: R$_f$=0.40 (DCM/MeOH, 9:1).

Step 3.1: 4-Chloro-2-(2-fluoro-phenyl)-pyridine

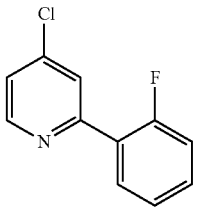 [SMILES: Fc1ccccc1-c1cc(Cl)ccn1]

A mixture of 2-fluorophenylboronic acid (141 mg, 1 mmol, 1.2 eq) in EtOH (1 mL) is added to a mixture of 4-chloro-2-iodo-pyridine [Choppin, S.; Gros, P.; Fort, Y., European Journal of Organic Chemistry (2001), (3), 603-606] (200 mg, 0.84 mmol), PdCl₂(dppf) (18 mg, 0.025 mmol, 0.03 equiv) and Na₂CO₃ (2 M solution in H₂O, 1.68 mL, 3.36 mmol, 4 equiv) in toluene (2 mL) at 105° C., under an argon atmosphere. The reaction mixture is stirred at 105° C. for 1 h, allowed to cool to rt, quenched by addition of a saturated solution of NaHCO₃ and extracted with EtOAc. The organic phase is washed with a saturated solution of NaHCO₃, dried (Na₂SO₄), filtered and concentrated. The residue is purified by silica gel column chromatography (Hex/EtOAc, 1:0→97:3) to afford 127 mg of the title compound as a white solid: ESI-MS: 208.1 [M+H]$^+$; $t_R$=4.66 min (System 1); TLC: $R_f$=0.27 (Hex/EtOAc, 9:1).

EXAMPLE 4

(S)-Pyrrolidine-1,2-dicarboxylic acid 2-amide 1-{[5-(2-cyclobutyl-pyridin-4-yl)-4-methyl-thiazol-2-yl]-amide}

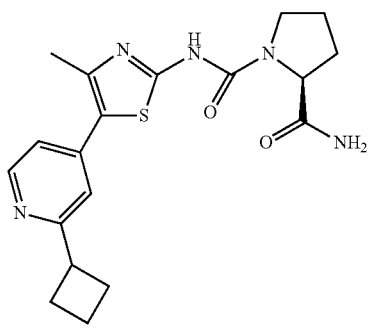 [SMILES: Cc1nc(NC(=O)N2CCC[C@H]2C(N)=O)sc1-c1ccnc(C2CCC2)c1]

The title compound is prepared in analogy to the procedure described in Example 1 but with the following modifications. In Example 1, the reaction mixture is stirred for 4 h at rt, diluted with EtOAc and H$_2$O, and extracted with EtOAc. After drying and concentration of the organic phase, the residue is purified by trituration in DCM. In Step 1.3, the reaction mixture is stirred for 2 h at 120° C., cooled, diluted with EtOAc and H$_2$O, filtered through a pad of celite and extracted with EtOAc. After drying and concentration of the organic phase, the residue is purified by trituration in Et$_2$O. In Step 1.5, the reaction mixture is stirred for 1 h at 80° C. and trituration in MeOH is not performed. In Step 1.7, 4-methoxy-3-buten-2-one in THF is added to a cold (−78° C.) solution of LiHMDS in THF. After 30 min, cyclobutylcarbonyl chloride in THF is added and the reaction mixture is allowed to reach it over 18 h.

Title compound: ESI-MS: 386.1 [M+H]$^+$; TLC: R$_1$=0.11 (DCM/MeOH, 95:5).

EXAMPLE 5

(S)-Pyrrolidine-1,2-dicarboxylic acid 2-amide 1-({4-methyl-5-[2-(1-methyl-cyclopropyl)-pyridin-4-yl]-thiazol-2-yl}-amide)

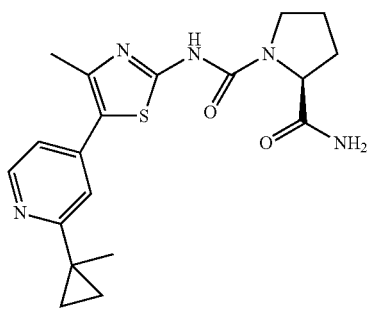 [SMILES: Cc1nc(NC(=O)N2CCC[C@H]2C(N)=O)sc1-c1ccnc(C2(C)CC2)c1]

The title compound is prepared in analogy to the procedure described in Example 1 but 1 but with the following modifications. In Step 1.1, the reaction mixture is stirred for 14 h at reflux. In Step 1.2, the reaction mixture is stirred for 1 h at 85° C. In Step 1.3, the reaction mixture is stirred for 3 h at 120° C. In Step 1.5, the reaction mixture is stirred for 1 h at 65-70° C. and trituration in MeOH is not performed. In Step 1.7, 1-methyl-cyclopropanecarbonyl chloride (Step 5.1) is used.

Title compound: ESI-MS: 386.1 [M+H]$^+$; TLC: R$_f$=0.40 (DCM/MeOH, 9:1). $^1$H NMR (400 MHz, DMSO-d6) δ (ppm): 0.71-0.87 (m, 2H) 1.11-1.26 (m, 2H) 1.47 (s, 3H) 1.74-1.96 (m, 3H) 2.00-2.15 (m, 1H) 2.39 (s, 3H) 3.35-3.52 (m, 1H) 3.52-3.73 (m, 1H) 4.10-4.40 (m, 1H) 6.93 (br. s., 1H) 7.15 (dd, 1H) 7.27 (s, 1H) 7.35 (s, 1H) 8.40 (d, 1H) 10.99 (br. s., 1H)

Step 5.1: 1-Methyl-cyclopropanecarbonyl chloride

A mixture of 1-methyl-cyclopropanecarboxylic acid (10 g, 100 mmol) and oxalyl chloride (10.49 ml, 120 mmol, 1.2 eq) in CHCl$_3$ (80 ml) is stirred for 4 h at 70° C. The reaction mixture is concentrated to afford 11.8 g of the title compound as a yellow oil which is used without further purification.

EXAMPLE 6

(S)-Pyrrolidine-1,2-dicarboxylic acid 2-amide 1-({4-methyl-5-[2-(1-methyl-cyclobutyl)-pyridin-4-yl]-thiazol-2-yl}-amide)

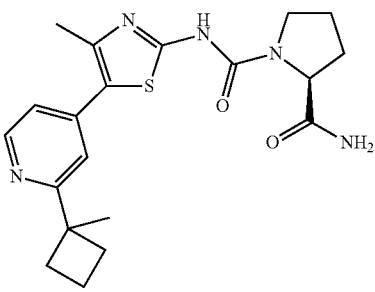 [SMILES: Cc1nc(NC(=O)N2CCC[C@H]2C(N)=O)sc1-c1ccnc(C2(C)CCC2)c1]

The title compound is prepared in analogy to the procedure described in Example 1 but with the following modifications. In Example 1, the reaction mixture is quenched by dilution with EtOAc and H$_2$O, and extracted with EtOAc. In Step 1.2, the reaction mixture is stirred for 2 h at 100° C. In Step 1.3, the reaction mixture is stirred for 3 h at 100° C., diluted with EtOAc/H$_2$O, and extracted with EtOAc. After drying and concentration of the organic phase, the residue is purified by silica gel column chromatography (Hex/EtOAc, 1:4). In Step 1.5, the reaction mixture is stirred for 2 h at 80° C. and trituration in MeOH is not performed. In Step 1.7, 4-methoxy-3-buten-2-one (50 mmol) in THF (100 mL) is added to a cold (−78° C.) solution of LiHMDS (1M in THF, 100 mL) in THF (200 mL). After 30 min, 1-methyl-cyclobutane chloride (Step 6.1) is added and the reaction mixture is allowed to reach rt over 18 h.

Title compound: ESI-MS: 400.1 [M+H]⁺; TLC: $R_f$=0.06 (DCM/MeOH/NH$_3^{aq}$, 94:5:1).

Step 6.1: 1-Methyl-cyclobutanecarbonyl chloride

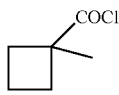

The title compound is prepared in analogy to the procedure described in Step 5.1 but using 1-methyl-cyclobutanecarboxylic acid [Cowling, S. J.; Goodby, J. W., Chemical Communications, (2006), (39), 4107-4109].

EXAMPLE 7

(S)-Pyrrolidine-1,2-dicarboxylic acid 2-amide 1-{[5-(2-tert-butyl-pyridin-4-yl)-thiazol-2-yl]-amide}

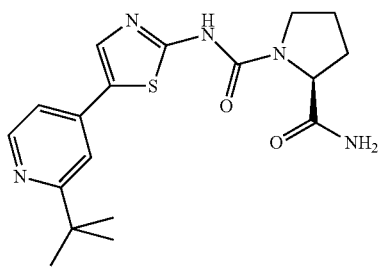 [SMILES: CC(C)(C)c1cc(-c2cnc(NC(=O)N3CCC[C@H]3C(N)=O)s2)ccn1]

The title compound is prepared in analogy to the procedure described in Example 1 with the following modifications. In Example 1, the reaction mixture is stirred for 16 h at rt, quenched by dilution with EtOAc/H₂O, and extracted with EtOAc. In Step 1.1, the reaction mixture is stirred for 2 h at reflux. In Step 1.2, the reaction mixture is stirred for 1 h at 100° C. In Step 1.3, N-thiazol-2-yl-acetamide is used. The reaction mixture is stirred for 2 h at 120° C., diluted with EtOAc/H₂O and extracted with EtOAc. After drying and concentration of the organic phase, the residue is purified by silica gel column chromatography (Hex/EtOAc, 1:1), followed by trituration in Et₂O.

Title compound: ESI-MS: 374.1 [M+H]⁺; $t_R$=2.16 min (System 1); TLC: $R_f$=0.10 (DCM/MeOH/NH$_3^{aq}$, 94:5:1).

EXAMPLE 8

(S)-Pyrrolidine-1,2-dicarboxylic acid 2-amide 1-{[5-(2-isopropyl-pyridin-4-yl)-4-methyl-thiazol-2-yl]-amide}

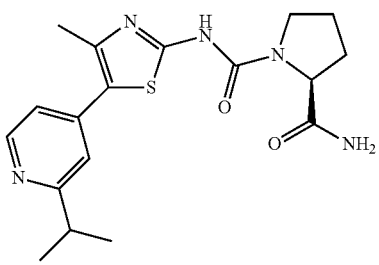 [SMILES: Cc1nc(NC(=O)N2CCC[C@H]2C(N)=O)sc1-c1ccnc(C(C)C)c1]

The title compound is prepared in analogy to the procedure described in Example 1 but with the following modifications. In Example 1, the reaction mixture is stirred for 16 h at rt, quenched by dilution with EtOAc/H₂O, and extracted with EtOAc. In Step 1.2, the reaction mixture is stirred for 2 h at 100° C. In Step 1.3, 4-chloro-2-isopropyl-pyridine (Step 8.1) is used. The reaction mixture is stirred for 3 h at 150° C., diluted with EtOAc/H₂O, and extracted with EtOAc. After drying and concentration of the organic phase, the residue is purified by silica gel column chromatography (Hex/EtOAc, 25:75).

Title compound: ESI-MS: 374.1 [M+H]⁺; $t_R$=1.99 min (System 1); TLC: $R_f$=0.10 (DCM/MeOH/NH$_3^{aq}$, 94:5:1).

Step 8.1: 4-Chloro-2-isopropyl-pyridine

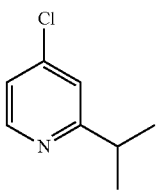

The title compound is prepared in analogy to the procedure described in Step 2.1 but using isopropylmagnesium chloride (2M in THF): ESI-MS: 156.0 [M+H]$^+$; TLC: R$_f$=0.32 (DCM).

EXAMPLE 9

(S)-Pyrrolidine-1,2-dicarboxylic acid 2-amide 1-{[5-(2-cyclobutyl-pyridin-4-yl)-thiazol-2-yl]-amide}

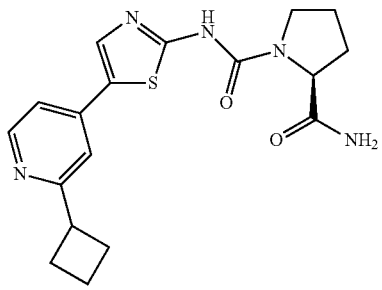 [SMILES: NC(=O)[C@@H]1CCCN1C(=O)Nc1ncc(-c2ccnc(C3CCC3)c2)s1]

The title compound is prepared in analogy to the procedure described in Example 1 but with the following modifications. In Example 1, the reaction mixture is stirred for 16 h at rt, diluted with DCM/H$_2$O and extracted with DCM. In Step 1.2, the reaction mixture is stirred for 2 h at 100° C. and the crude product is not purified. In Step 1.3, N-thiazol-2-yl-acetamide is used. The reaction mixture is stirred for 3 h at 120° C., quenched by dilution with EtOAc/H$_2$O, and extracted with EtOAc. After drying and concentration of the organic phase, the residue is purified by silica gel column chromatography (Hex/EtOAc, 2:3). In Step 1.5, the reaction mixture is stirred for 1 h at 80° C. and trituration in MeOH is not performed. In Step 1.7, In Step 1.7, 4-methoxy-3-buten-2-one (50 mmol) in THF (100 mL) is added to a cold (−78° C.) solution of LiHMDS (1M in THF, 100 mL) in THF (200 mL). After 30 min, cyclobutylcarbonyl chloride is added and the reaction mixture is allowed to reach it over 18 h.

Title compound: ESI-MS: 372.1 [M+H]$^+$; TLC: R$_f$=0.13 (DCM/MeOH/NH$_3$$^{aq}$, 91.5:7.5:1).

EXAMPLE 10

(S)-Pyrrolidine-1,2-dicarboxylic acid 2-amide 1-({5-[2-(1-methyl-cyclopropyl)-pyridin-4-yl]-thiazol-2-yl}-amide)

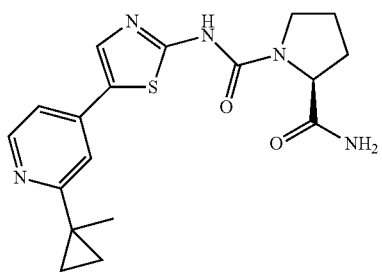 [SMILES: CC1(c2cc(-c3cnc(NC(=O)N4CCC[C@H]4C(N)=O)s3)ccn2)CC1]

The title compound is prepared in analogy to the procedure described in Example 1 but with the following modifications. In Step 1.1, the reaction mixture is stirred for 14 h at reflux. In Step 1.2, the reaction mixture is stirred for 1 h at 85° C. In Step 1.3, N-thiazol-2-yl-acetamide is used and the reaction mixture is stirred for 4 h at 120° C. In Step 1.5, trituration in MeOH is not performed. In Step 1.7, 1-methyl-cyclopropanecarbonyl chloride (Step 5.1) is used.

Title compound: ESI-MS: 372.1 [M+H]$^+$; TLC: R$_f$=0.43 (DCM/MeOH, 9:1).

EXAMPLE 11

(S)-Pyrrolidine-1,2-dicarboxylic acid 2-amide 1-({5-[2-(1-trifluoromethyl-cyclopropyl)-pyridin-4-yl]-thiazol-2-yl}-amide)

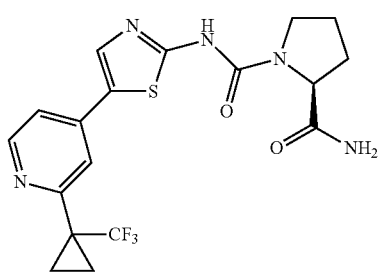 [SMILES: NC(=O)[C@@H]1CCCN1C(=O)Nc1ncc(-c2ccnc(C3(C(F)(F)F)CC3)c2)s1]

The title compound is prepared in analogy to the procedure described in Example 1 but with the following modifications. In Step 1.1, the reaction mixture is stirred for 14 h at reflux. In Step 1.3, N-thiazol-2-yl-acetamide is used. The reaction mixture is stirred for 2 h at 120° C. In Step 1.4, 1,2-dichloroethane (2.55 mL per mmol of pyridin-4-one) is used as the solvent. The reaction mixture is stirred for 1 h at 83° C. and extracted with EtOAc after being quenched. In Step 1.5, the reaction mixture is stirred for 1 h at 65° C. and trituration in MeOH is not performed. In Step 1.7, 1-trifluoromethyl-cyclopropanecarbonyl chloride (Step 11.1) is used.

Title compound: ESI-MS: 426.0 [M+H]$^+$; t$_R$=2.35 min (System 1); TLC: R$_f$=0.25 (DCM/MeOH, 9:1).

Step 11.1: 1-Trifluoromethyl-cyclopropanecarbonyl chloride

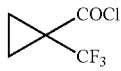

The title compound is prepared in analogy to the procedure described in Step 5.1 but using 1-trifluoromethyl-cyclopropanecarboxylic acid.

EXAMPLE 12

(S)-Pyrrolidine-1,2-dicarboxylic acid 2-amide 1-({5-[2-(2,2,2-trifluoro-1,1-dimethyl-ethyl)-pyridin-4-yl]-thiazol-2-yl}-amide)

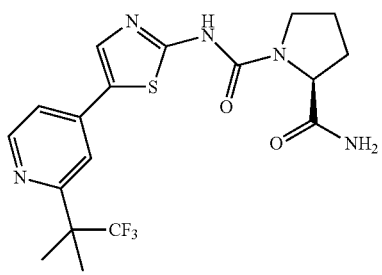 [SMILES: CC(C)(c1cc(-c2cnc(NC(=O)N3CCC[C@H]3C(N)=O)s2)ccn1)C(F)(F)F]

The title compound is prepared in analogy to the procedure described in Example 1 but with the following modifications. In Example 1, the reaction mixture is stirred for 5 h at rt. In Step 1.1, the reaction mixture is stirred for 14 h at reflux. In Step 1.2, the reaction mixture is stirred for 1 h at 85° C. and extracted with EtOAc after being quenched. In Step 1.3, N-thiazol-2-yl-acetamide is used. The reaction mixture is stirred for 2.5 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: ESI-MS: 428.0 [M+H]$^+$; $t_R$=2.75 min (System 1); TLC: R$_f$=0.21 (DCM/MeOH, 9:1).

Step 12.1: 3,3,3-Trifluoro-2,2-dimethyl-propionyl chloride

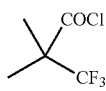

The title compound is prepared in analogy to the procedure described in Step 5.1 but using 3,3,3-trifluoro-2,2-dimethyl-propionic acid.

EXAMPLE 13

(S)-Pyrrolidine-1,2-dicarboxylic acid 2-amide 1-({5-[2-(1-trifluoromethyl-cyclobutyl)-pyridin-4-yl]-thiazol-2-yl}-amide)

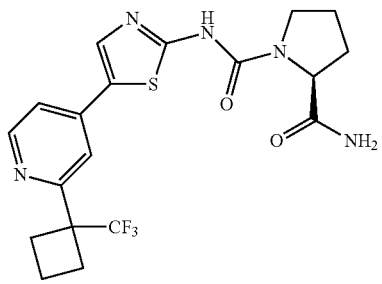 [SMILES: NC(=O)[C@@H]1CCCN1C(=O)Nc1ncc(-c2ccnc(C3(C(F)(F)F)CCC3)c2)s1]

The title compound is prepared in analogy to the procedure described in Example 1 but with the following modifications. In Example 1, the reaction mixture is stirred for 18 h at rt, quenched by dilution with DCM/H$_2$O and extracted with DCM. In Step 1.1, the reaction mixture is stirred for 1 h at reflux. In Step 1.2, the reaction mixture is stirred for 1 h at 100° C. and extracted with DCM after being quenched. In Step 1.3, N-thiazol-2-yl-acetamide is used. The reaction mixture is stirred for 5 h at 120° C., quenched by dilution with EtOAc/H$_2$O and extracted with EtOAc. In Step 1.4, 1,2-dichloroethane (2.26 mL per mmol of pyridin-4-one) is used as the solvent. The reaction mixture is stirred for 1 h at reflux and extracted with DCM after being quenched. In Step 1.5, the reaction mixture is stirred for 1 h at rt and trituration in MeOH is not performed. In Step 1.6, the reaction mixture is stirred for 18 h at rt. In Step 1.7, 4-methoxy-3-buten-2-one in THF is added to a cold (−78° C.) solution of LiHMDS in THF. After 30 min, 1-trifluoromethyl-cyclobutanecarbonyl chloride (Step 13.1) in THF is added. The reaction mixture is allowed to reach rt over 18 h and extracted with EtOAc after being quenched.

Title compound: ESI-MS: 440.0 [M+H]$^+$; $t_R$=2.68 min (System 1); TLC: R$_f$=0.08 (DCM/MeOH/NH$_3^{aq}$, 91.5:7.5:1).

Step 13.1: 1-Trifluoromethyl-cyclobutanecarbonyl chloride

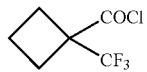

The title compound is prepared in analogy to the procedure described in Step 5.1 but using 1-trifluoromethyl-cyclobutanecarboxylic acid and stirring the reaction mixture for 2 h at reflux.

EXAMPLE 14

(S)-Pyrrolidine-1,2-dicarboxylic acid 2-amide 1-({4-methyl-5-[2-(1-trifluoromethyl-cyclopropyl)-pyridin-4-yl]-thiazol-2-yl}-amide)

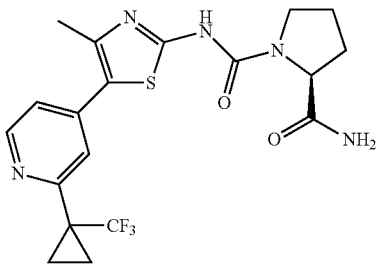 [SMILES: Cc1nc(NC(=O)N2CCC[C@H]2C(N)=O)sc1-c1ccnc(C2(C(F)(F)F)CC2)c1]

The title compound is prepared in analogy to the procedure described in Example 1 but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, the reaction mixture is stirred for 2 h at 120° C. In Step 1.4, 1,2-dichloroethane (2.55 mL per mmol of pyridin-4-one) is used as the solvent. The reaction mixture is stirred for 1 h at 83° C. and extracted with EtOAc after being quenched. In Step 1.5, the reaction mixture is stirred for 1 h at 65° C. and trituration in MeOH is not performed. In Step 1.7, 1-trifluoromethyl-cyclopropanecarbonyl chloride (Step 11.1) is used.

Title compound: ESI-MS: 440.0 [M+H]$^+$; $t_R$=2.65 min (System 1); TLC: $R_f$=0.36 DCM/MeOH, 9:1). $^1$H NMR (400 MHz, DMSO-d6) δ(ppm): 1.41 (s, 4H) 1.70-1.90 (m, 3H) 2.00-2.10 (m, 1H) 2.40 (s, 3H) 3.36-3.52 (m, 1H) 3.52-3.65 (m, 1H) 4.10-4.40 (m, 1H) 6.95 (br. s., 1H) 7.37 (d, 2H) 7.47 (s, 1H) 8.52 (d, 1H) 10.94 (br. s., 1H)

EXAMPLE 15

(S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide)

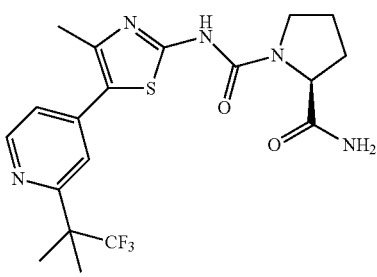 [SMILES: Cc1nc(NC(=O)N2CCC[C@H]2C(N)=O)sc1-c1ccnc(C(C)(C)C(F)(F)F)c1]

The title compound is prepared in analogy to the procedure described in Example 1 but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, the reaction mixture is stirred for 2.5 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: ESI-MS: 442.0 [M+H]$^+$; $t_R$=3.02 min (System 1); TLC: $R_f$=0.35 (DCM/MeOH, 9:1). $^1$H NMR (400 MHz, DMSO-d6) δ(ppm): 1.60 (s, 6H) 1.70-1.95 (m, 3H) 1.99-2.16 (m, 1H) 2.40 (s, 3H) 3.38-3.51 (m, 1H) 3.51-3.69 (m, 1H) 4.10-4.40 (m, 1H) 6.95 (br. s., 1H) 7.39 (d, 2H) 7.53 (s, 1H) 8.58 (d, 1H) 10.93 (br. s., 1H)

In an alternative procedure the title compound is prepared in analogy to the procedure described in Example 1 but with the following modifications: N,N-Dimethylacetamide is used instead of DMF and the mixture is stirred at 65° C. for 2 h. In Step 1.1, phenyl chloroformate (added slowly) is used instead of 1,1'-carbonyldiimidazole and the reaction is carried out in THF in the presence of N,N-diethyl-isopropylamine at room temperature (1.5 h). In Step 1.2, the reaction mixture is heated under stirring for 5 h under (reflux) and extracted with EtOAc after being quenched. In Step 1.3, the reaction mixture is stirred for 2 h at 100° C. In Step 1.4, the reaction is run in toluene using 1.1 equivalents of POBr$_3$ and 1.1 equivalents of tripropylamine and the mixture is stirred for 2 h at 80° C. and extracted with EtOAc after being quenched. In Step 1.5, the reaction mixture is stirred for 1 h at 65° C. and trituration in MeOH is not performed. In Step 1.6, toluene is used instead of benzene and the crude product is not purified. In Step 1.7, 3,3,3-trifluoro-2,2-dimethyl-propionyl chloride (Step 12.1) is used.

EXAMPLE 16

(S)-Pyrrolidine-1,2-dicarboxylic acid 2-amide 1-({4-methyl-5-[2-(1-trifluoromethyl-cyclobutyl)-pyridin-4-yl]-thiazol-2-yl}-amide)

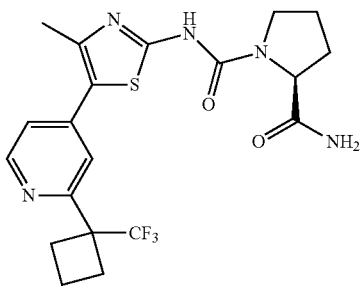 [SMILES: Cc1nc(NC(=O)N2CCC[C@H]2C(N)=O)sc1-c1ccnc(C2(C(F)(F)F)CCC2)c1]

The title compound is prepared in analogy to the procedure described in Example 1 but with the following modifications. In Example 1, the reaction mixture is stirred for 72 h at rt, quenched by dilution with DCM/H$_2$O and extracted with DCM. In Step 1.1, the reaction mixture is stirred for 1 h at reflux. In Step 1.2, the reaction mixture is stirred for 2 h at 100° C. and extracted with DCM after being quenched. In Step 1.3, the reaction mixture is stirred for 6 h at 120° C., quenched by dilution with EtOAc/H$_2$O, filtered through a pad of celite and extracted with EtOAc. In Step 1.4, 1,2-dichloroethane (2.26 mL per mmol of pyridin-4-one) is used as the solvent. The reaction mixture is stirred for 1 h at reflux and extracted with DCM after being quenched. In Step 1.5, the reaction mixture is stirred for 1 h at it and trituration in MeOH is not performed. In Step 1.6, the reaction mixture is stirred for 18 h at rt. In Step 1.7, 4-methoxy-3-buten-2-one in THF is added to a cold (−78° C.) solution of LiHMDS in THF. After 30 min, 1-trifluoromethyl-cyclobutanecarbonyl chloride (Step 13.1) in THF is added. The reaction mixture is allowed to reach it over 18 h and extracted with EtOAc after being quenched.

Title compound: ESI-MS: 454.1 [M+H]$^+$; $t_R$=2.90 min (System 1); TLC: $R_f$=0.22 (DCM/MeOH/NH$_3$$^{aq}$, 91.5:7.5:1).

EXAMPLE 17

(S)-Pyrrolidine-1,2-dicarboxylic acid 2-amide 1-({5-[2-(1-methyl-cyclobutyl)-pyridin-4-yl]-thiazol-2-yl}-amide)

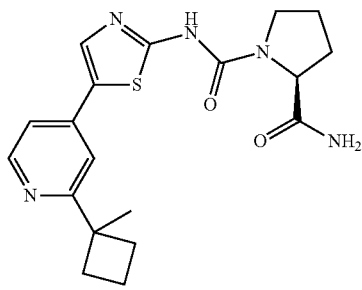 [SMILES: CC1(c2cc(-c3cnc(NC(=O)N4CCC[C@H]4C(N)=O)s3)ccn2)CCC1]

The title compound is prepared in analogy to the procedure described in Example 1 but with the following modifications. In Example 1, the reaction mixture is stirred for 24 h at rt, quenched by dilution with EtOAc/H$_2$O, and extracted with EtOAc. In Step 1.2, the reaction mixture is stirred for 2 h at 100° C. and extracted with DCM after being quenched. In Step 1.3, N-thiazol-2-yl-acetamide is used. The reaction mixture is stirred for 3 h at 100° C., diluted with EtOAc/H$_2$O, and extracted with EtOAc. After drying and concentration of the organic phase, the residue is purified by silica gel column chromatography (Hex/EtOAc, 25:75). In Step 1.5, the reaction mixture is stirred for 2 h at 80° C. and trituration in MeOH is not performed. In Step 1.7, 4-methoxy-3-buten-2-one in THF is added to a cold (−78° C.) solution of LiHMDS in THF. After 30 min, 1-methyl-cyclobutane chloride (Step 6.1) in THF is added and the reaction mixture is allowed to reach it over 18 h.

Title compound: ESI-MS: 386.1 [M+H]$^+$; $t_R$=2.32 min (System 1); TLC: $R_f$=0.05 (DCM/MeOH/NH$_3$$^{aq}$, 94:5:1).

EXAMPLE 18

(S)-Pyrrolidine-1,2-dicarboxylic acid 2-amide 1-({5-[2-(1-cyano-cyclopropyl)-pyridin-4-yl]-4-methyl-thiazol-2-yl}-amide)

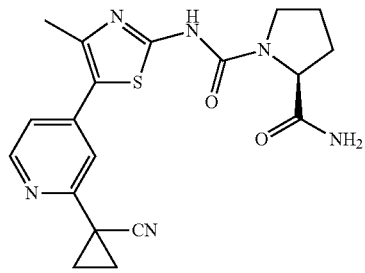 [SMILES: Cc1nc(NC(=O)N2CCC[C@H]2C(N)=O)sc1-c1ccnc(C2(C#N)CC2)c1]

The title compound is prepared in analogy to the procedure described in Example 1 but with the following modifications. In Example 1, the reaction mixture is stirred for 16 h at rt, quenched by dilution with EtOAc/H$_2$O, and extracted with EtOAc. In Step 1.1, 1-[4-(2-amino-4-methyl-thiazol-5-yl)-pyridin-2-yl]-cyclopropanecarbonitrile (Step 18.1) is used and the reaction mixture is stirred for 2 h at reflux.

Title compound: ESI-MS: 397.0 [M+H]$^+$; $t_R$=2.90 min (System 1); TLC: $R_f$=0.08 (DCM/MeOH/NH$_3$$^{aq}$, 94:5:1). $^1$H NMR (400 MHz, DMSO-d6) δ(ppm): 1.69-1.93 (m, 7H) 2.00-2.20 (m, 1H) 2.42 (s, 3H) 3.38-3.50 (m, 1H) 3.50-3.65 (m, 1H) 4.10-4.40 (m, 1H) 6.94 (br. s., 1H) 7.34 (dd, 1H) 7.37 (br. s., 1H) 7.47 (s, 1H) 8.47 (d, 1H)

Step 18.1: 1-[4-(2-Amino-4-methyl-thiazol-5-yl)-pyridin-2-yl]-cyclopropanecarbonitrile

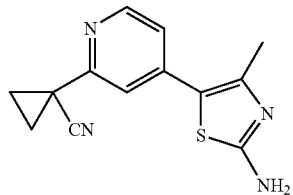 [SMILES: Cc1nc(N)sc1-c1ccnc(C2(C#N)CC2)c1]

A mixture of {5-[2-(1-cyano-cyclopropyl)-pyridin-4-yl]-4-methyl-thiazol-2-yl}-carbamic acid tert-butyl ester (Step 18.2) (295 mg), DCM (4 mL) and TFA (1 mL) is stirred for 2 h at rt and then concentrated. The residue is purified by silica gel column chromatography (DCM/MeOH/NH$_3$$^{aq}$, 94:5:1) to afford 182 mg of the title compound: ESI-MS: 257.1 [M+H]+; $t_R$=2.54 min (System 1); TLC: $R_f$=0.30 ((DCM/MeOH/NH$_3^{aq}$, 94:5:1).

Step 18.2: {5-[2-(1-Cyano-cyclopropyl)-pyridin-4-yl]-4-methyl-thiazol-2-yl}-carbamic acid tert-butyl ester

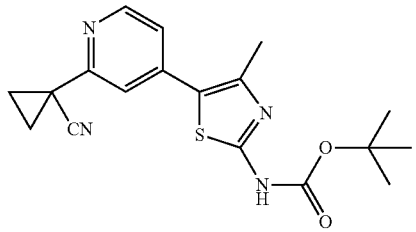 [SMILES: Cc1nc(NC(=O)OC(C)(C)C)sc1-c1ccnc(C2(C#N)CC2)c1]

The title compound is prepared in analogy to the procedure described in Step 1.3, but using 1-(4-bromo-pyridin-2-yl)-cyclopropanecarbonitrile (Step 18.3) and (4-methyl-thiazol-2-yl)-carbamic acid tert-butyl ester (Step 18.4). The reaction mixture is stirred for 2 h at 100° C., quenched by dilution with EtOAc/H$_2$O, and extracted with EtOAc. The crude product is purified by silica gel column chromatography (Hex/EtOAc, 1:1) to afford 122 mg of the title compound as a white solid: ESI-MS: 357.1 [M+H]+; $t_R$=4.86 min (System 1); TLC: $R_f$=0.29 (Hex/EtOAc, 1:1).

Step 18.3: 1-(4-Bromo-pyridin-2-yl)-cyclopropanecarbonitrile

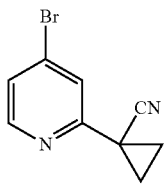

LiHMDS (1M in toluene, 17.6 mL, 17.6 mmol, 3.1 eq) is added dropwise to a cold (−5° C.) mixture of 4-bromo-2-fluoro-pyridine [Marsais, F. et al, Journal of Organic Chemistry, (1992), 57, 565-573] (1 g, 5.7 mmol), cyclopropanecarbonitrile (1.25 mL, 17 mmol, 3 eq), 4 Å molecular sieves and toluene (20 mL). The reaction mixture is allowed to warm to rt, stirred for 16 h, poured into H$_2$O and filtered. The filtrate is diluted with EtOAc/H$_2$O and extracted with EtOAc. The organic phase is washed with H$_2$O and brine, dried (Na$_2$SO$_4$), filtered and concentrated. The residue is purified by silica gel column chromatography (Hex/EtOAc, 9:1), to afford 620 mg of the title compound as a white solid: ESI-MS: 223.1/225.1 [M+H]+; $t_R$=4.22 min (System 1); TLC: $R_f$=0.25 (Hex/EtOAc, 9:1).

Step 18.4: (4-Methyl-thiazol-2-yl)-carbamic acid tert-butyl ester

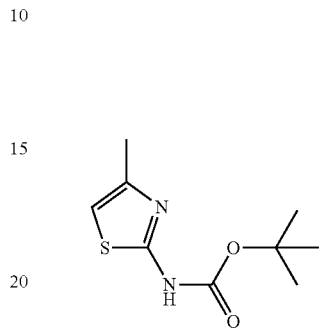

A solution of di-tert-butyl-dicarbonate (21 g, 96.5 mmol, 1.1 eq) in t-BuOH (50 mL) is added to a solution of 4-methyl-2-aminothiazole (10 g, 87.7 mmol) and DMAP (1.1 g, 8.8 mmol, 0.1 eq) in t-BuOH (50 mL). The reaction mixture is stirred for 72 h at rt and concentrated. The residue is diluted with EtOAc/H$_2$O and extracted with EtOAc. The organic phase is washed with H$_2$O and brine, dried (Na$_2$SO$_4$), filtered and concentrated. The residue is purified by silica gel column chromatography (DCM/MeOH, 98:2), to afford 15.2 g of the title compound as a white solid: ESI-MS: 215.1 [M+H]+; $t_R$=3.43 min (System 1); TLC: $R_f$=0.30 (DCM/MeOH, 98:2).

EXAMPLE 19

(S)-Pyrrolidine-1,2-dicarboxylic acid 2-amide 1-({5-[2-(1-cyano-cyclobutyl)-pyridin-4-yl]-4-methyl-thiazol-2-yl}-amide)

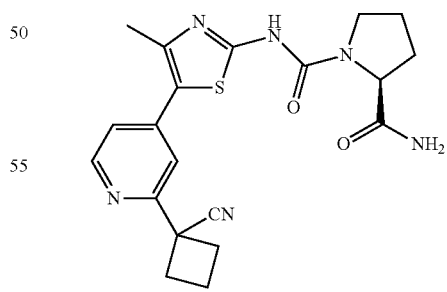

The title compound is prepared in analogy to the procedure described in Example 1 but with the following modifications. In Example 1, the reaction mixture is stirred for 6 h at rt. In Step 1.1, 1-[4-(2-amino-4-methyl-thiazol-5-yl)-pyridin-2-yl]-cyclobutanecarbonitrile (Step 19.1) is used and the reaction mixture is stirred for 3 h at reflux.

Title compound: ESI-MS: 411.1 [M+H]+; TLC: R_f=0.36 (DCM/MeOH, 9:1).

Step 19.1: 1-[4-(2-Amino-4-methyl-thiazol-5-O-pyridin-2-yl]-cyclobutanecarbonitrile

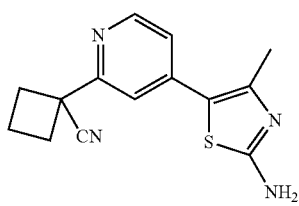 [SMILES: Cc1nc(N)sc1-c1ccnc(C2(C#N)CCC2)c1]

A mixture of {5-[2-(1-cyano-cyclobutyl)-pyridin-4-yl]-4-methyl-thiazol-2-yl}-carbamic acid tert-butyl ester (Step 19.2) (300 mg), DCM (5 mL) and TFA (1 mL) is stirred for 4 h at rt, quenched by addition of a saturated solution of NaHCO_3 (50 mL), and extracted with DCM (3×75 mL). The organic phase is washed with a saturated solution of NaHCO_3 (2×50 mL), dried (Na_2SO_4), filtered and concentrated. The residue is purified by silica gel column chromatography (DCM/MeOH, 1:0→96:4) to afford 181 mg of the title compound as a yellow solid: ESI-MS: 271.1 [M+H]+; t_R=2.48 min (System 1); TLC: R_f=0.45 (DCM/MeOH, 9:1).

Step 19.2: {5-[2-(1-Cyano-cyclobutyl)-pyridin-4-yl]-4-methyl-thiazol-2-yl}-carbamic acid tert-butyl ester

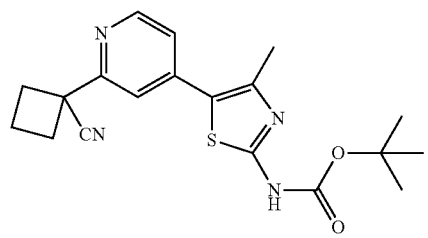 [SMILES: Cc1nc(NC(=O)OC(C)(C)C)sc1-c1ccnc(C2(C#N)CCC2)c1]

The title compound is prepared in analogy to the procedure described in Step 1.3, but using 1-(4-bromo-pyridin-2-yl)-cyclobutanecarbonitrile (Step 19.3) and (4-methyl-thiazol-2-yl)-carbamic acid tert-butyl ester (Step 18.4). The reaction mixture is stirred for 3 h at 100° C.

Title compound: ESI-MS: 371.1 [M+H]+; t_R=4.86 min (System 1); TLC: R_f=0.66 (Hex/EtOAc, 1:1).

Step 19.3: 1-(4-Bromo-pyridin-2-yl)-cyclobutanecarbonitrile

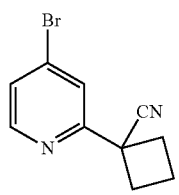 [SMILES: N#CC1(c2cc(Br)ccn2)CCC1]

LiHMDS (1M in toluene, 17.7 mL, 17.7 mmol, 3.1 eq) is added dropwise to a cold (−5° C.) solution of 4-bromo-2-fluoro-pyridine [Marsais, F. et al, Journal of Organic Chemistry, (1992), 57, 565-573] (1 g, 5.7 mmol) and cyclobutanecarbonitrile (1.39 g, 17.1 mmol, 3 eq) in toluene (20 mL). The reaction mixture is allowed to warm to rt, stirred for 5 h, quenched by addition of a saturated solution of NaHCO_3 (50 mL) and filtered through a pad of celite. The filtrate is extracted with EtOAc (3×75 mL). The organic phase is washed with a saturated solution of NaHCO_3 (2×50 mL), dried (Na_2SO_4), filtered and concentrated. The residue is purified by silica gel column chromatography (Hex/EtOAc, 1:0→95:5) to afford 933 mg of the title compound as a yellow oil: ESI-MS: 237.0/239.0 [M+H]+; t_R=4.27 min (System 1); TLC: R_f=0.30 (Hex/EtOAc, 9:1).

EXAMPLE 20

(S)-Pyrrolidine-1,2-dicarboxylic acid 2-amide 1-({5-[2-(1-carbamoyl-cyclobutyl)-pyridin-4-yl]-4-methyl-thiazol-2-yl}-amide)

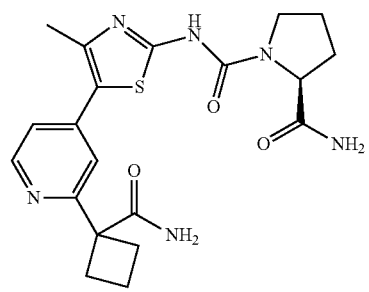 [SMILES: Cc1nc(NC(=O)N2CCC[C@H]2C(N)=O)sc1-c1ccnc(C2(C(N)=O)CCC2)c1]

The title compound is prepared in analogy to the procedure described in Example 1 but with the following modifications. In Example 1, the reaction mixture is stirred for 3 h at rt. In Step 1.1, 1-[4-(2-amino-4-methyl-thiazol-5-yl)-pyridin-2-yl]-cyclobutanecarboxylic acid amide (Step 20.1) is used and the reaction mixture is stirred for 12 h at reflux.

Title compound: ESI-MS: 429.1 [M+H]+; t_R=2.90 min (System 1); TLC: R_f=0.11 (DCM/MeOH, 9:1).

Step 20.1: 1-[4-(2-Amino-4-methyl-thiazol-5-O-pyridin-2-yl]-cyclobutanecarboxylic acid amide

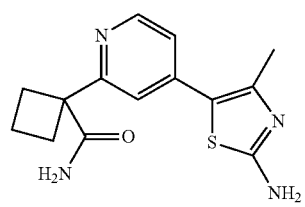 [SMILES: Cc1nc(N)sc1-c1ccnc(C2(C(N)=O)CCC2)c1]

A mixture of {5-[2-(1-cyano-cyclobutyl)-pyridin-4-yl]-4-methyl-thiazol-2-yl}-carbamic acid tert-butyl ester (Step 19.2) (640 mg, 1.73 mmol) and concentrated sulfuric acid is stirred for 40 min at 0° C., allowed to warm to rt, stirred for 1 h, quenched by addition of a saturated solution of NaHCO_3 (50 mL) and extracted with DCM (3×75 mL). The organic phase is washed with a saturated solution of NaHCO_3 (2×50 mL), dried (Na_2SO_4), filtered and concentrated. The residue is purified by silica gel column chromatography (DCM/

MeOH/NH$_3$$^{aq}$, 99:0:1→93:6:1) to afford 35 mg of the title compound as a yellow solid: ESI-MS: 289.1 [M+H]$^+$; TLC: R$_f$=0.32 (DCM/MeOH, 9:1).

EXAMPLE 21

(S)-Pyrrolidine-1,2-dicarboxylic acid 2-amide 1-({5-[2-(2-dimethylamino-1,1-dimethyl-ethyl)-pyridin-4-yl]-4-methyl-thiazol-2-yl}-amide)

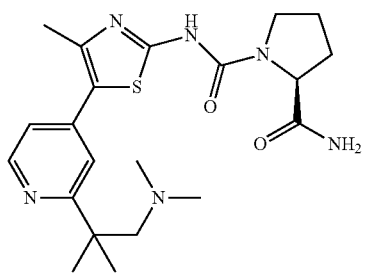 [SMILES: Cc1nc(NC(=O)N2CCC[C@H]2C(N)=O)sc1-c1ccnc(C(C)(C)CN(C)C)c1]

The title compound is prepared in analogy to the procedure described in Example 1 but with the following modifications. In Step 1.1, 5-[2-(2-dimethylamino-1,1-dimethyl-ethyl)-pyridin-4-yl]-4-methyl-thiazol-2-ylamine (Step 21.1) is used and the reaction mixture is stirred for 14 h at reflux.

Title compound: ESI-MS: 431.1 [M+H]$^+$; TLC: R$_f$=0.12 (DCM/MeOH, 9:1).

Step 21.1: 5-[2-(2-Dimethylamino-1,1-dimethyl-ethyl)-pyridin-4-yl]-4-methyl-thiazol-2-ylamine

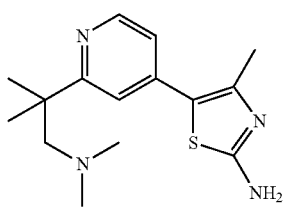 [SMILES: Cc1nc(N)sc1-c1ccnc(C(C)(C)CN(C)C)c1]

The title compound is prepared in analogy to the procedure described in Step 19.1 but using {5-[2-(2-dimethylamino-1,1-dimethyl-ethyl)-pyridin-4-yl]-4-methyl-thiazol-2-yl}-carbamic acid tert-butyl ester (Step 21.2) and stirring the reaction mixture for 2 h at rt. Title compound: ESI-MS: 291.1 [M+H]$^+$; t$_R$=2.48 min (System 1); TLC: R$_f$=0.11 (DCM/MeOH, 9:1).

Step 21.2: {5-[2-(2-Dimethylamino-1,1-dimethyl-ethyl)-pyridin-4-yl]-4-methyl-thiazol-2-yl}-carbamic acid tert-butyl ester

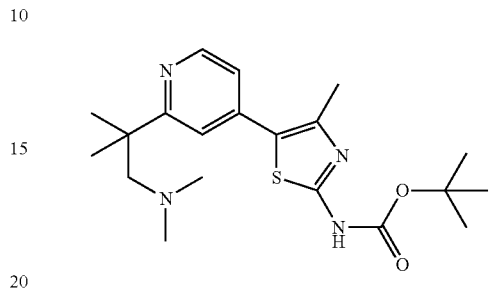

Formaldehyde (36% in H$_2$O, 0.144 mL, 1.87 mmol, 2 eq) is added to a mixture of {5-[2-(2-amino-1,1-dimethyl-ethyl)-pyridin-4-yl]-4-methyl-thiazol-2-yl}-carbamic acid tert-butyl ester (Step 21.3) (0.34 g, 0.94 mmol) and sodium acetoxyborohydride (0.6 g, 2.82 mmol, 3 eq) in 1,2-dichloroetane (10 mL). The reaction mixture is stirred for 1 h at it and concentrated. The residue is purified by silica gel column chromatography (DCM/MeOH/NH$_3$$^{aq}$, 99:0:1→97:2:1) to afford 0.222 g of the title compound as a white solid: ESI-MS: 391.2 [M+H]$^+$; t$_R$=4.27 min (System 1); TLC: R$_f$=0.15 (DCM/MeOH, 9:1).

Step 21.3: {5-[2-(2-Amino-1,1-dimethyl-ethyl)-pyridin-4-yl]-4-methyl-thiazol-2-yl}-carbamic acid tert-butyl ester

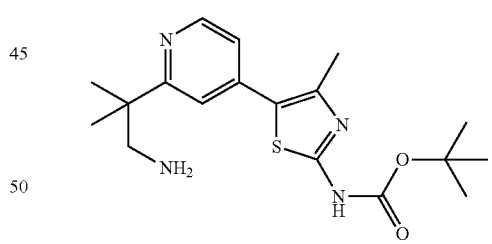

LiAlH$_4$ (1M in THF, 3.06 mL, 3.06 mmol, 1.5 eq) is added to a solution of {5-[2-(cyano-dimethyl-methyl)-pyridin-4-yl]-4-methyl-thiazol-2-yl}-carbamic acid tert-butyl ester (Step 21.4) (0.73 g, 2.04 mmol) in THF (10 mL), under an argon atmosphere. The reaction mixture is stirred for 2 h at rt, quenched by addition of H$_2$O (20 mL) and extracted with EtOAc (2×75 mL). The organic phase is washed with a saturated solution of NaHCO$_3$ (2×50 mL), dried (Na$_2$SO$_4$), filtered and concentrated. The residue is purified by silica gel column chromatography (DCM/MeOH/NH$_3$$^{aq}$, 99:0:1→94:

5:1) to afford 318 mg of the title compound as a brown solid: ESI-MS: 363.1 [M+H]$^+$; TLC: R$_f$=0.11 (DCM/MeOH, 9:1).

Step 21.4: {5-[2-(Cyano-dimethyl-methyl)-pyridin-4-yl]-4-methyl-thiazol-2-yl}-carbamic acid tert-butyl ester

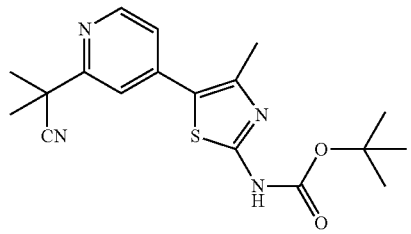 [SMILES: Cc1nc(NC(=O)OC(C)(C)C)sc1-c1ccnc(C(C)(C)C#N)c1]

The title compound is prepared in analogy to the procedure described in Step 1.3, but using 2-(4-iodo-pyridin-2-yl)-2-methyl-propionitrile (Step 21.5) and (4-methyl-thiazol-2-yl)-carbamic acid tert-butyl ester (Step 18.4). The reaction mixture is stirred for 3 h at 100° C. Title compound: ESI-MS: 359.1 [M+H]$^+$; TLC: R$_f$=0.47 (Hex/EtOAc, 1:1).

Step 21.5: 2-(4-Iodo-pyridin-2-yl)-2-methyl-propionitrile

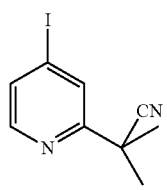

The title compound is prepared in analogy to the procedure described in Step 19.3, but using 2-fluoro-4-iodopyridine. Title compound: ESI-MS: 273.0 [M+H]$^+$; t$_R$=4.22 min (System 1); TLC: R$_f$=0.36 (Hex/EtOAc, 9:1).

EXAMPLE 22

(S)-Pyrrolidine-1,2-dicarboxylic acid 2-amide 1-{[5-(2-diethylamino-pyridin-4-yl)-4-methyl-thiazol-2-yl]-amide}

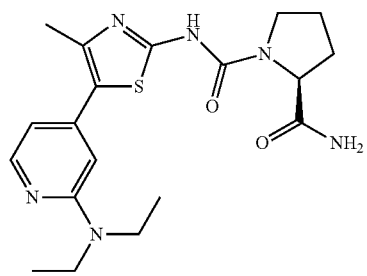 [SMILES: CCN(CC)c1cc(-c2sc(NC(=O)N3CCC[C@H]3C(N)=O)nc2C)ccn1]

The title compound is prepared in analogy to the procedure described in Example 1 but with the following modifications. In Example 1, the reaction mixture is stirred for 18 h at rt, quenched by dilution with DCM/H$_2$O and extracted with DCM. In Step 1.1, the reaction mixture is stirred for 1 h at reflux. In Step 1.2, the reaction mixture is stirred for 1 h at 100° C. and extracted with DCM after being quenched. In Step 1.3, diethyl-(4-iodo-pyridin-2-yl)-amine (Step 22.1) is used. The reaction mixture is stirred for 16 h at 120° C., quenched by dilution with EtOAc/H$_2$O, filtered through a pad of celite and extracted with EtOAc.

Title compound: ESI-MS: 403.2 [M+H]$^+$; t$_R$=2.38 min (System 1); TLC: R$_f$=0.10 (DCM/MeOH/NH$_3$$^{aq}$, 91.5:7.5:1).

Step 22.1: Diethyl-(4-iodo-pyridin-2-yl)-amine

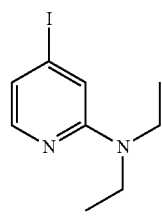

A mixture of 2-fluoro-4-iodopyridine (2 g, 8.97 mmol), diethyl amine (2.77 ml, 26.9 mmol, 3 eq) and K$_2$CO$_3$ (2.48 g, 17.94 mmol, 2 eq) in DMF (20 mL) is stirred for 18 h at 100° C., allowed to cool to rt, diluted with EtOAc/H$_2$O and extracted with EtOAc. The organic phase is washed with H$_2$O and brine, dried (Na$_2$SO$_4$), filtered and concentrated. The residue purified by silica gel column chromatography (Hex/Et$_2$O, 98:2) to afford 2.3 g of the title compound as a yellow oil: ESI-MS: 277.1 [M+H]$^+$; TLC: R$_f$=0.52 (Hex/Et$_2$O, 98:2).

EXAMPLE 23

(S)-Pyrrolidine-1,2-dicarboxylic acid 2-amide 1-{[5-(2-diethylamino-pyridin-4-yl)-thiazol-2-yl]amide}

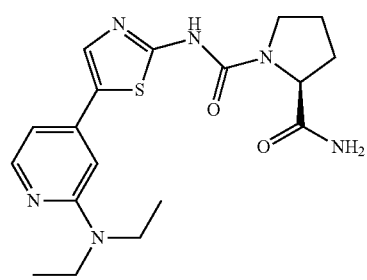 [SMILES: CCN(CC)c1cc(-c2cnc(NC(=O)N3CCC[C@H]3C(N)=O)s2)ccn1]

The title compound is prepared in analogy to the procedure described in Example 1 but with the following modifications. In Example 1, the reaction mixture is stirred for 18 h at rt, quenched by dilution with DCM/H$_2$O and extracted with DCM. In Step 1.1, the reaction mixture is stirred for 1 h at reflux. In Step 1.2, the reaction mixture is stirred for 1 h at 100° C. and extracted with DCM after being quenched. In Step 1.3, diethyl-(4-iodo-pyridin-2-yl)-amine (Step 22.1) and N-thiazol-2-yl-acetamide are used. The reaction mixture is stirred for 5 h at 120° C., quenched by dilution with EtOAc/H$_2$O, filtered through a pad of celite and extracted with EtOAc.

Title compound: ESI-MS: 389.2 [M+H]⁺; $t_R$=2.28 min (System 1); TLC: $R_f$=0.34 (DCM/MeOH/NH₃$^{aq}$, 91.5:7.5:1).

EXAMPLE 24

(S)-Pyrrolidine-1,2-dicarboxylic acid 2-amide 1-{[5-(3-tert-butyl-3H-benzoimidazol-5-yl)-thiazol-2-yl]-amide}

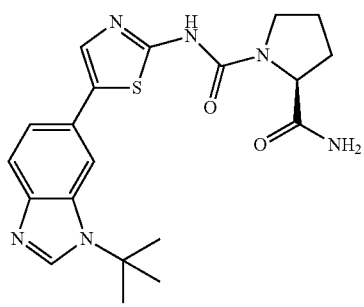 [SMILES: CC(C)(C)n1cnc2ccc(-c3cnc(NC(=O)N4CCC[C@H]4C(N)=O)s3)cc21]

The title compound is prepared in analogy to the procedure described in Example 1 but with the following modifications. In Example 1, the reaction mixture is stirred for 5 h at rt. In Step 1.1, the reaction mixture is stirred for 14 h at reflux. In Step 1.2, the reaction mixture is stirred for 1 h at 85° C. and extracted with EtOAc after being quenched. In Step 1.3, 6-bromo-1-tert-butyl-1H-benzoimidazole (Step 24.1) and N-thiazol-2-yl-acetamide are used. The reaction mixture is stirred for 7 h at 120° C.

Title compound: ESI-MS: 413.2 [M+H]⁺; $t_R$=2.29 min (System 1); TLC: $R_f$=0.45 (DCM/MeOH, 9:1).

Step 24.1: 6-Bromo-1-tert-butyl-1H-benzoimidazole

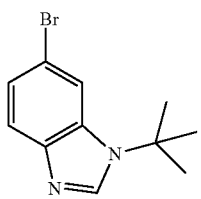

A mixture of 4-bromo-N*2*-tert-butyl-benzene-1,2-diamine (Step 24.2) (2.14 g, 8.80 mmol) and triethylortoformate (14.7 mL, 88 mmol) is stirred for 1 h at 148° C., allowed to cool and concentrated. The residue purified by silica gel column chromatography (DCM/MeOH, 1:0→99:1) to afford 1.74 g of the title compound as a white solid: ESI-MS: 253.0/255.0 [M+H]⁺; $t_R$=2.88 min (System 1); TLC: $R_f$=0.54 (DCM/MeOH, 9:1).

Step 24.2:
4-Bromo-N*2*-tert-butyl-benzene-1,2-diamine

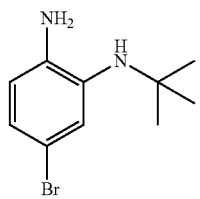

A suspension of (5-bromo-2-nitro-phenyl)-tert-butyl-amine (Step 24.3) (6 g, 21.97 mmol) and Raney nickel (2 g) in MeOH/THF (1:1 v/v, 600 mL) is stirred for 9 h at rt, under a hydrogen atmosphere. The reaction mixture is filtered through a pad of celite and concentrated. The residue purified by silica gel column chromatography (Hex/EtOAc, 97:3→3:1) to afford 4.4 g of the title compound as a black oil: ESI-MS: 243.0/245.0 [M+H]⁺; $t_R$=2.75 min (System 1); TLC: $R_f$=0.89 (Hex/EtOAc, 1:1).

Step 24.3:
(5-Bromo-2-nitro-phenyl)-tert-butyl-amine

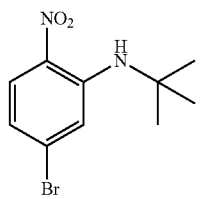

A mixture of 4-bromo-2-fluoro-nitrobenzene (4 g, 18.2 mmol) and tert-butylamine (4.78 mL, 45.5 mmol, 2.5 eq) in EtOH (80 mL) is stirred for 15 h at 85° C., allowed to cool and concentrated. The residue purified by silica gel column chromatography (Hex/EtOAc, 1:0→99:1) to afford 4.8 g of the title compound as an orange solid: ESI-MS: 273.0/275.0 [M+H]$^+$; $t_R$=5.68 min (System 1); TLC: $R_f$=0.49 (Hex/EtOAc, 9:1).

EXAMPLE 25

(S)-Pyrrolidine-1,2-dicarboxylic acid 2-amide 1-{[5-(3-tert-butyl-2-methyl-3H-benzoimidazol-5-yl)-thiazol-2-yl]-amide}

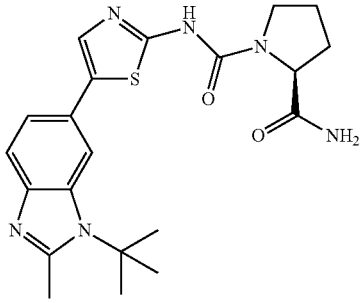 [SMILES: Cc1nc2ccc(-c3cnc(NC(=O)N4CCC[C@H]4C(N)=O)s3)cc2n1C(C)(C)C]

The title compound is prepared in analogy to the procedure described in Example 1 but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, 6-bromo-1-tert-butyl-2-methyl-1H-benzoimidazole (Step 25.1) and N-thiazol-2-yl-acetamide are used. The reaction mixture is stirred for 5 h at 120° C.

Title compound: ESI-MS: 427.2 [M+H]$^+$; $t_R$=2.37 min (System 1); TLC: $R_f$=0.38 (DCM/MeOH, 9:1).

Step 25.1: 6-Bromo-1-tert-butyl-2-methyl-1H-benzoimidazole

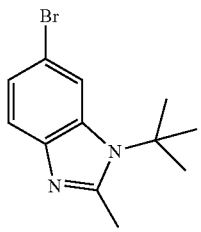

A mixture of 6-bromo-1-tert-butyl-2-ethoxymethyl-2-methyl-2,3-dihydro-1H-benzoimidazole (Step 25.2) (2.04 g, 6.51 mmol) and TFA (10 ml) is stirred at it overnight, quenched by addition of a saturated solution of NaHCO$_3$ (100 mL) and extracted with EtOAc (2×150 mL). The organic phase is washed with a saturated solution of NaHCO$_3$ (2×50 mL), dried (Na$_2$SO$_4$), filtered and concentrated. The residue purified by silica gel column chromatography (DCM/MeOH, 1:0→98:2) to afford 1.05 g of the title compound as a white solid: ESI-MS: 267.0/269.0 [M+H]$^+$; $t_R$=2.99 min (System 1); TLC: $R_f$=0.58 (DCM/MeOH, 9:1).

Step 25.2: 6-Bromo-1-tert-butyl-2-ethoxymethyl-2-methyl-2,3-dihydro-1H-benzoimidazole

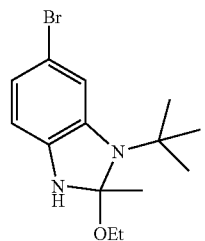 [SMILES: CCOC1(C)Nc2ccc(Br)cc2N1C(C)(C)C]

A mixture of 4-bromo-N*2*-tert-butyl-benzene-1,2-diamine (Step 24.2) (2.14 g, 8.80 mmol) and triethylortoacetate (16.2 mL, 88 mmol, 10 eq) is stirred for 1 h at 142° C., allowed to cool and concentrated. The residue purified by silica gel column chromatography (Hex/EtOAc, 1:0→95:5) to afford 2.04 g of the title compound as a purple oil: ESI-MS: 313.0/315.0 [M+H]$^+$; TLC: $R_f$=0.67 (Hex/EtOAc, 9:1).

EXAMPLE 26

(S)-Pyrrolidine-1,2-dicarboxylic acid 2-amide 1-{[5-(3-ethyl-3H-benzoimidazol-5-yl)-4-methyl-thiazol-2-yl]-amide}

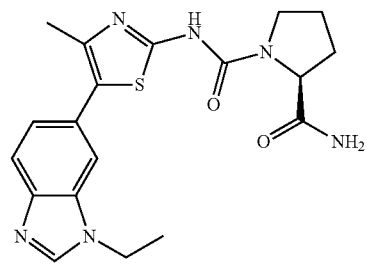 [SMILES: CCn1cnc2ccc(-c3sc(NC(=O)N4CCC[C@H]4C(N)=O)nc3C)cc21]

The title compound is prepared in analogy to the procedure described in Example 1 but with the following modifications. In Step 1.1, the reaction mixture is stirred for 15 h at reflux. In Step 1.2, the reaction mixture is stirred for 3 h at 85° C. and extracted with EtOAc after being quenched. In Step 1.3, 6-bromo-1-ethyl-1H-benzoimidazole (Step 26.1) and N-thiazol-2-yl-acetamide are used. The reaction mixture is stirred for 14 h at 120° C.

Title compound: ESI-MS: 399.1 [M+H]$^+$; $t_R$=1.73 min (System 1); TLC: R$_f$=0.25 (DCM/MeOH, 9:1).

Step 26.1: 6-Bromo-1-ethyl-1H-benzoimidazole

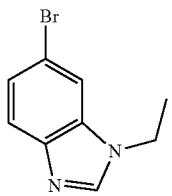

A mixture of 4-bromo-N*2*-ethyl-benzene-1,2-diamine (Step 26.2) (2 g, 9.3 mmol) and triethylortoformate (15.5 mL, 93 mmol, 10 eq) is stirred for 1 h at 148° C., allowed to cool and concentrated. The residue purified by silica gel column chromatography (DCM/MeOH, 1:0→98:2) to afford 2.05 g of the title compound as a white solid: ESI-MS: 225.1/227.1 [M+H]$^+$; $t_R$=2.31 min (System 1); TLC: R$_f$=0.58 (DCM/MeOH, 9:1).

Step 26.2:
4-Bromo-N*2*-ethyl-benzene-1,2-diamine

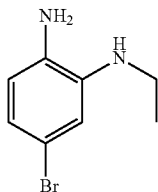

A suspension of (5-bromo-2-nitro-phenyl)-ethyl-amine (Step 26.3) (6 g, 24.48 mmol) and Raney nickel (2 g) in MeOH/THF (1:1 v/v, 600 mL) is stirred for 9 h at rt, under a hydrogen atmosphere. The reaction mixture is filtered through a pad of celite and concentrated. The residue purified by silica gel column chromatography (Hex/EtOAc, 95:5→85:15) to afford 4.51 g of the title compound as a black oil: ESI-MS: 213.1/215.1 [M–H]$^-$; $t_R$=2.53 min (System 1); TLC: R$_f$=0.57 (Hex/EtOAc, 1:1).

Step 26.3: (5-Bromo-2-nitro-phenyl)-ethyl-amine

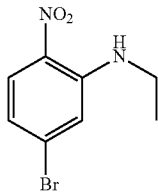

A mixture of 4-bromo-2-fluoro-nitrobenzene (6 g, 27.3 mmol), methylamine (2M in MeOH, 34.1 mL, 68.2 mmol, 2.5 eq) and EtOH (80 mL) is stirred for 15 h at 85° C., allowed to cool and concentrated. The residue purified by trituration to afford 6 g of the title compound as an yellow solid: $t_R$=5.13 min (System 1).

EXAMPLE 27

(S)-Pyrrolidine-1,2-dicarboxylic acid 2-amide 1-[(5-{2-[1-(4-methoxy-phenyl)-1-methyl-ethyl]-pyridin-4-yl}-4-methyl-thiazol-2-yl)-amide]

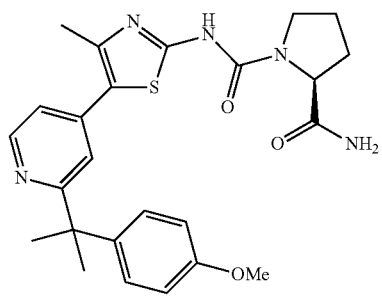 [SMILES: COc1ccc(C(C)(C)c2cc(-c3sc(NC(=O)N4CCC[C@H]4C(N)=O)nc3C)ccn2)cc1]

The title compound is prepared in analogy to the procedure described in Example 1 but with the following modifications. In Example 1, the reaction mixture is stirred for 24 h at rt, quenched by dilution with EtOAc/H$_2$O. In Step 1.2, the reaction mixture is stirred for 2 h at 100° C. and extracted with DCM after being quenched. In Step 1.3, the reaction mixture is stirred for 3 h at 100° C., quenched by dilution with EtOAc/H$_2$O and extracted with EtOAc. In Step 1.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 1.5, the reaction mixture is stirred for 23 h at 80° C. and trituration in MeOH is not performed. In Step 1.6, the reaction mixture is stirred for 21 h at rt. In Step 1.7, 4-methoxy-3-buten-2-one in THF is added to a cold (–78° C.) solution of LiHMDS in THF. After 30 min, 2-(4-methoxyphenyl)-2-methyl-propionyl chloride (Step 27.1) in THF is added and the reaction mixture is allowed to reach it over 16 h.

Title compound: ESI-MS: 480.0 [M+H]$^+$; $t_R$=3.05 min (System 1); TLC: R$_f$=0.13 (DCM/MeOH/NH$_3$$^{aq}$, 94:5:1).

Step 27.1:
2-(4-Methoxy-phenyl)-2-methyl-propionyl chloride

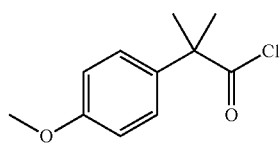

The title compound is prepared in analogy to the procedure described in Step 5.1 but using 2-(4-methoxy-phenyl)-2-methyl-propionic acid and stirring the reaction mixture for 3 h at reflux.

EXAMPLE 28

(S)-Pyrrolidine-1,2-dicarboxylic acid 2-amide 1-[(5-{2-[1-(4-methoxy-phenyl)-1-methyl-ethyl]-pyridin-4-yl}-thiazol-2-yl)-amide]

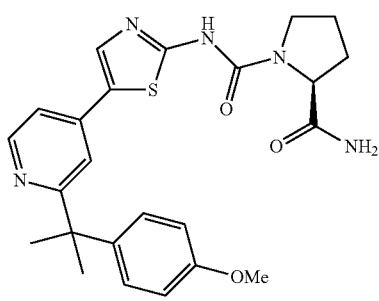 [SMILES: COc1ccc(C(C)(C)c2cc(-c3cnc(NC(=O)N4CCC[C@H]4C(N)=O)s3)ccn2)cc1]

The title compound is prepared in analogy to the procedure described in Example 1 but with the following modifications. In Example 1, the reaction mixture is stirred for 16 h at rt, quenched by dilution with EtOAc/H$_2$O. In Step 1.2, the reaction mixture is stirred for 2 h at 100° C. and extracted with DCM after being quenched. In Step 1.3, N-thiazol-2-yl-acetamide is used. The reaction mixture is stirred for 5 h at 100° C., quenched by dilution with EtOAc/H$_2$O and extracted with EtOAc. In Step 1.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 1.5, the reaction mixture is stirred for 23 h at 80° C. and trituration in MeOH is not performed. In Step 1.6, the reaction mixture is stirred for 21 h at rt. In Step 1.7, 4-methoxy-3-buten-2-one in THF is added to a cold (−78° C.) solution of LiHMDS in THF. After 30 min, 2-(4-methoxy-phenyl)-2-methyl-propionyl chloride (Step 27.1) in THF is added and the reaction mixture is allowed to reach rt over 16 h.

Title compound: ESI-MS: 466.1 [M+H]$^+$; $t_R$=2.91 min (System 1); TLC: R$_f$=0.23 (DCM/MeOH/NH$_3{}^{aq}$, 94:5:1).

EXAMPLE 29

(S)-Pyrrolidine-1,2-dicarboxylic acid 2-amide 1-[(5-{2-[1-(4-methoxy-phenyl)-cyclopropyl]-pyridin-4-yl}-4-methyl-thiazol-2-yl)-amide]

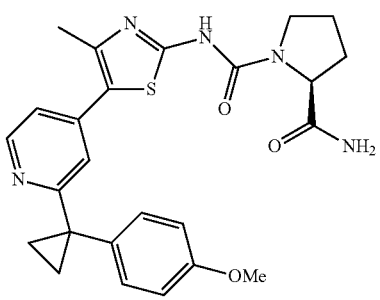 [SMILES: COc1ccc(C2(c3cc(-c4sc(NC(=O)N5CCC[C@H]5C(N)=O)nc4C)ccn3)CC2)cc1]

The title compound is prepared in analogy to the procedure described in Example 1 but with the following modifications. In Example 1, the reaction mixture is stirred for 21 h at rt, quenched by dilution with EtOAc/H$_2$O. In Step 1.2, the reaction mixture is stirred for 3 h at 100° C. and extracted with DCM after being quenched. In Step 1.3, the reaction mixture is stirred for 6 h at 100° C., quenched by dilution with EtOAc/H$_2$O and extracted with EtOAc. In Step 1.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 1.5, the reaction mixture is stirred for 18 h at 80° C. and trituration in MeOH is not performed. In Step 1.6, the reaction mixture is stirred for 18 h at rt. In Step 1.7, 4-methoxy-3-buten-2-one in THF is added to a cold (−78° C.) solution of LiHMDS in THF. After 30 min, 1-(4-methoxy-phenyl)-cyclopropanecarbonyl chloride (Step 29.1) in THF is added and the reaction mixture is allowed to reach rt over 16 h.

Title compound: ESI-MS: 478.1 [M+H]$^+$; $t_R$=2.65 min (System 1); TLC: R$_f$=0.09 (DCM/MeOH/NH$_3{}^{aq}$, 94:5:1).

Step 29.1:
1-(4-Methoxy-phenyl)-cyclopropanecarbonyl chloride

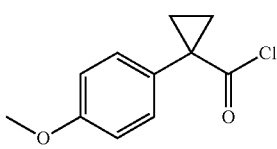

The title compound is prepared in analogy to the procedure described in Step 5.1 but using 1-(4-methoxy-phenyl)-cyclopropylcarboxylic acid and stirring the reaction mixture for 3 h at reflux.

EXAMPLE 30

(S)-Pyrrolidine-1,2-dicarboxylic acid 2-amide 1-[(5-[2-O-(4-methoxy-phenyl)-cyclopropyl]-pyridin-4-yl)-thiazol-2-yl)-amide]

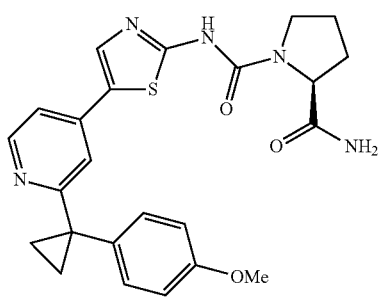 [SMILES: COc1ccc(C2(c3cc(-c4cnc(NC(=O)N5CCC[C@H]5C(N)=O)s4)ccn3)CC2)cc1]

The title compound is prepared in analogy to the procedure described in Example 1 but with the following modifications. In Example 1, the reaction mixture is stirred for 16 h at rt, quenched by dilution with EtOAc/H$_2$O. In Step 1.2, the reaction mixture is stirred for 3 h at 100° C. and extracted with DCM after being quenched. In Step 1.3, N-thiazol-2-yl-acetamide is used. The reaction mixture is stirred for 28 h at 100° C., quenched by dilution with EtOAc/H$_2$O and extracted with EtOAc. In Step 1.4, 1,2-dichloroethane (4.3 mL per mmol of pyridin-4-one) is used as the solvent. The reaction mixture is stirred for 1 h at reflux, poured into a saturated solution of NaHCO$_3$ and extracted with DCM. In Step 1.5, the reaction mixture is stirred for 18 h at 80° C. and trituration in MeOH is not performed. In Step 1.6, the reaction mixture is stirred for 18 h at rt. In Step 1.7, 4-methoxy-3-buten-2-one in THF is added to a cold (−78° C.) solution of LiHMDS in THF. After 30 min, 1-(4-methoxy-phenyl)-cyclopropanecarbonyl chloride (Step 29.1) in THF is added and the reaction mixture is allowed to reach rt over 16 h.

Title compound: ESI-MS: 464.1 [M+H]$^+$; t$_R$=2.90 min (System 1); TLC: R$_f$=0.06 (DCM/MeOH/NH$_3^{aq}$, 94:5:1).

EXAMPLE 31

(S)-Pyrrolidine-1,2-dicarboxylic acid 2-amide 1-{[5-(2-{1-[4-(3-dimethylamino-propoxy)-phenyl]-1-methyl-ethyl}-pyridin-4-yl)-4-methyl-thiazol-2-yl]-amide}

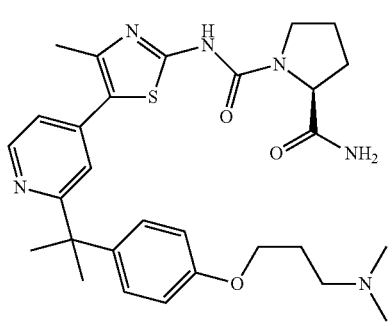 [SMILES: Cc1nc(NC(=O)N2CCC[C@H]2C(N)=O)sc1-c1ccnc(C(C)(C)c2ccc(OCCCN(C)C)cc2)c1]

The title compound is prepared in analogy to the procedure described in Example 1 but with the following modifications. In Example 1, the reaction mixture is stirred for 18 h at rt, quenched by dilution with EtOAc/H$_2$O. In Step 1.2, the reaction mixture is stirred for 7 h at 100° C. and extracted with DCM after being quenched. In Step 1.3, (3-{4-[1-(4-bromo-pyridin-2-yl)-1-methyl-ethyl]-phenoxy}-propyl)-dimethyl-amine (Step 31.1) is used. The reaction mixture is stirred for 2 h at 120° C., quenched by dilution with EtOAc/H$_2$O and extracted with EtOAc.

Title compound: ESI-MS: 551.1 [M+H]$^+$; t$_R$=2.38 min (System 1); TLC: R$_f$=0.05 (DCM/MeOH/NH$_3^{aq}$, 94:5:1).

Step 31.1: (3-{4-[1-(4-Bromo-pyridin-2-yl)-1-methyl-ethyl]-phenoxy}-propyl)-dimethyl-amine

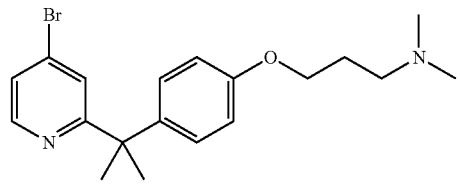 [SMILES: CN(C)CCCOc1ccc(C(C)(C)c2cc(Br)ccn2)cc1]

Sodium hydroxyde (pellets are finely grinded, 0.488 g, 12.2 mmol, 5 eq) is added to a solution of 4-[1-(4-bromo-pyridin-2-yl)-1-methyl-ethyl]-phenol (Step 31.2) (0.714 g, 2.44 mmol) in DMF (5 mL). The mixture is stirred for 20 min at rt. 3-Dimethylamino-1-propylchloride hydrochloride (0.611 g, 3.87 mmol, 1.6 eq) is added. The reaction mixture is heated to 90° C., stirred for 10 h, allowed to cool, diluted with EtOAc/H$_2$O and extracted with EtOAc. The organic phase is washed with H$_2$O and brine, dried (Na$_2$SO$_4$), filtered and concentrated. The residue purified by silica gel column chromatography (DCM/MeOH/NH$_3^{aq}$, 94:5:1) to afford 0.398 g of the title compound as an impure brown oil which is used without further purification: ESI-MS: 377.1/379.0 [M+H]$^+$; TLC: R$_f$=0.22 (DCM/MeOH/NH$_3^{aq}$, 94:5:1).

Step 31.2: 4-[1-(4-Bromo-pyridin-2-yl)-1-methyl-ethyl]-phenol

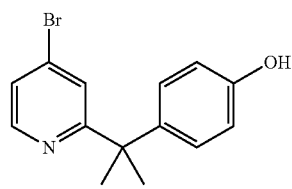 [SMILES: CC(C)(c1ccc(O)cc1)c1cc(Br)ccn1]

BBr₃ (1M in DCM, 23 mmol, 8 eq) is added dropwise to a cold (0° C.) solution of 4-bromo-2-[1-(4-methoxy-phenyl)-1-methyl-ethyl]-pyridine (Step 31.3) (0.878 g, 2.87 mmol) in DCM (42 mL), under an argon atmosphere. The reaction mixture is stirred for 1 h at 0° C., allowed to warm to rt, stirred for 18 h, cooled to 0° C. and quenched by addition of anhydrous MeOH. The mixture is concentrated, diluted with a 6M aqueous solution of HCl, stirred for 1 h, neutralized to pH 7 and extracted with DCM. The organic phase is dried (Na₂SO₄), filtered and concentrated. The residue is used without purification.

Step 31.3: 4-Bromo-2-[1-(4-methoxy-phenyl)-1-methyl-ethyl]-pyridine

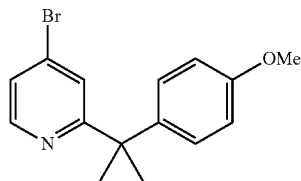 [SMILES: COc1ccc(C(C)(C)c2cc(Br)ccn2)cc1]

The title compound is prepared in analogy to the procedure described in Steps 1.4 to 1.7 but with the following modifications. In Step 1.4, 1,2-dichloroethane (4.3 mL per mmol of pyridin-4-one) is used as the solvent. The reaction mixture is stirred for 1 h at reflux, poured into a saturated aqueous solution of NaHCO₃ and extracted with DCM. In Step 1.5, the reaction mixture is stirred for 23 h at 80° C. and trituration in MeOH is not performed. In Step 1.6, the reaction mixture is stirred for 21 h at rt. In Step 1.7, 4-methoxy-3-buten-2-one in THF is added to a cold (−78° C.) solution of LiHMDS in THF. After 30 min, 2-(4-methoxy-phenyl)-2-methyl-propionyl chloride (Step 27.1) in THF is added and the reaction mixture is allowed to reach it over 16 h.

Title compound: ESI-MS: 306.0/308.0 [M+H]⁺; $t_R$=3.94 min (System 1); TLC: $R_f$=0.55 (Hex/EtOAc, 7:3).

EXAMPLE 32

(S)-Pyrrolidine-1,2-dicarboxylic acid 2-amide 1-({4-methyl-5-[2-(1-d₃-methyl-cyclobutyl)-pyridin-4-yl]-thiazol-2-yl}-amide)

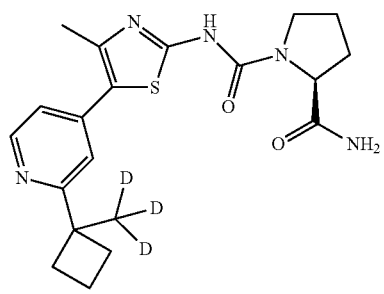 [SMILES: [2H]C([2H])([2H])C1(c2cc(-c3sc(NC(=O)N4CCC[C@H]4C(N)=O)nc3C)ccn2)CCC1]

The title compound is prepared in analogy to the procedure described in Example 1 but with the following modifications. In Example 1, the reaction mixture is stirred for 18 h at rt, quenched by dilution with DCM/H₂O, and extracted with DCM. In Step 1.1, the reaction mixture is stirred for 1 h at reflux. In Step 1.2, the reaction mixture is stirred for 1 h at 100° C. and extracted with DCM after being quenched. In Step 1.3, the palladium catalyst is added to the heated mixture of the remaining reagents and the resulting mixture is stirred for 1 h at 120° C., diluted with EtOAc/H₂O and extracted with EtOAc. After drying and concentration of the organic phase, the residue is purified by silica gel column chromatography (Hex/EtOAc, 1:4). In Step 1.5, the reaction mixture is stirred for 3 h at 80° C. and trituration in MeOH is not performed. In Step 1.7, 4-methoxy-3-buten-2-one in THF is added to a cold (−78° C.) solution of LiHMDS in THF. After 30 min, 1-d₃-methyl-cyclobutane chloride (Step 32.1) in THF is added and the reaction mixture is allowed to reach it over 16 h.

Title compound: ESI-MS: 403.2 [M+H]⁺; TLC: $R_f$=0.22 (DCM/MeOH/NH₃$^{aq}$, 91.5:7.5:1).

Step 32.1: 1-d₃-Methyl-cyclobutanecarbonyl chloride

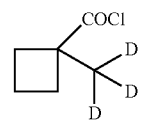 [SMILES: [2H]C([2H])([2H])C1(C(=O)Cl)CCC1]

The title compound is prepared in analogy to the procedure described in Step 5.1 but using 1-d₃-methyl-cyclobutanecarboxylic acid which is prepared according to a described procedure [Cowling, S. J.; Goodby, J. W., Chemical Communications, (2006), (39), 4107-4109] but using d3-methyl-iodide.

EXAMPLE 33

(S)-Pyrrolidine-1,2-dicarboxylic acid 2-amide 1-({5-[2-(1-d₃-methyl-cyclobutyl)-pyridin-4-yl]-thiazol-2-yl}-amide)

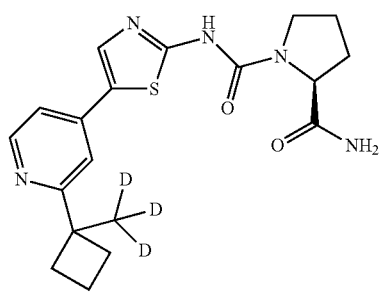 [SMILES: [2H]C([2H])([2H])C1(c2cc(-c3cnc(NC(=O)N4CCC[C@H]4C(N)=O)s3)ccn2)CCC1]

The title compound is prepared in analogy to the procedure described in Example 1 but with the following modifications. In Example 1, the reaction mixture is stirred for 18 h at rt, quenched by dilution with DCM/H₂O and extracted with DCM. In Step 1.1, the reaction mixture is stirred for 1 h at reflux. In Step 1.2, the reaction mixture is stirred for 1 h at 100° C. and extracted with DCM after being quenched. In Step 1.3, N-thiazol-2-yl-acetamide is used. The palladium catalyst is added to the heated mixture of the remaining reagents. The resulting mixture is stirred for 7 h at 120° C., diluted with EtOAc/H₂O, filtered through a pad of celite and extracted with EtOAc. After drying and concentration of the organic phase, the residue is purified by silica gel column chromatography (Hex/EtOAc, 1:4). In Step 1.5, the reaction mixture is stirred for 3 h at 80° C. and trituration in MeOH is not performed. In Step 1.7, 4-methoxy-3-buten-2-one in THF is added to a cold (−78° C.) solution of LiHMDS in THF. After 30 min, 1-d₃-methyl-cyclobutane chloride (Step 32.1) in THF is added and the reaction mixture is allowed to reach it over 16 h.

Title compound: ESI-MS: 389.2 [M+H]⁺; $t_R$=2.30 min (System 1); TLC: $R_f$=0.11 (DCM/MeOH/NH₃$^{aq}$, 91.5:7.5:1).

EXAMPLE 34

(S)-Pyrrolidine-1,2-dicarboxylic acid 2-amide 1-({4-d₃-methyl-5-[2-(1-methyl-cyclopropyl)-pyridin-4-yl]-thiazol-2-yl}amide)

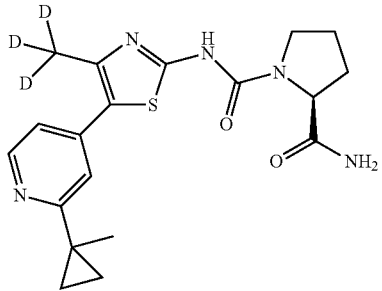 [SMILES: [2H]C([2H])([2H])c1nc(NC(=O)N2CCC[C@H]2C(N)=O)sc1-c1ccnc(C2(C)CC2)c1]

The title compound is prepared in analogy to the procedure described in Example 1 but with the following modifications. In Step 1.1, the reaction mixture is stirred for 8 h at reflux. In Step 1.2, the reaction mixture is stirred for 1 h at 85° C. and extracted with EtOAc after being quenched. In Step 1.3, 2-acetamido-4-d₃-methyl-thiazole (Step 34.1) is used. The reaction mixture is stirred for 2 h at 120° C. In Step 1.5, the reaction mixture is stirred for 1 h at 65-70° C. and trituration in MeOH is not performed. In Step 1.7, 1-methyl-cyclopropanecarbonyl chloride (Step 5.1) is used.

Title compound: ESI-MS: 389.2 [M+H]⁺; $t_R$=2.12 min (System 1); TLC: $R_f$=0.35 (DCM/MeOH, 9:1).

Step 34.1: 2-Acetamido-4-d₃-methyl-thiazole

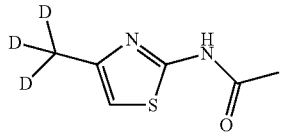

A mixture of 1-bromo-propan-2-one-d₅ [Challacombe, K. et al, Journal of the Chemical Society Perkin Trans. I, (1988), 2213-2218] (1.25 g, 8.8 mmol) and 1-acetyl-2-thiourea (1 g, 8.8 mmol) in EtOH (20 mL) is stirred for 2 h at 85° C., allowed to cool and concentrated. The residue is purified by silica gel column chromatography (Hex/EtOAc, 85:15→1:1) to provide 1.08 g of the title compound as an orange solid: ESI-MS: 160.0 [M+H]⁺; TLC: $R_f$=0.25 (Hex/EtOAc, 1:1).

EXAMPLE 35

(S)-Pyrrolidine-1,2-dicarboxylic acid 2-amide 1-({4-d₃-methyl-5-[2-(2,2,2-trifluoro-1,1-dimethyl-ethyl)-pyridin-4-yl]-thiazol-2-yl}-amide)

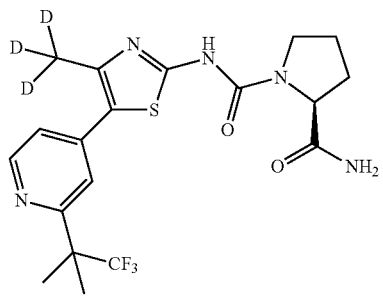 [SMILES: [2H]C([2H])([2H])c1nc(NC(=O)N2CCC[C@H]2C(N)=O)sc1-c1ccnc(C(C)(C)C(F)(F)F)c1]

The title compound is prepared in analogy to the procedure described in Example 1 but with the following modifications. In Step 1.1, the reaction mixture is stirred for 8 h at reflux. In Step 1.2, the reaction mixture is stirred for 1 h at 85° C. and extracted with EtOAc after being quenched. In Step 1.3, 2-acetamido-4-d₃-methyl-thiazole (Step 34.1) is used. The reaction mixture is stirred for 2 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: API-ES-MS: 445.1 [M+H]⁺; $t_R$=3.00 min (System 1); TLC: $R_f$=0.51 (DCM/MeOH, 9:1).

EXAMPLE 36

(S)-Pyrrolidine-1,2-dicarboxylic acid 2-amide 1-({4-dimethylaminomethyl-5-[2-(1-d₃-methyl-cyclobutyl)-pyridin-4-yl]-thiazol-2-yl}-amide)

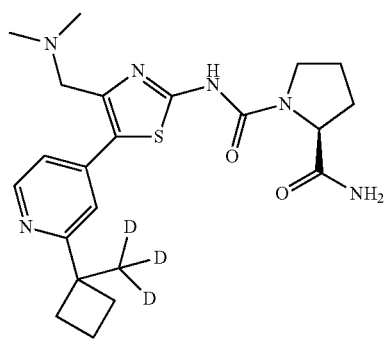 [SMILES: [2H]C([2H])([2H])C1(c2cc(-c3sc(NC(=O)N4CCC[C@H]4C(N)=O)nc3CN(C)C)ccn2)CCC1]

The title compound is prepared in analogy to the procedure described in Example 1 but with the following modifications. In Example 1, the reaction mixture is stirred for 18 h at rt, quenched by dilution with DCM/H₂O and extracted with DCM. In Step 1.1, the reaction mixture is stirred for 2 h at reflux. In Step 1.2, N-{4-dimethylaminomethyl-5-[2-(1-d₃- methyl-cyclobutyl)-pyridin-4-yl]-thiazol-2-yl}-acetamide (Step 36.1) is used. The reaction mixture is stirred for 1 h at 100° C. and extracted with DCM after being quenched.

Title compound: ESI-MS: 446.1 [M+H]⁺; TLC: $R_f$=0.40 (DCM/MeOH/NH$_3^{aq}$, 89:10:1).

Step 36.1: N-{4-Dimethylaminomethyl-5-[2-(1-d$_3$-methyl-cyclobutyl)-pyridin-4-yl]-thiazol-2-yl}-acetamide

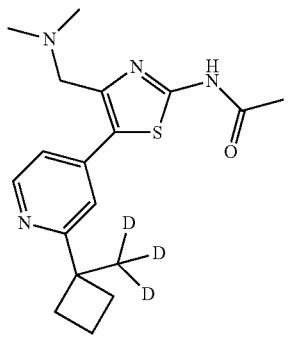 [SMILES: [2H]C([2H])([2H])C1(c2cc(-c3sc(NC(C)=O)nc3CN(C)C)ccn2)CCC1]

A mixture of N-{4-bromomethyl-5-[2-(1-d$_3$-methyl-cyclobutyl)-pyridin-4-yl]-thiazol-2-yl}-acetamide (Step 36.2) (150 mg, 0.391 mmol), dimethylamine hydrochloride (38.3 mg, 0.470 mmol, 1.2 eq) and cesium carbonate (293 mg, 0.900 mmol, 2.3 eq) in DMF (2 mL) is stirred for 2 h at rt, diluted with EtOAc/H$_2$O, and extracted with EtOAc. The organic phase is washed with H$_2$O and brine, dried (Na$_2$SO$_4$), filtered and concentrated. The residue purified by trituration in Et$_2$O to afford 89 mg of the title compound as a white solid: ESI-MS: 348.2 [M+H]⁺.

Step 36.2: N-{4-Bromomethyl-5-[2-(1-d$_3$-methyl-cyclobutyl)-pyridin-4-yl]-thiazol-2-yl}-acetamide

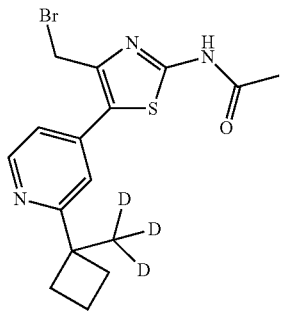 [SMILES: [2H]C([2H])([2H])C1(c2cc(-c3sc(NC(C)=O)nc3CBr)ccn2)CCC1]

NBS (554 mg, 3.06 mmol, 1.1 eq) is added to a solution of N-{4-methyl-5-[2-(1-d$_3$-methyl-cyclobutyl)-pyridin-4-yl]-thiazol-2-yl}-acetamide (Step 36.3) (846 mg, 2.78 mmol) in CCl$_4$ (20 mL) and CHCl$_3$ (16 mL). The reaction mixture is stirred for 1 h at rt, washed with H$_2$O and brine, dried (Na$_2$SO$_4$), filtered and concentrated. The residue purified by silica gel column chromatography (Hex/EtOAc, 1:4) to afford 572 mg of the title compound as a pale yellow solid: ESI-MS: 383.0/385.0 [M+H]⁺; $t_R$=3.12 min (System 1); TLC: $R_f$=0.45 (Hex/EtOAc, 1:4).

Step 36.3: N-{4-Methyl-5-[2-(1-d$_3$-methyl-cyclobutyl)-pyridin-4-yl]-thiazol-2-yl}-acetamide

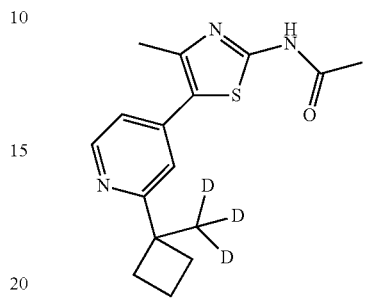

The title compound is prepared in analogy to the procedure described in Steps 1.3 to 1.7 but with the following modifications. In Step 1.3, the reaction mixture is stirred for 1 h at 120° C. and quenched by dilution with EtOAc/H$_2$O. In Step 1.5, the reaction mixture is stirred for 3 h at 80° C. and trituration in MeOH is not performed. In Step 1.7, 4-methoxy-3-buten-2-one in THF is added to a cold (−78° C.) solution of LiHMDS in THF. After 30 min, 1-d$_3$-methyl-cyclobutane chloride (Step 32.1) in THF is added and the reaction mixture is allowed to reach it over 16 h.

Title compound: ESI-MS: 305.2 [M+H]⁺; TLC: $R_f$=0.24 (Hex/EtOAc, 1:4).

EXAMPLE 37

(S)-Pyrrolidine-1,2-dicarboxylic acid 2-amide 1-({4-chloro-5-[2-(2,2,2-trifluoro-1,1-dimethyl-ethyl)-pyridin-4-yl]-thiazol-2-yl}-amide)

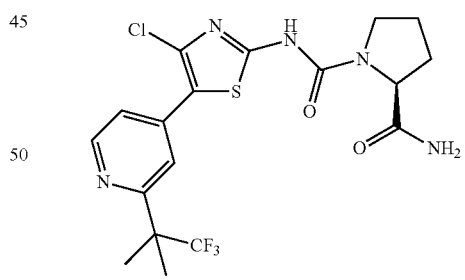

A mixture of 4-chloro-5-[2-(2,2,2-trifluoro-1,1-dimethyl-ethyl)-pyridin-4-yl]-thiazol-2-ylamine (Step 37.1) (100 mg, 0.311 mmol) and phosgene (0.164 mL, 0.311 mmol) in pyridine (2 mL) is stirred for 1 h at 105° C. L-Prolinamide (106 mg, 0.932 mmol, 3 eq) is added. The resulting mixture is stirred for 30 min at 105° C., allowed to cool, quenched by addition of a saturated solution of NaHCO$_3$ (100 mL), and extracted with EtOAc (2×100 mL). The organic phase is washed with a saturated solution of NaHCO$_3$ (100 mL), dried (Na$_2$SO$_4$), filtered and concentrated. The residue is purified by silica gel column chromatography (DCM/MeOH, 99:1→94:6) to afford 46 mg of the title compound as a yellow solid: ESI-MS: 461.9 [M+H]⁺; $t_R$=3.60 min (System 1); TLC: $t_R$=0.28 (DCM/MeOH, 9:1).

Step 37.1: 4-Chloro-5-[2-(2,2,2-trifluoro-1,1-dimethyl-ethyl)-pyridin-4-yl]-thiazol-2-ylamine

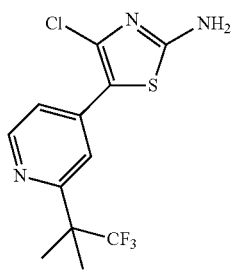 [SMILES: CC(C)(c1cc(-c2sc(N)nc2Cl)ccn1)C(F)(F)F]

The title compound is prepared in analogy to the procedure described in Steps 1.2 to 1.7 but with the following modifications. In Step 1.2, the reaction mixture is stirred for 3 h at 85° C. and extracted with EtOAc after being quenched. In Step 1.3, N-(4-chloro-thiazol-2-yl)-acetamide (Step 37.2) is used. The reaction mixture is stirred for 2 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: ESI-MS: 322.1 [M+H]⁺; $t_R$=3.58 min (System 1); TLC: $R_f$=0.45 (DCM/MeOH, 9:1).

Step 37.2: N-(4-Chloro-thiazol-2-yl)-acetamide

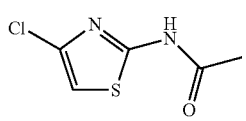

A mixture of N-(4-oxo-4,5-dihydro-thiazol-2-yl)-acetamide (Step 37.3) (14.8 g, 94 mmol) and POCl₃ (175 mL, 20 eq) is heated to 105° C., stirred for 15 min, allowed to cool and concentrated. The residue is poured onto ice-H₂O and extracted with EtOAc (2×100 mL). The organic phase is washed with a saturated solution of NaHCO₃ (2×100 mL), dried (Na₂SO₄), filtered and concentrated. The residue is purified by silica gel column chromatography (DCM/MeOH, 99:1) to afford 13.9 g of the title compound as a white solid: ESI-MS: 177.0 [M+H]⁺; $t_R$=2.74 min (System 1); TLC: $R_f$=0.66 (DCM/MeOH, 9:1).

Step 37.3: N-(4-Oxo-4,5-dihydro-thiazol-2-yl)-acetamide

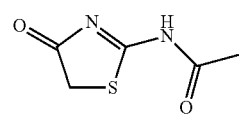

A mixture of pseudothiohydanthoin (16 g, 138 mmol) and acetic anhydride (16.9 mL, 179 mmol, 1.3 eq) in pyridine (150 mL) is heated to 115° C., stirred for 1 h and allowed to cool. The resulting precipitate is collected by filtration to provide 12.64 g of the title compound as a brown solid: ESI-MS: 159.0 [M+H]⁺.

EXAMPLE 38

(S)-Pyrrolidine-1,2-dicarboxylic acid 2-amide 1-({4-fluoromethyl-5-[2-(2,2,2-trifluoro-1,1-dimethyl-ethyl)-pyridin-4-yl]-thiazol-2-yl}-amide)

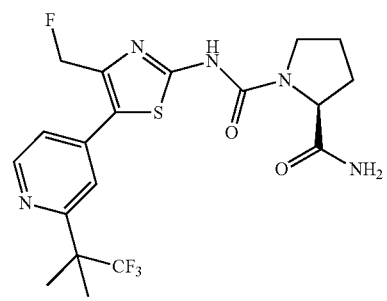 [SMILES: CC(C)(c1cc(-c2sc(NC(=O)N3CCC[C@H]3C(N)=O)nc2CF)ccn1)C(F)(F)F]

The title compound is prepared in analogy to the procedure described in Example 1 but with the following modifications. In Example 1, the reaction mixture is stirred for 18 h at rt, quenched by dilution with DCM/H₂O and extracted with DCM. In Step 1.1, the reaction mixture is stirred for 1 h at reflux, concentrated and the resulting crude material is used without purification. In Step 1.2, N-{4-fluoromethyl-5-[2-(2,2,2-trifluoro-1,1-dimethyl-ethyl)-pyridin-4-yl]-thiazol-2-yl}-acetamide (Step 38.1) is used. The reaction mixture is stirred for 1 h at 100° C. and extracted with DCM after being quenched. The crude material is not purified.

Title compound: ESI-MS: 460.0 [M+H]+; TLC: R₁=0.44 (DCM/MeOH/NH₃$^{aq}$, 91.5:7.5:1]

Step 38.1: N-{4-Fluoromethyl-5-[2-(2,2,2-trifluoro-1,1-dimethyl-ethyl)-pyridin-4-yl]-thiazol-2-yl}-acetamide

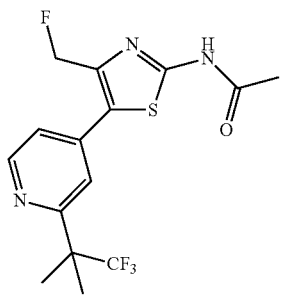 [SMILES: CC(=O)Nc1nc(CF)c(-c2ccnc(C(C)(C)C(F)(F)F)c2)s1]

The title compound is prepared in analogy to the procedure described in Steps 1.3 to 1.7 but with the following modifications. In Step 1.3, N-(4-fluoromethyl-thiazol-2-yl)-acetamide (Step 38.2) is used. The reaction mixture is stirred for 7 h at 90° C., for 5 h at 100° C. and quenched by dilution with EtOAc and H₂O. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: ESI-MS: 362.1 [M+H]+; $t_R$=4.18 min (System 1); TLC: $R_f$=0.29 (Hex/EtOAc, 1:1).

Step 38.2: N-(4-Fluoromethyl-thiazol-2-yl)-acetamide

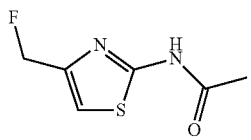

A mixture of 1-chloro-3-fluoro-propan-2-one (Step 38.3) (1.14 g, 10.3 mmol) and N-acetyl-2-thiourea (1.22 g, 10.3 mmol) in EtOH (10 mL) is stirred for 1.5 h at reflux, allowed to cool and concentrated. The residue is dissolved in DCM/H₂O and extracted with DCM. The organic phase is dried (Na₂SO₄), filtered and concentrated. The residue is purified by silica gel column chromatography (Hex/EtOAc, 1:1) to afford 0.143 g of the title compound: ESI-MS: 173.1 [M−H]−; $t_R$=1.98 min (System 1); TLC: $R_f$=0.21 (Hex/EtOAc, 1:1).

Step 38.3: 1-Chloro-3-fluoro-propan-2-one

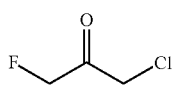

1-Fluoro-3-chloroisopropanol (2.7 mL, 31.2 mmol) is added slowly to a flask containing 30 mL of the Jones' reagent (prepared by adding 230 mL of concentrated sulfuric acid to 267 g of chromium trioxide in 700 mL of H₂O and diluting with H₂O to 1 L) cooled to 5° C. The reaction mixture is allowed to warm to rt, stirred for 18 h, poured into a saturated solution of NaHCO₃ and extracted with Et₂O. The organic phase is washed with brine, dried (Na₂SO₄), filtered and concentrated. The residue is purified by silica gel column chromatography (DCM) to afford 1.14 g of the title compound as an impure yellow oil.

EXAMPLE 39

(S)-Pyrrolidine-1,2-dicarboxylic acid 2-amide 1-{[5-(5-benzenesulfonylamino-6-chloro-pyridin-3-yl)-4-methyl-thiazol-2-yl]-amide}

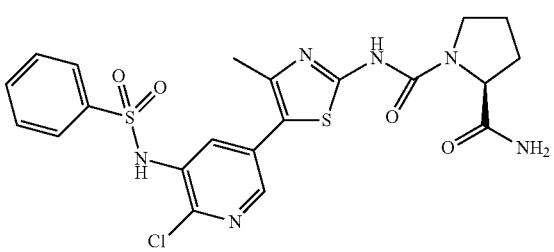 [SMILES: Cc1nc(NC(=O)N2CCC[C@H]2C(N)=O)sc1-c1cnc(Cl)c(NS(=O)(=O)c2ccccc2)c1]

The title compound is prepared in analogy to the procedure described in Step 1.3 but with the following modifications. (S)-Pyrrolidine-1,2-dicarboxylic acid 2-amide 1-[(4-methyl-thiazol-2-yl)-amide] (Step 39.2) and N-(5-bromo-2-chloro-pyridin-3-yl)-benzenesulfonamide (step 39.1) are used. The palladium catalyst is added to the heated mixture of the remaining reagents and the resulting mixture is stirred for 3 h at 135° C., diluted with EtOAc and H₂O, filtered through a pad of celite and extracted with EtOAc. After drying and concentration of the organic phase, the residue is purified by silica gel column chromatography and by reverse phase HPLC. Title compound: ESI-MS: 519.0/521.1 [M−H]−; $t_R$=3.33 min (System 1); TLC: $R_f$=0.09 (DCM/MeOH/NH₃$^{aq}$, 84:15:1).

Step 39.1: N-(5-Bromo-2-chloro-pyridin-3-yl)-benzenesulfonamide

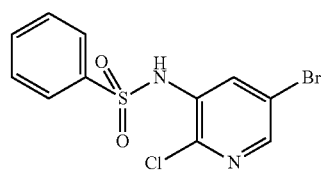 [SMILES: O=S(=O)(Nc1cc(Br)cnc1Cl)c1ccccc1]

A solution of benzenesulfonyl chloride (1.23 mL, 9.62 mmol, 2 eq) in DCM (50 mL) is added dropwise over 15 min to a solution of 3-amino-5-bromo-2-chloropyridine [Jouve, K.; Bergman, J., Journal of Heterocyclic Chemistry, (2003), 40(2), 261-268] (1 g, 4.81 mmol) and pyridine (1.94 ml, 24 mmol, 5 eq) in DCM (20 mL), under an argon atmosphere. The resulting mixture is stirred for 20 h at rt, concentrated, diluted with H₂O and extracted with DCM. The organic phase is washed with brine, dried (Na₂SO₄), filtered and concentrated. The residue is purified by silica gel column chromatography (DCM) to afford 163 mg of the title compound as a white solid: ESI-MS: 346.9 [M–H]⁻; $t_R$=4.33 min (System 1); TLC: $R_f$=0.23 (DCM).

Step 39.2: (S)-Pyrrolidine-1,2-dicarboxylic acid 2-amide 1-[(4-methyl-thiazol-2-yl)-amide]

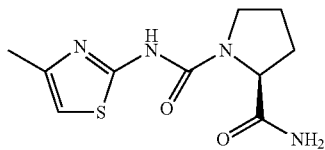 [SMILES: Cc1csc(NC(=O)N2CCC[C@H]2C(N)=O)n1]

The title compound is prepared in analogy to the procedure described in Example 1 but using imidazole-1-carboxylic acid (4-methyl-thiazol-2-yl)-amide (Step 39.3). The reaction mixture is stirred mixture for 18 h at rt and concentrated. The residue is purified by silica gel column chromatography (DCM/MeOH/NH₃$^{aq}$, 94:5:1) followed by trituration in Et₂O. Title compound: ESI-MS: 253.2 [M–H]⁻; TLC: $R_f$=0.18 (DCM/MeOH/NH₃$^{aq}$, 84:15:1).

Step 39.3: Imidazole-1-carboxylic acid (4-methyl-thiazol-2-yl)-amide

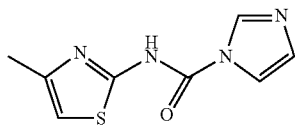

The title compound is prepared in analogy to the procedure described in Step 1.1 but using 2-acetamido-4-methylthiazole and stirring the reaction mixture for 5.5 h at reflux.

EXAMPLE 40

(S)-Pyrrolidine-1,2-dicarboxylic acid 2-amide 1-{[5-(5-benzenesulfonylamino-6-chloro-pyridin-3-yl)-thiazol-2-yl]-amide}

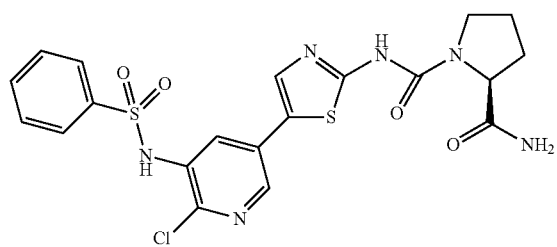 [SMILES: NC(=O)[C@@H]1CCCN1C(=O)Nc1ncc(-c2cnc(Cl)c(NS(=O)(=O)c3ccccc3)c2)s1]

The title compound is prepared in analogy to the procedure described in Step 1.3 but with the following modifications. (S)-Pyrrolidine-1,2-dicarboxylic acid 2-amide 1-thiazol-2-ylamide (Step 40.1) and N-(5-bromo-2-chloro-pyridin-3-yl)-benzenesulfonamide (step 39.1) are used. The palladium catalyst is added to the heated mixture of the remaining reagents and the resulting mixture is stirred for 6 h at 120° C., concentrated, diluted with DCM/MeOH, filtered through a pad of celite and the filtrate is concentrated. The residue is purified by silica gel column chromatography and by reverse phase HPLC. Title compound: ESI-MS: 506.9 [M+H]⁺; $t_R$=3.21 min (System 1).

Step 40.1: (S)-Pyrrolidine-1,2-dicarboxylic acid 2-amide 1-thiazol-2-ylamide

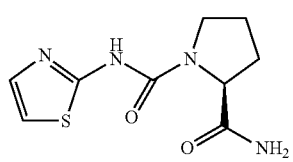 [SMILES: NC(=O)[C@@H]1CCCN1C(=O)Nc1nccs1]

The title compound is prepared in analogy to the procedure described in Example 1 but using imidazole-1-carboxylic acid thiazol-2-ylamide (Step 40.2). The reaction mixture is stirred mixture for 18 h at rt and concentrated. The residue is purified by silica gel column chromatography (DCM/MeOH/NH₃$^{aq}$, 94:5:1) followed by trituration in EtOAc. Title compound: ESI-MS: 239.2 [M–H]⁻; TLC: $R_f$=0.11 (DCM/MeOH/NH₃$^{aq}$, 84:15:1).

Step 40.2: Imidazole-1-carboxylic acid thiazol-2-ylamide

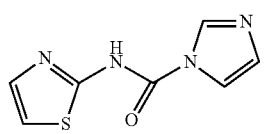 [SMILES: O=C(Nc1nccs1)n1ccnc1]

The title compound is prepared in analogy to the procedure described in Step 1.1 but using N-thiazol-2-yl-acetamide and stirring the reaction mixture for 5 h at reflux.

EXAMPLE 41

(S)-Pyrrolidine-1,2-dicarboxylic acid 2-amide 1-{[5-(6-amino-5-trifluoromethyl-pyridin-3-yl)-4-methyl-thiazol-2-yl]-amide}

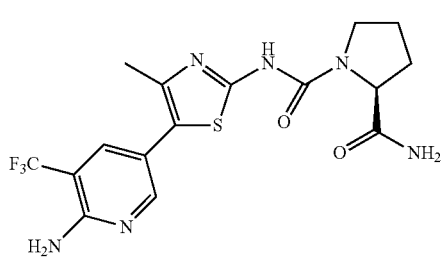 [SMILES: Cc1nc(NC(=O)N2CCC[C@H]2C(N)=O)sc1-c1cnc(N)c(C(F)(F)F)c1]

The title compound is prepared in analogy to the procedure described in Step 1.3 but with the following modifications. (S)-Pyrrolidine-1,2-dicarboxylic acid 2-amide 1-[(4-methyl-thiazol-2-yl)-amide] (Step 39.2) and 5-bromo-3-trifluoromethyl-pyridin-2-ylamine (WO2007095588) are used. The palladium catalyst is added to the heated mixture of the remaining reagents and the resulting mixture is stirred for 3 h at 120° C., diluted with DCM/H₂O and extracted with DCM. After drying and concentration of the organic phase, the residue is purified by silica gel column chromatography and by reverse phase HPLC. Title compound: ESI-MS: 413.1 [M−H]⁻; TLC: R$_f$=0.27 (DCM/MeOH/NH$_3^{aq}$, 89:10:1).

EXAMPLE 42

(S)-Pyrrolidine-1,2-dicarboxylic acid 2-amide 1-({4-methyl-5-[2-(1-methyl-cyclopropyl)-pyrimidin-4-yl]-thiazol-2-yl}-amide)

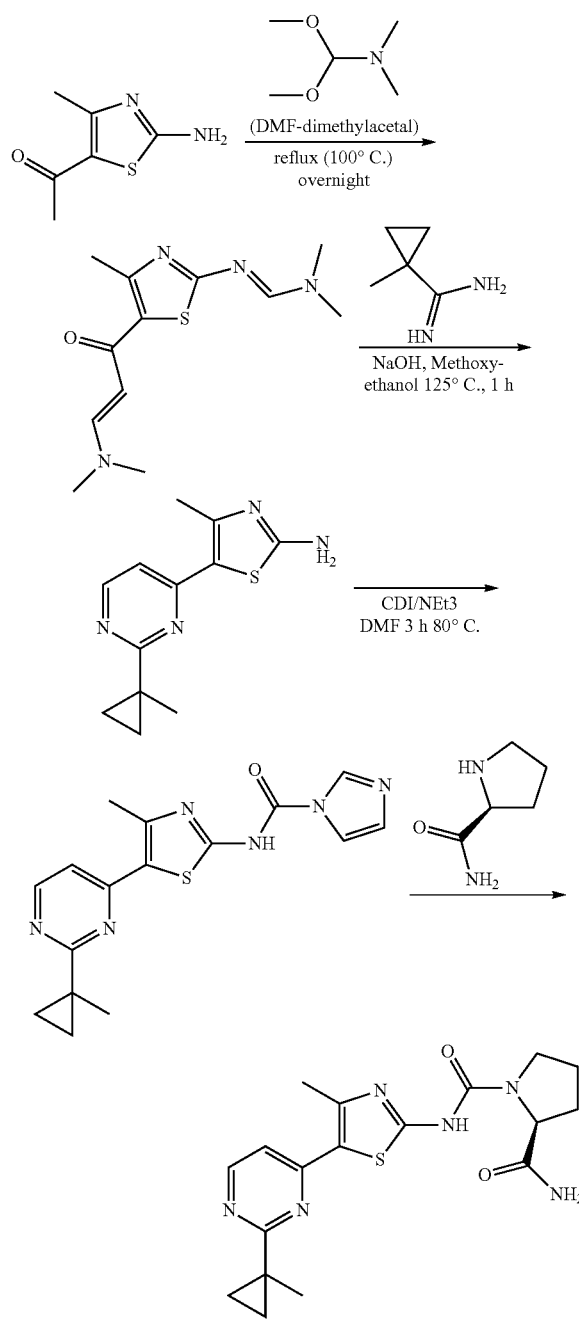

example 42

Imidazole-1-carboxylic acid {4-methyl-5-[2-(1-methyl-cyclopropyl)-pyrimidin-4-yl]-thiazol-2-yl}-amide (4.0 g) is added to a stirred solution of L-proline amide (1.48 g) and triethylamine (4.1 ml) in DMF (46 ml) at room temperature. The reaction mixture is stood at room temperature for 22 hours, evaporated and the title compound is obtained as a white solid after crystallization with methanol (60 ml) and water (20 ml). HPLC/MS: retention time 1.24 minutes, M+H 387.1 and M−H 385.2.

Step 42.1: Imidazole-1-carboxylic acid {4-methyl-5-[2-(1-methyl-cyclopropyl)-pyrimidin-4-yl]-thiazol-2-yl}-amide

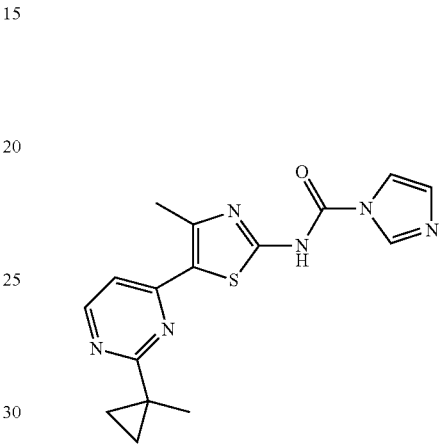

Carbonyl diimidazole (4.56 g) is added to a solution of 4-methyl-5-[2-(1-methyl-cyclopropyl)-pyrimidin-4-yl]-thiazol-2-ylamine (10.5 g) and triethylamine (4.28 ml) in DMF (26 ml) at room temperature and then heated for 2 hours at 80° C. After cooling the title compound is isolated by filtration.

Step 42.2: 4-Methyl-5-[2-(1-methyl-cyclopropyl)-pyrimidin-4-yl]-thiazol-2-ylamine

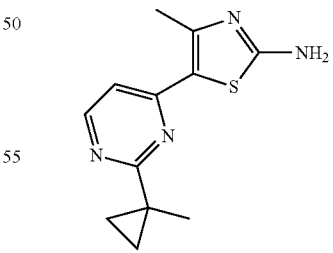

Powdered sodium hydroxide (5.86 g) is added to a solution of N'-[5-(3-dimethylamino-acryloyl)-4-methyl-thiazol-2-yl]-N,N-dimethyl-formamidine (13 g, prepared as described by S. Wang et al J. Med. Chem. 2004, 47, 1662-1675.) and 1-methyl-cyclopropanecarboxamidine hydrochloride (7.2 g, prepared as described in EP0227415) in 2-methoxyethanol (98 ml) and the mixture heated at 125° C. for 1 hour with stirring. The reaction mixture is cooled, water is added, and the title compound isolated by filtration. ESI-MS: M+H 247 and M−H 245.

EXAMPLE 43

(S)-Pyrrolidine-1,2-dicarboxylic acid 2-amide 1-{[5-(2-isopropyl-pyrimidin-4-yl)-4-methyl-thiazol-2-yl]-amide}

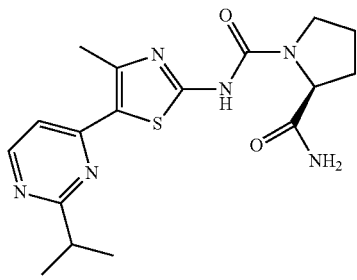 [SMILES: Cc1nc(NC(=O)N2CCC[C@H]2C(N)=O)sc1-c1ccnc(C(C)C)n1]

Imidazole-1-carboxylic acid [5-(2-isopropyl-pyrimidin-4-yl)-4-methyl-thiazol-2-yl]-amide (50 mg) is added to a solution of L-proline amide (19 mg) and triethylamine (26 µl) in DMF (152 µl) at room temperature. The mixture is stirred for 2 hours at 40° C. and then purified by preparative reversed phase chromatography. Fractions containing the title compound are captured with a 300 mg BondElut SPE, SCX cartridge and then released with 7M ammonia in methanol solution (1 ml). The title compound is obtained by evaporation. ESI-MS: M+H 275 and M−H 273.

Step 43.1: Imidazole-1-carboxylic acid {4-methyl-5-[2-isopropyl-pyrimidin-4-yl]-thiazol-2-yl}-amide

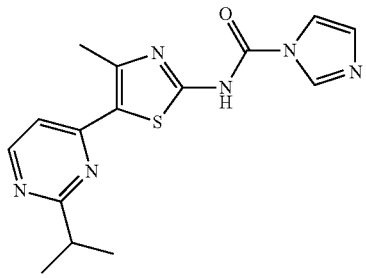 [SMILES: Cc1nc(NC(=O)n2ccnc2)sc1-c1ccnc(C(C)C)n1]

The title compound is prepared in analogy to the procedure described in Example 42, but using 4-methyl-5-[2-isopropyl-pyrimidin-4-yl]-thiazol-2-ylamine in place of 4-methyl-5-[2-(1-methyl-cyclopropyl)-pyrimidin-4-yl]-thiazol-2-ylamine.

EXAMPLE 44

(S)-Pyrrolidine-1,2-dicarboxylic acid 2-amide 1-{[5-(2-benzyl-pyrimidin-4-yl)-4-methyl-thiazol-2-yl]-amide}

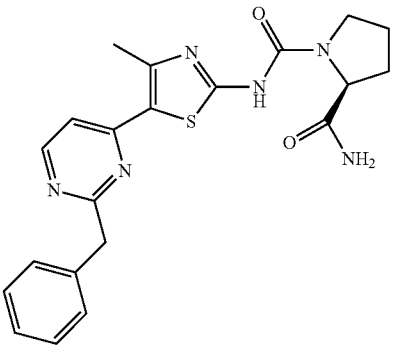 [SMILES: Cc1nc(NC(=O)N2CCC[C@H]2C(N)=O)sc1-c1ccnc(Cc2ccccc2)n1]

The title compound is prepared in analogy to the procedure described in Example 43, but using 4-methyl-5-[2-benzyl-pyrimidin-4-yl]-thiazol-2-ylamine in place of 4-methyl-5-[2-isopropyl-pyrimidin-4-yl]-thiazol-2-ylamine. ESI-MS: M+H 423 and M−H 421.

EXAMPLE 45

(S)-Pyrrolidine-1,2-dicarboxylic acid 2-amide 1-{[5-(2-ethyl-pyrimidin-4-yl)-4-methyl-thiazol-2-yl]-amide}

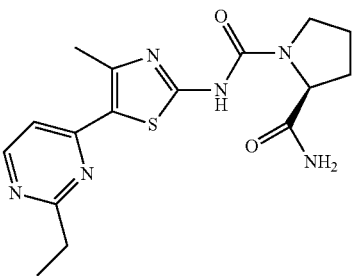 [SMILES: CCc1nccc(-c2sc(NC(=O)N3CCC[C@H]3C(N)=O)nc2C)n1]

The title compound is prepared in analogy to the procedure described in Example 43, but using 4-methyl-5-[2-ethyl-pyrimidin-4-yl]-thiazol-2-ylamine in place of 4-methyl-5-[2-isopropyl-pyrimidin-4-yl]-thiazol-2-ylamine. ESI-MS: M+H 361 and M−H 359.

EXAMPLE 46

(S)-Pyrrolidine-1,2-dicarboxylic acid 2-amide 1-{[5-(2-methoxymethyl-pyrimidin-4-yl)-4-methyl-thiazol-2-yl]-amide}

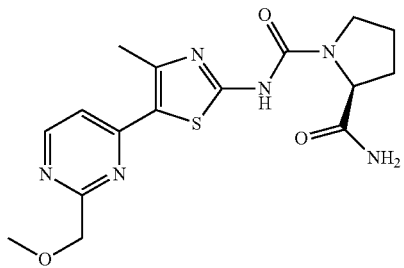 [SMILES: COCc1nccc(-c2sc(NC(=O)N3CCC[C@H]3C(N)=O)nc2C)n1]

The title compound is prepared in analogy to the procedure described in Example 43, but using 4-methyl-5-[2-methoxymethyl-pyrimidin-4-yl]-thiazol-2-ylamine in place of 4-methyl-5-[2-isopropyl-pyrimidin-4-yl]-thiazol-2-ylamine. ESI-MS: M+H 377 and M−H 375.

EXAMPLE 47

(S)-Pyrrolidine-1,2-dicarboxylic acid 2-amide 1-({5-[2-(2,6-dichloro-benzyl)-pyrimidin-4-yl]-4-methyl-thiazol-2-yl}-amide)

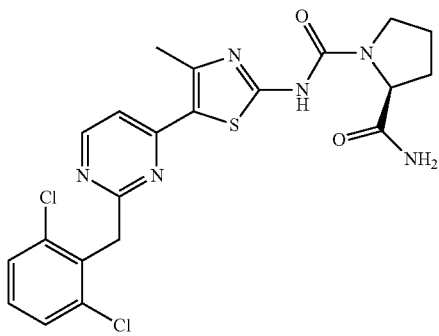 [SMILES: Cc1nc(NC(=O)N2CCC[C@H]2C(N)=O)sc1-c1ccnc(Cc2c(Cl)cccc2Cl)n1]

The title compound is prepared in analogy to the procedure described in Example 43, but using 4-methyl-5-[2-(2,6-dichloro-benzyl)-pyrimidin-4-yl]-thiazol-2-ylamine in place of 4-methyl-5-[2-isopropyl-pyrimidin-4-yl]-thiazol-2-ylamine. ESI-MS: M+H 491, 493 and M−H 489, 491.

EXAMPLE 48

(S)-Pyrrolidine-1,2-dicarboxylic acid 2-amide 1-{[5-(2-isobutyl-pyrimidin-4-yl)-4-methyl-thiazol-2-yl]-amide}

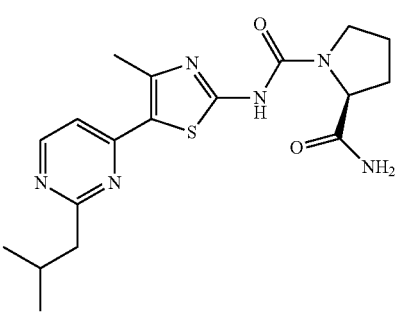 [SMILES: Cc1nc(NC(=O)N2CCC[C@H]2C(N)=O)sc1-c1ccnc(CC(C)C)n1]

The title compound is prepared in analogy to the procedure described in Example 43, but using 4-methyl-5-[2-isobutyl-pyrimidin-4-yl]-thiazol-2-ylamine in place of 4-methyl-5-[2-isopropyl-pyrimidin-4-yl]-thiazol-2-ylamine. ESI-MS: M+H 389 and M−H 387.

EXAMPLE 49

(S)-Pyrrolidine-1,2-dicarboxylic acid 2-amide 1-({5-[2-(4-methoxy-phenoxymethyl)-pyrimidin-4-yl]-4-methyl-thiazol-2-yl}-amide)

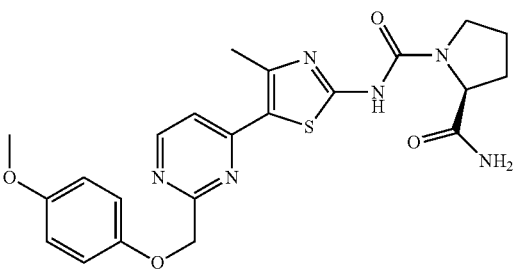 [SMILES: COc1ccc(OCc2nccc(-c3sc(NC(=O)N4CCC[C@H]4C(N)=O)nc3C)n2)cc1]

The title compound is prepared in analogy to the procedure described in Example 43, but using 4-methyl-5-[2-(4-methoxy-phenoxymethyl)-pyrimidin-4-yl]-thiazol-2-ylamine in place of 4-methyl-5-[2-isopropyl-pyrimidin-4-yl]-thiazol-2-ylamine. ESI-MS: M+H 469 and M−H 467.

EXAMPLE 50

(S)-Pyrrolidine-1,2-dicarboxylic acid 2-amide 1-({5-[2-(3-methoxy-phenoxymethyl)-pyrimidin-4-yl]-4-methyl-thiazol-2-yl}-amide)

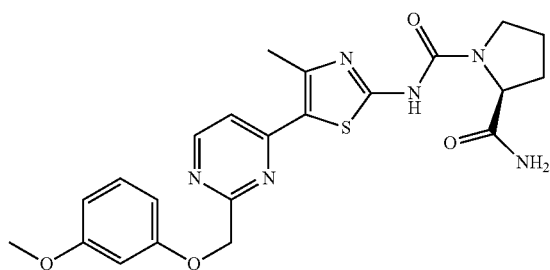 [SMILES: COc1cccc(OCc2nccc(-c3sc(NC(=O)N4CCC[C@H]4C(N)=O)nc3C)n2)c1]

The title compound is prepared in analogy to the procedure described in Example 43, but using 4-methyl-5-[2-(3-methoxy-phenoxymethyl)-pyrimidin-4-yl]-thiazol-2-ylamine in place of 4-methyl-5-[2-isopropyl-pyrimidin-4-yl]-thiazol-2-ylamine. ESI-MS M−H 467.

EXAMPLE 51

(S)-Pyrrolidine-1,2-dicarboxylic acid 2-amide 1-({5-[2-(2-fluoro-phenyl)-pyrimidin-4-yl]-4-methyl-thiazol-2-yl}-amide)

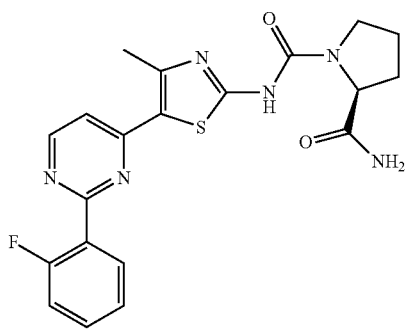 [SMILES: Cc1nc(NC(=O)N2CCC[C@H]2C(N)=O)sc1-c1ccnc(-c2ccccc2F)n1]

Imidazole-1-carboxylic acid {5-[2-(2-fluoro-phenyl)-pyrimidin-4-yl]-4-methyl-thiazol-2-yl}-amide (415 mg) is added to a solution of L-proline amide (137 mg) and triethylamine (182 μl) in DMF (1.1 ml) at room temperature. The mixture is stirred for 18 hours at 40° C., evaporated and crystallized from methanol (8 ml) and water (2 ml) to give the title compound as a white solid. ESI-MS: M+H 427 and M−H 425.

Step 51.1: Imidazole-1-carboxylic acid {5-[2-(2-fluoro-phenyl)-pyrimidin-4-yl]-4-methyl-thiazol-2-yl}-amide

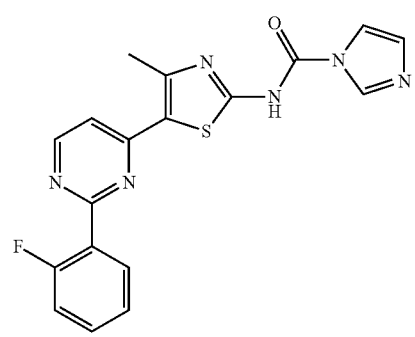 [SMILES: Cc1nc(NC(=O)n2ccnc2)sc1-c1ccnc(-c2ccccc2F)n1]

The title compound is prepared in analogy to the procedure described in Example 43, but using 4-methyl-5-[2-(2-fluoro-phenyl)-pyrimidin-4-yl]-thiazol-2-ylamine in place of 4-methyl-5-[2-(1-methyl-cyclopropyl)-pyrimidin-4-yl]-thiazol-2-ylamine.

EXAMPLE 52

(S)-Pyrrolidine-1,2-dicarboxylic acid 2-amide 1-{[5-(2-trifluoromethyl-pyrimidin-4-yl)-4-methyl-thiazol-2-yl]-amide}

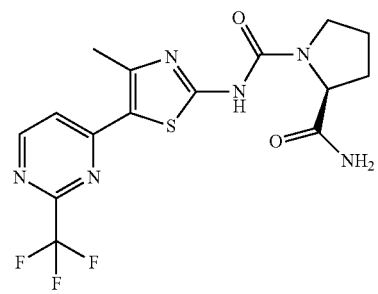 [SMILES: Cc1nc(NC(=O)N2CCC[C@H]2C(N)=O)sc1-c1ccnc(C(F)(F)F)n1]

L-Proline amide (9 mg) is added to a solution of imidazole-1-carboxylic acid [5-(2-trifluoromethyl-pyrimidin-4-yl)-4-methyl-thiazol-2-yl]-amide (25 mg) and triethylamine (12 μl) in DMF (71 μl) at room temperature. The mixture is stirred for 18 hours at 25° C. and purified by preparative reversed phase chromatography. Fractions containing the title compound are captured with a 300 mg BondElut SPE, SCX cartridge and then released with 7M ammonia in methanol solution (1 ml). The title compound is obtained by evaporation. ESI-MS: M+H 401 and M−H 399.

Step 52.1: Imidazole-1-carboxylic acid {4-methyl-5-[2-trifluoromethyl-pyrimidin-4-yl]-thiazol-2-yl}-amide

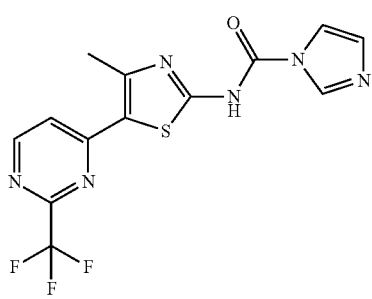 [SMILES: Cc1nc(NC(=O)n2ccnc2)sc1-c1ccnc(C(F)(F)F)n1]

The title compound is prepared in analogy to the procedure described in Example 43, but using 4-methyl-5-[2-trifluoromethyl-pyrimidin-4-yl]-thiazol-2-ylamine in place of 4-methyl-5-[2-(1-methyl-cyclopropyl)-pyrimidin-4-yl]thiazol-2-ylamine.

EXAMPLE 53

(S)-Pyrrolidine-1,2-dicarboxylic acid 2-amide 1-({4-methyl-5-[2-(1,1,2-trimethyl-propyl)-pyrimidin-4-yl]-thiazol-2-yl}-amide)

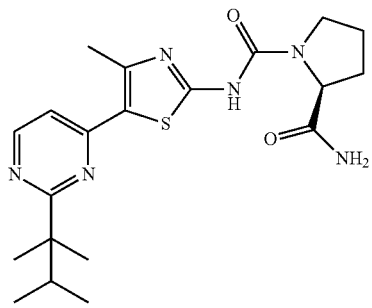 [SMILES: Cc1nc(NC(=O)N2CCC[C@H]2C(N)=O)sc1-c1ccnc(C(C)(C)C(C)C)n1]

The title compound is prepared in analogy to the procedure described in Example 51, but using 4-methyl-5-[2-(1,1,2-trimethyl-propyl)-pyrimidin-4-yl]-thiazol-2-ylamine in place of 4-methyl-5-[2-(2-fluoro-phenyl)-pyrimidin-4-yl]-thiazol-2-ylamine. ESI-MS: M+H 417 and M−H 415.

EXAMPLE 54

(S)-Pyrrolidine-1,2-dicarboxylic acid 2-amide 1-[(5-{2-[1-(4-methoxy-phenyl)-1-methyl-ethyl]-pyrimidin-4-yl}-4-methyl-thiazol-2-yl)-amide]

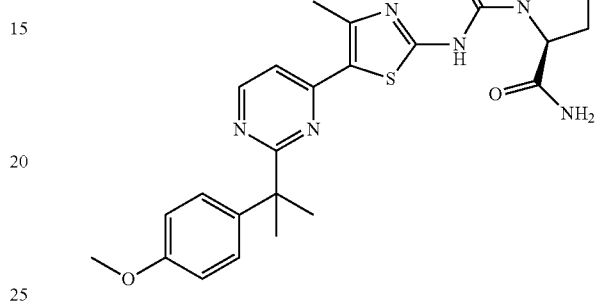

The title compound is prepared in analogy to the procedure described in Example 51, but using 5-{2-[1-(4-methoxy-phenyl)-1-methyl-ethyl]-pyrimidin-4-yl}-4-methyl-thiazol-2-ylamine in place of 4-methyl-5-[2-(2-fluoro-phenyl)-pyrimidin-4-yl]-thiazol-2-ylamine. ESI-MS: M+H 495 and M−H 493.

EXAMPLE 55

(S)-Pyrrolidine-1,2-dicarboxylic acid 2-amide 1-({5-[2-(2-fluoro-1-fluoromethyl-1-methyl-ethyl)-pyridin-4-yl]-4-methyl-thiazol-2-yl}-amide)

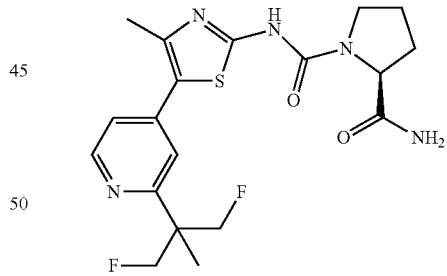

The title compound is prepared in analogy to the procedure described in Example 1 but with the following modifications. In Example 1, the reaction mixture is stirred for 6 h at rt. In Step 1.1, the reaction mixture is stirred for 15 h at reflux. In Step 1.2, the reaction mixture is stirred for 1 h at 100° C. and extracted with EtOAc after being quenched. In Step 1.3, the reaction mixture is stirred for 2 h at 120° C. In Step 1.4, the reaction mixture is stirred for 30 min at 85° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3-fluoro-2-fluoromethyl-2-methyl-propionyl chloride (Step 55.1) is used.

Title compound: ESI-MS: 424.1 [M+H]⁺; $t_R$=2.40 min (System 1); TLC: $R_f$=0.35 (DCM/MeOH, 9:1).

Step 55.1:
3-Fluoro-2-fluoromethyl-2-methyl-propionyl chloride

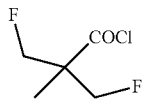

The title compound is prepared in analogy to the procedure described in Step 5.1 but using 3-fluoro-2-fluoromethyl-2-methyl-propionic acid (Step 55.2).

Step 55.2:
3-Fluoro-2-fluoromethyl-2-methyl-propionic acid

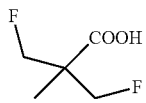

The title compound is prepared in analogy to the procedure described in Step 73.2 but using 3-fluoro-2-fluoromethyl-2-methyl-propionic acid methyl ester (preparation WO 2007/053394). ESI-MS: 137.0 [M−H]⁻.

EXAMPLE 56

(S)-Pyrrolidine-1,2-dicarboxylic acid 2-amide 1-({4-methyl-5-[2-(1,1-dimethyl-propyl)-pyrimidin-4-yl]-thiazol-2-yl}-amide)

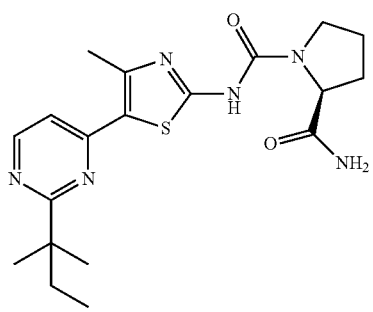 [SMILES: CCC(C)(C)c1nccc(-c2sc(NC(=O)N3CCC[C@H]3C(N)=O)nc2C)n1]

The title compound is prepared in analogy to the procedure described in Example 43, but using 4-methyl-5-[2-(1,1-dimethyl-propyl)-pyrimidin-4-yl]-thiazol-2-ylamine in place of 4-methyl-5-[2-isopropyl-pyrimidin-4-yl]-thiazol-2-ylamine. ESI-MS: M+H 403 and M−H 401.

EXAMPLE 57

(S)-Pyrrolidine-1,2-dicarboxylic acid 2-amide 1-({4-methyl-5-[2-(1-methyl-1-p-tolyl-ethyl)-pyrimidin-4-yl]-thiazol-2-yl}-amide)

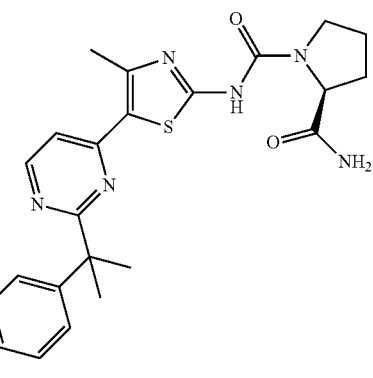

The title compound is prepared in analogy to the procedure described in Example 43, but using 4-methyl-5-[2-(1-methyl-1-p-tolyl-ethyl)-pyrimidin-4-yl]-thiazol-2-ylamine in place of 4-methyl-5-[2-isopropyl-pyrimidin-4-yl]-thiazol-2-ylamine. ESI-MS: M+H 479 and M−H 477.

EXAMPLE 58

(S)-Pyrrolidine-1,2-dicarboxylic acid 2-amide 1-({4-methyl-5-[2-(1-phenyl-cyclopentyl)-pyrimidin-4-yl]-thiazol-2-yl}-amide)

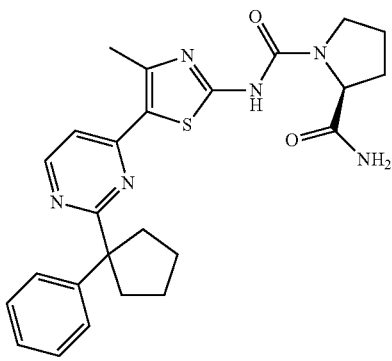 [SMILES: Cc1nc(NC(=O)N2CCC[C@H]2C(N)=O)sc1-c1ccnc(C2(c3ccccc3)CCCC2)n1]

The title compound is prepared in analogy to the procedure described in Example 43, but using 4-methyl-5-[2-(1-phenyl-cyclopentyl)-pyrimidin-4-yl]-thiazol-2-ylamine in place of 4-methyl-5-[2-isopropyl-pyrimidin-4-yl]-thiazol-2-ylamine. ESI-MS: M+H 477 and M−H 475.

EXAMPLE 59

(S)-Pyrrolidine-1,2-dicarboxylic acid 2-amide 1-({4-methyl-5-[2-cyclopropyl-pyrimidin-4-yl]thiazol-2-yl}-amide)

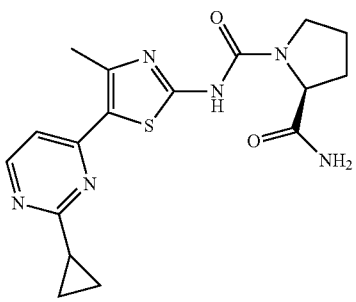 [SMILES: Cc1nc(NC(=O)N2CCC[C@H]2C(N)=O)sc1-c1ccnc(C2CC2)n1]

The title compound is prepared in analogy to the procedure described in Example 43, but using 4-methyl-5-[2-cyclopropyl-pyrimidin-4-yl]-thiazol-2-ylamine in place of 4-methyl-5-[2-isopropyl-pyrimidin-4-yl]-thiazol-2-ylamine. ESI-MS: M+H 373 and M−H 371.

EXAMPLE 60

(S)-Pyrrolidine-1,2-dicarboxylic acid 2-amide 1-({4-methyl-5-[2-cyclobutyl-pyrimidin-4-yl]-thiazol-2-yl}-amide)

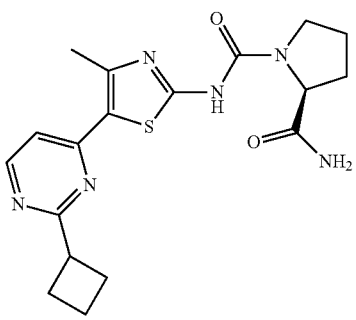 [SMILES: Cc1nc(NC(=O)N2CCC[C@H]2C(N)=O)sc1-c1ccnc(C2CCC2)n1]

The title compound is prepared in analogy to the procedure described in Example 52, but using 4-methyl-5-[2-cyclobutyl-pyrimidin-4-yl]-thiazol-2-ylamine in place of 4-methyl-5-[2-trifluoromethyl-pyrimidin-4-yl]-thiazol-2-ylamine. ESI-MS: M+H 387 and M−H 385.

EXAMPLE 61

(S)-Pyrrolidine-1,2-dicarboxylic acid 2-amide 1-{[5-(2-$d_9$-tert-butyl-pyrimidin-4-yl)-4-methyl-thiazol-2-yl]-amide}

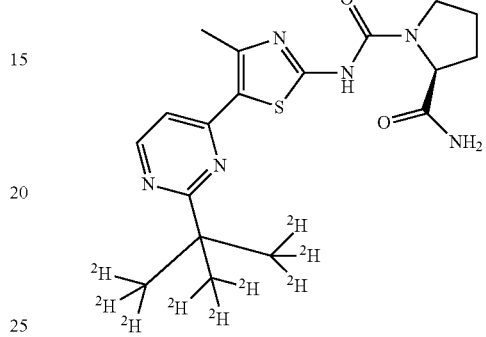

Imidazole-1-carboxylic acid [5-(2-$d_9$-tert-butyl-pyrimidin-4-yl)-4-methyl-thiazol-2-yl]-amide (0.82 g) is added to a stirred solution of L-proline amide (0.29 g) and triethylamine (0.81 ml) in DMF (5 ml) at room temperature. The reaction mixture is stood at room temperature for 22 hours, then evaporated and the title compound is obtained as a white solid after crystallization twice with 2:1 methanol:water. HPLC/MS: retention time 1.27 minutes, M+H 398.3 and M−H 396.3.

Step 61.1: Imidazole-1-carboxylic acid [5-(2-$d_9$-tert-butyl-pyrimidin-4-yl)-4-methyl-thiazol-2-yl]-amide

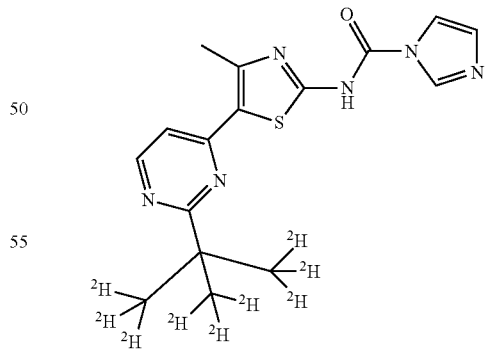

Carbonyl diimidazole (0.77 g) is added to a stirred solution of 5-(2-$d_9$-tert-butyl-pyrimidin-4-yl)-4-methyl-thiazol-2-ylamine (1.11 g) in DMF (4.3 ml) at room temperature. The reaction mixture is then stood for 18 hours at 25° C. after which time the title compound is isolated by filtration.

Step 61.2: 5-(2-d$_9$-tert-Butyl-pyrimidin-4-yl)-4-methyl-thiazol-2-ylamine

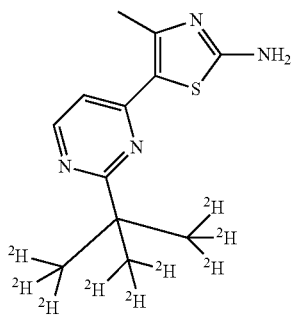 [SMILES: [2H]C([2H])([2H])C(c1nccc(-c2sc(N)nc2C)n1)(C([2H])([2H])[2H])C([2H])([2H])[2H]]

Powdered sodium hydroxide (3.71 g) is added to a solution of N'-[5-(3-dimethylamino-acryloyl)-4-methyl-thiazol-2-yl]-N,N-dimethyl-formamidine (5.51 g) and d$_9$-2,2-dimethyl-propionamidine hydrochloride (4.50 g) in 2-methoxy-ethanol (41 ml) and the mixture is heated at 125° C. for 1 hour with stirring. The reaction mixture is cooled, water is added, and the crude product is isolated by filtration. The crude product is purified by preparative HPLC and the fractions containing the title compound partitioned between dichloromethane and aqueous sodium bicarbonate. The title compound is obtained as a yellow solid after evaporation of the dried dichloromethane layers. HPLC/MS: retention time 1.12 minutes, M+H 258.4.

Step 61.3: d$_9$-2,2-Dimethyl-propionamidine hydrochloride

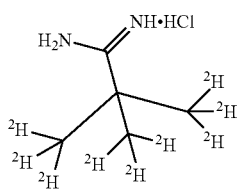

A 2M solution of trimethylaluminium in toluene (61 ml) is added dropwise to a suspension of ammonium chloride (6.53 g) in toluene (46 ml) cooled with an ice bath. The reaction mixture is stirred for 4 hours at room temperature and d$_9$-2,2-dimethyl-propionic acid butyl ester (6.3 g) is added. After heating at 80° C. for 4 days the reaction mixture is cooled to 0° C. and methanol (200 ml) is added drop wise. After stirring and sonication for 1 hour at room temperature the reaction mixture is filtered through Hyflo, washing with methanol, and the filtrate is evaporated to give the title compound as an off-white solid.

Step 61.4: d$_9$-2,2-Dimethyl-propionic acid butyl ester

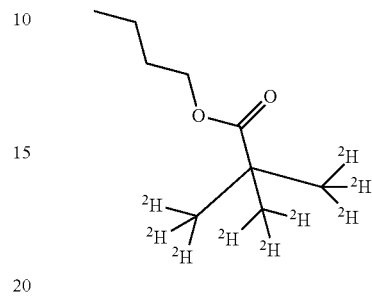

d$_9$-tert-Butylchloride (5.0 g) is added portion wise to a suspension of magnesium (1.50 g) in tetrahydrofuran (20 ml), activated with a catalytic amount of iodine, over 1 hour with heating as required to maintain a steady reflux. The reaction mixture is then heated for a further one hour to ensure complete Grignard formation. The above Grignard solution is then added dropwise to a solution of imidazole-1-carboxylic acid butyl ester (7.5 g, prepared as described by T. Werner and A. G. M. Barrett J. Org. Chem. 2006, 71, 4302-4304.) in tetrahydrofuran (40 ml) cooled with an ice bath. The reaction mixture is stirred for 18 hours at room temperature, water (200 ml) is added, the mixture is filtered through Hyflo, the filtrate is extracted with diethyl ether and the diethyl ether layers dried over sodium sulphate and evaporated to give the tile compound.

EXAMPLE 62

(S)-Pyrrolidine-1,2-dicarboxylic acid 2-amide 1-({4-methyl-5-[2-(2-methyl-cyclopropyl)-pyrimidin-4-yl]-thiazol-2-yl}-amide)

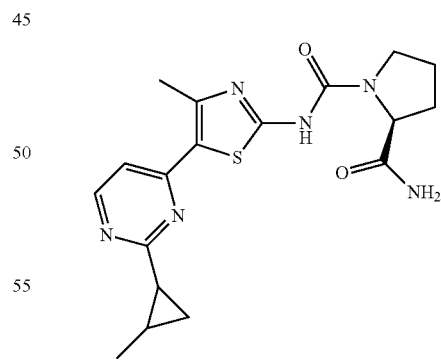

Imidazole-1-carboxylic acid {4-methyl-5-[2-(2-methyl-cyclopropyl)-pyrimidin-4-yl]-thiazol-2-yl}-amide (50 mg) is added to a stirred solution of L-proline amide (18 mg) and triethylamine (25 Å in DMF (147 μl) at room temperature. The reaction mixture is stirred at 40° C. for 2 hours and purified by preparative reversed phase chromatography. Fractions containing the title compound are captured with a 300 mg BondElut SPE, SCX cartridge and then released with 7M ammonia in methanol solution (1 ml). The title compound is obtained by evaporation. ESI-MS: M+H 387 and M−H 385.

Step 62.1: Imidazole-1-carboxylic acid {4-methyl-5-[2-(2-methyl-cyclopropyl)-pyrimidin-4-yl]-thiazol-2-yl}-amide

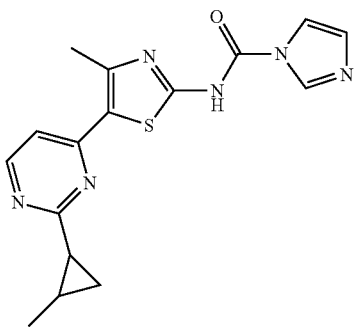 [SMILES: Cc1nc(NC(=O)n2ccnc2)sc1-c1ccnc(C2CC2C)n1]

Carbonyl diimidazole (487 mg) is added to a solution of 4-methyl-5-[2-(2-methyl-cyclopropyl)-pyrimidin-4-yl]-thiazol-2-ylamine (370 mg) and triethylamine (251 µl) in DMF (1.5 ml) at room temperature and then heated for 2 hours at 40° C. The reaction mixture is evaporated and triturated with chloroform. The title compound is isolated by filtration.

Step 62.2: 4-Methyl-5-[2-(2-methyl-cyclopropyl)-pyrimidin-4-yl]-thiazol-2-ylamine

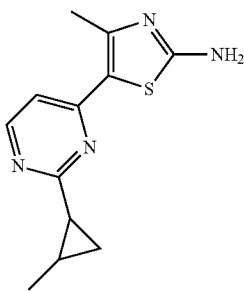 [SMILES: Cc1nc(N)sc1-c1ccnc(C2CC2C)n1]

Powdered sodium hydroxide (300 mg) is added to a solution of N'-[5-(3-dimethylamino-acryloyl)-4-methyl-thiazol-2-yl]-N,N-dimethyl-formamidine (1 g, prepared as described by S. Wang et al J. Med. Chem. 2004, 47, 1662-1675.) and cis/trans 2-methyl-cyclopropanecarboxamidine hydrochloride (0.61 g, prepared as described in WO 03/087064) in 2-methoxyethanol (3.8 ml) and the mixture heated at 125° C. for 1 hour with stirring. The reaction mixture is cooled, filtered, washing with water to give the title compound. MS: M+H 247 and M−H 245.

EXAMPLE 63

(S)-Pyrrolidine-1,2-dicarboxylic acid 2-amide 1-{[5-(2-diethylamino-pyrimidin-4-yl)-4-methyl-thiazol-2-yl]-amide}

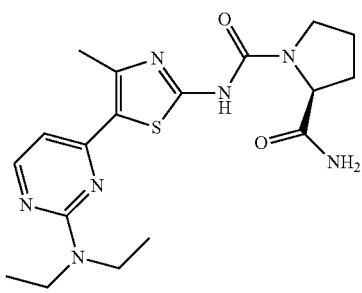 [SMILES: CCN(CC)c1nccc(-c2sc(NC(=O)N3CCC[C@H]3C(N)=O)nc2C)n1]

Imidazole-1-carboxylic acid [5-(2-diethylamino-pyrimidin-4-yl)-4-methyl-thiazol-2-yl]-amide (40 mg) is added to a stirred solution of L-proline amide (14 mg) and triethylamine (19 µl) in DMF (147 µl) at room temperature. The reaction mixture is stirred at 40° C. for 2 hours and purified by preparative reversed phase chromatography. Fractions containing the title compound are captured with a 300 mg BondElut SPE, SCX cartridge and then released with 7M ammonia in methanol solution (1 ml). The title compound is obtained by evaporation. ESI-MS: M+H 404 and M−H 402.

Step 63.1: Imidazole-1-carboxylic acid [5-(2-diethylamino-pyrimidin-4-yl)-4-methyl-thiazol-2-yl]-amide

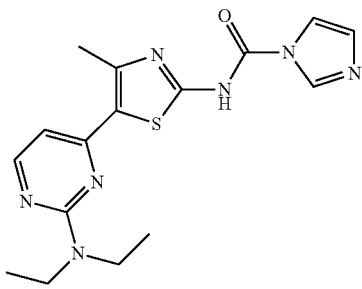 [SMILES: CCN(CC)c1nccc(-c2sc(NC(=O)n3ccnc3)nc2C)n1]

Carbonyl diimidazole (437 mg) is added to a solution of [4-(2-Amino-4-methyl-thiazol-5-yl)-pyrimidin-2-yl]-diethyl-amine (355 mg) and triethylamine (207 µl) in DMF (1.4 ml) at room temperature and then heated for 18 hours at 80°

C. The reaction mixture is evaporated and triturated with chloroform. The title compound is isolated by filtration.

Step 63.2: [4-(2-Amino-4-methyl-thiazol-5-yl)-pyrimidin-2-yl]-diethyl-amine

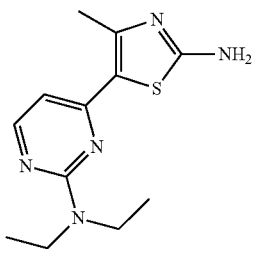 [SMILES: CCN(CC)c1nccc(-c2sc(N)nc2C)n1]

Powdered sodium hydroxide (150 mg) is added to a solution of N'-[5-(3-dimethylamino-acryloyl)-4-methyl-thiazol-2-yl]-N,N-dimethyl-formamidine (0.5 g, prepared as described by S. Wang et al J. Med. Chem. 2004, 47, 1662-1675.) and 1,1-diethylguanidine (259 mg) in 2-methoxyethanol (1.9 ml) and the mixture heated at 125° C. for 1 hour with stirring. The reaction mixture is concentrated under vacuum and purified by normal phase chromatography, eluent; DCM/EtOAc, to give the title compound. ESI-MS: M+H 264 and M−H 262.

EXAMPLE 64

(S)-Pyrrolidine-1,2-dicarboxylic acid 2-amide 1-({4-methyl-5-[2-(2,2,2-trifluoro-1,1-dimethyl-ethyl)-pyrimidin-4-yl]-thiazol-2-yl}-amide)

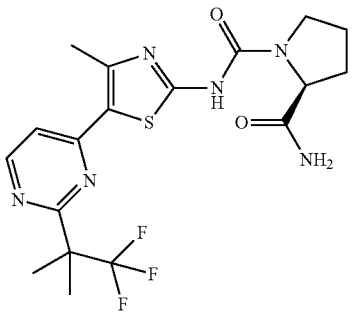 [SMILES: Cc1nc(NC(=O)N2CCC[C@H]2C(N)=O)sc1-c1ccnc(C(C)(C)C(F)(F)F)n1]

Imidazole-1-carboxylic acid {4-methyl-5-[2-(2,2,2-trifluoro-1,1-dimethyl-ethyl)-pyrimidin-4-yl]-thiazol-2-yl}-amide (69 mg) is added to a stirred solution of L-proline amide (22 mg) and triethylamine (53 mg) in DMF (1 ml) at room temperature. The reaction mixture is stood at room temperature for 22 hours, then evaporated and the title compound is obtained as a white solid after crystallization with methanol (2 ml) and water (1 ml). HPLC/MS: retention time 1.80 minutes, M+H 443.1 and M−H 441.2.

Step 64.1: Imidazole-1-carboxylic acid {4-methyl-5-[2-(2,2,2-trifluoro-1,1-dimethyl-ethyl)-pyrimidin-4-yl]-thiazol-2-yl}-amide

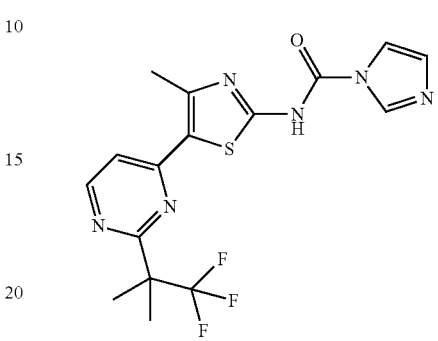

Carbonyl diimidazole (38 mg) is added to a solution of 4-methyl-5-[2-(2,2,2-trifluoro-1,1-dimethyl-ethyl)-pyrimidin-4-yl]-thiazol-2-ylamine (65 mg) in DCM (1 ml) and DMF (0.2 ml) at room temperature and then stood for 18 hours at 25° C. After cooling the title compound is isolated by filtration.

Step 64.2: 4-Methyl-5-[2-(2,2,2-trifluoro-1,1-dimethyl-ethyl)-pyrimidin-4-yl]-thiazol-2-ylamine

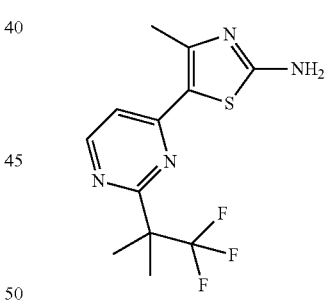

Powdered sodium hydroxide (0.42 g) is added to a solution of N'-[5-((E)-3-dimethylamino-acryloyl)-4-methyl-thiazol-2-yl]-N,N-dimethyl-formamidine (0.93 g, prepared as described by S. Wang et al J. Med. Chem. 2004, 47, 1662-1675.) and 3,3,3-trifluoro-2,2-dimethyl-propionamidine hydrochloride (0.54 g) in 2-methoxyethanol (7 ml) and the mixture is heated at 125° C. for 1 hour with stirring. The reaction mixture is cooled, water is added, and the aqueous layer is extracted 4-times with 10% methanol in dichloromethane. The combined organic layers are purified by reversed phase chromatography and sodium bicarbonate is added to the fractions containing the title compound to give a white precipitate, which is collected by filtration. HPLC/MS: retention time 1.47 minutes, M+H 303.1.

Step 64.3: 3,3,3-Trifluoro-2,2-dimethyl-propionamidine hydrochloride

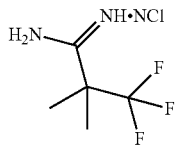

The title compound is synthesized following the procedure described in step 61.3 with the following modifications. 3,3,3-Trifluoro-2,2-dimethyl-propionic acid butyl ester is used instead of d9-2,2-dimethyl-propionic acid butyl ester and the mixture is stirred 3 days at 80° C. The crude product is taken up in DCM treated with a small amount of HCl in EtOH and evaporated. The residue is triturated with DCM, filtered and dried to give the title compound as an off-white solid.

Step 64.4: 3,3,3-Trifluoro-2,2-dimethyl-propionic acid butyl ester)

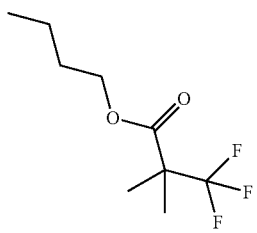

3,3,3-Trifluoro-2,2-dimethyl-propionic acid (3.0 g, 19.2 mmol) and a drop of DMF are dissolved in 30 mL of DCM and treated dropwise at RT with oxalyl chloride (1.85 mL, 21.1 mmol). After 2 h gas evolution ceases and the mixture is treated slowly with triethyl amine (5.36 mL, 38.4 mmol) followed by n-butanol (2.1 mL, 23 mmol). The mixture is stirred over night, the solvent evaporated and the residue stirred with hexanes. The solid is filtered off and the filtrate is evaporated to a brown-red oil. Kugelrohr distillation (10 mbar, 60-80° C. oven temperature) gives the title compound a colorless liquid.

EXAMPLE 65

(S)-Pyrrolidine-1,2-dicarboxylic acid 2-amide 1-{[2-(ethyl-methyl-amino)-pyrimidin-4-yl]-4-methyl-thiazol-2-yl}-amide)

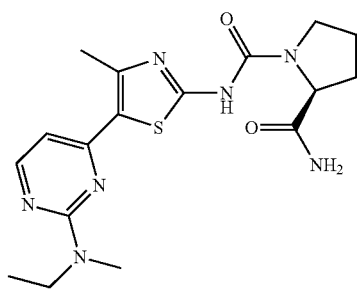 [SMILES: CCN(C)c1nccc(-c2sc(NC(=O)N3CCC[C@H]3C(N)=O)nc2C)n1]

A mixture of (S)-pyrrolidine-1,2-dicarboxylic acid 2-amide 1-{[5-(2-methanesulphinyl-pyrimidin-4-yl)-4-methyl-thiazol-2-yl]-amide} (60 mg) and N-ethylmethylamine (45 mg) is heated for 18 hours at 80° C. in a sealed tube. The crude product is then purified by preparative reversed phase chromatography. Fractions containing the title compound are captured with a 300 mg BondElut SPE, SCX cartridge and then released with 7M ammonia in methanol solution (1 ml). The title compound is obtained by evaporation. ESI-MS: M+H 390.

Step 65.1: (S)-Pyrrolidine-1,2-dicarboxylic acid 2-amide 1-{[5-(2-methanesulphinyl-pyrimidin-4-yl)-4-methyl-thiazol-2-yl]-amide}

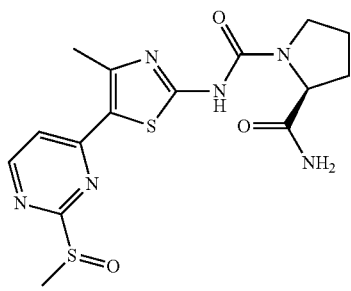 [SMILES: Cc1nc(NC(=O)N2CCC[C@H]2C(N)=O)sc1-c1ccnc(S(C)=O)n1]

meta-Chloroperoxybenzoic acid (0.50 g) was added to a solution of (S)-pyrrolidine-1,2-dicarboxylic acid 2-amide 1-{[4-methyl-5-(2-methylsulphanyl-pyrimidin-4-yl)-thiazol-2-yl]-amide} (1.7 g) in dichloromethane (8.5 ml) at 0° C. After 1 hour the reaction mixture is evaporated and purified by normal phase chromatography, eluting with a dichloromethane I methanol gradient, to give the title compound as a yellow solid. ESI-MS: M+H 395 and M−H 393.

Step 65.2: (S)-Pyrrolidine-1,2-dicarboxylic acid 2-amide 1-{[4-methyl-5-(2-methylsulphanyl-pyrimidin-4-yl)-thiazol-2-yl]-amide}

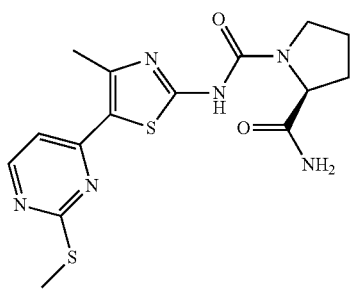 [SMILES: CSc1nccc(-c2sc(NC(=O)N3CCC[C@H]3C(N)=O)nc2C)n1]

Imidazole-1-carboxylic acid [4-methyl-5-(2-methylsulphanyl-pyrimidin-4-yl)-thiazol-2-yl]-amide (1.0 g) is added to a stirred solution of L-proline amide (379 mg) and triethylamine (0.51 ml) in DMF (3 ml) at room temperature. The reaction mixture is stirred at 40° C. for 2 hours, then evaporated and the title compound is obtained as an orange solid after precipitation with dichloromethane and water. ESI-MS: M+H 379 and M−H 377.

Step 65.3: Imidazole-1-carboxylic acid [4-methyl-5-(2-methylsulphanyl-pyrimidin-4-yl)-thiazol-2-yl]-amide

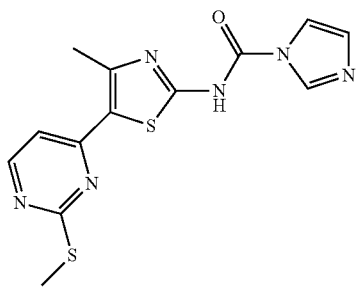 [SMILES: CSc1nccc(-c2sc(NC(=O)n3ccnc3)nc2C)n1]

Carbonyl diimidazole (1.77 g) is added to a solution of 4-methyl-5-(2-methylsulphanyl-pyrimidin-4-yl)-thiazol-2-ylamine (1.3 g) in triethylamine (0.84 ml) and DMF (5.5 ml) at room temperature and stirred for 2 hours at 80° C. After cooling the title compound is isolated by filtration.

Step 65.4: 4-Methyl-5-(2-methylsulphanyl-pyrimidin-4-yl)-thiazol-2-ylamine

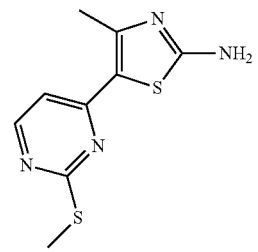

Powdered sodium hydroxide (1.09 g) is added to a solution of N'-[5-(3-dimethylamino-acryloyl)-4-methyl-thiazol-2-yl]-N,N-dimethyl-formamidine (2.0 g, prepared as described by S. Wang et al J. Med. Chem. 2004, 47, 1662-1675.) and thiourea (0.57 g) in ethanol (25 ml) and the mixture is heated at reflux for 3 hour with stirring. The reaction mixture is cooled to room temperature and water then methyliodide (0.47 ml) is added. After 1 hour at room temperature the ethanol is removed by evaporation and water is added and the pH is adjusted to 7 with 2N aqueous hydrochloric acid. The title compound is then obtained by filtration. ESI-MS: M+H 239 and M−H 237.

EXAMPLE 66

(5)-Pyrrolidine-1,2-dicarboxylic acid 2-amide 1-{[5-(6-cyclopropyl-pyrazin-2-yl)-4-methyl-thiazol-2-yl]-amide}

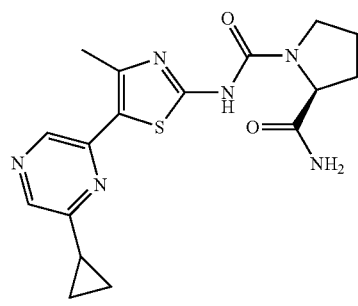 [SMILES: Cc1nc(NC(=O)N2CCC[C@H]2C(N)=O)sc1-c1cncc(C2CC2)n1]

Imidazole-1-carboxylic acid [5-(6-cyclopropyl-pyrazin-2-yl)-4-methyl-thiazol-2-yl]amide (78 mg) is added to a stirred solution of L-proline amide (30 mg) and triethylamine (83 μl) in DMF (1 ml) at room temperature. The reaction mixture is stood at room temperature for 18 hours, evaporated and the title compound is obtained as a yellow/white solid after crystallization with methanol (1 ml) and water (0.5 ml). HPLC/MS: retention time 1.40 minutes, M+H 373.1 and M−H 371.3.

Step 66.1: Imidazole-1-carboxylic acid [5-(6-cyclopropyl-pyrazin-2-yl)-4-methyl-thiazol-2-yl]-amide

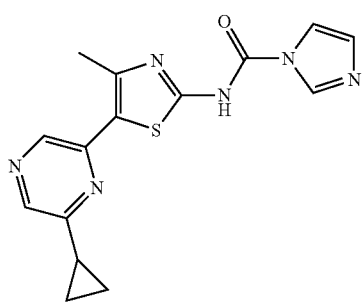 [SMILES: Cc1nc(NC(=O)n2ccnc2)sc1-c1cncc(C2CC2)n1]

Carbonyl diimidazole (74 mg) is added to a solution of 5-(6-cyclopropyl-pyrazin-2-yl)-4-methyl-thiazol-2-ylamine (96 mg) in DMF (2 ml) at room temperature and stood for 18 hours at room temperature. The reaction mixture is filtered, washing with dichloromethane, to give the title compound.

Step 66.2: 5-(6-Cyclopropyl-pyrazin-2-yl)-4-methyl-thiazol-2-ylamine

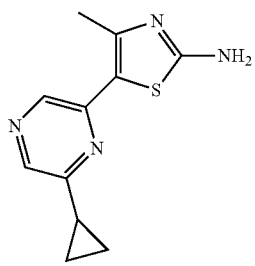 [SMILES: Cc1nc(N)sc1-c1cncc(C2CC2)n1]

Concentrated hydrochloric acid (0.4 ml) is added to N-[5-(6-cyclopropyl-pyrazin-2-yl)-4-methyl-thiazol-2-yl]-acetamide (120 mg) in ethanol (9 ml) at room temperature and the mixture is heated at reflux for 18 hours. The cooled reaction mixture is evaporated, neutralized with aqueous sodium hydrogen carbonate and extracted with 10% methanol in DCM. The combined organic extracts are dried over sodium sulphate and evaporated to give the title compound. HPLC/MS: retention time 0.93 minutes, M+H 233.3.

Step 66.3: N-[5-(6-Cyclopropyl-pyrazin-2-yl)-4-methyl-thiazol-2-yl]-acetamide

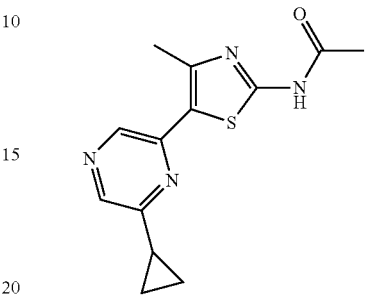

Argon is bubbled through a mixture of 2-cyclopropyl-6-chloropyrazine (154 mg, prepared by the method of A. Fürstner et al J. Am. Chem. Soc. 2002, 214, 13856-13863.), 2-acetamido-4-methylthiazole (200 mg), palladium acetate (24 mg), tri-tert-butylphosphonium tetrafluoroborate (61 mg) and cesium carbonate (678 mg) in DMF (3 ml) at room temperature for 5 minutes. The reaction mixture is heated in a sealed vial under an argon atmosphere for 45 minutes at 150° C. in a Biotage Initiator™ microwave apparatus. The reaction mixture is filtered and purified by preparative HPLC. Fractions containing the title compound are combined and evaporated to remove acetonitrile and the title compound obtained as a beige solid by filtration. HPLC/MS: retention time 1.65 minutes, M+H 275.3.

EXAMPLE 67

(S)-Pyrrolidine-1,2-dicarboxylic acid 2-amide 1-{[4-methyl-5-(5-trifluoromethyl-pyridin-3-yl)-thiazol-2-yl]-amide}

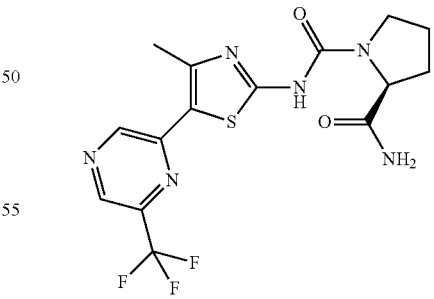

Carbonyl diimidazole (29 mg) is added to a stirred solution of 4-methyl-5-(5-trifluoromethyl-pyridin-3-yl)-thiazol-2-ylamine (42 mg) and triethylamine (50 μl) in DMF (1 ml) at room temperature and the mixture is stood for 18 hours at room temperature. L-Proline amide (20 mg) is added and the reaction mixture is stood for a further 8 hours at room temperature, evaporated and the title compound is obtained as a white solid after crystallization with methanol (3 ml) and water (1.5 ml). ESI-MS: M+H 400.

Step 67.1: 4-Methyl-5-(5-trifluoromethyl-pyridin-3-yl)-thiazol-2-ylamine

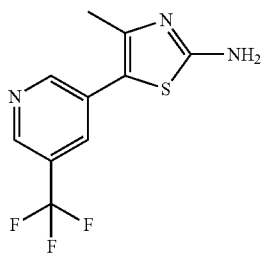 [SMILES: Cc1nc(N)sc1-c1cncc(C(F)(F)F)c1]

Trimethylsilyl chloride (0.3 ml) is added to N-[4-methyl-5-(5-trifluoromethyl-pyridin-3-yl)-thiazol-2-yl]-acetamide (44 mg) in ethanol (2 ml) at room temperature and the mixture is stirred at room temperature for 4.5 hours. The reaction is then heated at 50° C. for 18 hours, cooled, evaporated and the title compound is obtained by filtration after trituration with diethyl ether.

Step 67.2: N-[4-Methyl-5-(5-trifluoromethyl-pyridin-3-yl)-thiazol-2-yl]-acetamide

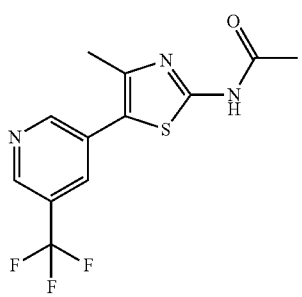 [SMILES: CC(=O)Nc1nc(C)c(-c2cncc(C(F)(F)F)c2)s1]

Argon is bubbled through a mixture of 5-(trifluoromethyl)-3-pyridinylboronic acid hydrochloride (263 mg, prepared as described in WO 2007/134828.), 2-acetylamino-5-iodo-4-methylthiazole (260 mg, prepared as described in WO 2006/125807), 1,1″-bis-(diphenylphosphino)-ferrocenedichloro palladium (II) (38 mg), sodium carbonate (488 mg) in DME (2.3 ml) and water (2.3 ml) at room temperature for 5 minutes. The reaction mixture is heated in a sealed vial under an argon atmosphere for 30 minutes at 80° C., and then for 60 minutes at 80° C., in a Biotage Initiator™ microwave apparatus. After cooling the reaction mixture is extracted with DCM, the combined organic layers evaporated with silica gel and purified by normal phase chromatography (eluent; gradient from DCM to 1:1 DCM:ethyl acetate). The product containing fractions are then triturated with methanol (5 ml), DMF (0.3 ml) and water (1.3 ml) and filtered to give the title compound as a beige solid.

EXAMPLE 68

(S)-Pyrrolidine-1,2-dicarboxylic acid 2-amide 1-{[5-(6-d$_{10}$-diethylamino-pyrazin-2-yl)-4-methyl-thiazol-2-yl]-amide}

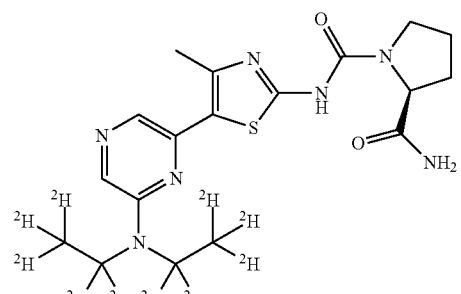

Imidazole-1-carboxylic acid [5-(6-d$_{10}$-diethylamino-pyrazin-2-yl)-4-methyl-thiazol-2-yl]-amide (82 mg) is added to a stirred solution of L-proline amide (28 mg) and triethylamine (78 µl) in DMF (1 ml) at room temperature. The reaction mixture is stood at room temperature for 14 hours, evaporated and the title compound is obtained as a yellow/white solid after crystallization with methanol (1 ml) and water (0.5 ml). HPLC/MS: retention time 1.41 minutes, M+H 414.2 and M−H 412.3.

Step 68.1: Imidazole-1-carboxylic acid [5-(6-d$_{10}$-diethylamino-pyrazin-2-yl)-4-methyl-thiazol-2-yl]-amide

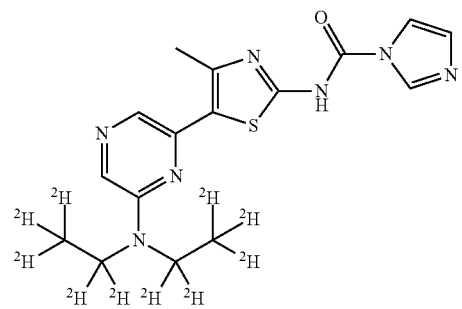 [SMILES: [2H]C([2H])([2H])C([2H])([2H])N(c1cncc(-c2sc(NC(=O)n3ccnc3)nc2C)n1)C([2H])([2H])C([2H])([2H])[2H]]

Carbonyl diimidazole (78 mg) is added to a solution of 5-(6-d$_{10}$-diethylamino-pyrazin-2-yl)-4-methyl-thiazol-2-ylamine (121 mg) in DMF (2 ml) at room temperature and stood for 3.5 hours at room temperature. The reaction mixture is filtered, washing with dichloromethane, to give the title compound.

Step 68.2: 5-(6-$d_{10}$-diethylamino-pyrazin-2-yl)-4-methyl-thiazol-2-ylamine

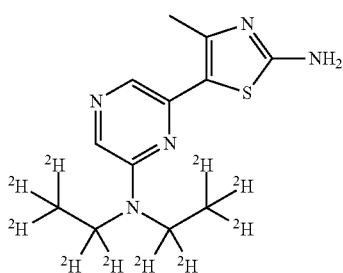 [SMILES: [2H]C([2H])([2H])C([2H])([2H])N(c1cncc(-c2sc(N)nc2C)n1)C([2H])([2H])C([2H])([2H])[2H]]

Concentrated hydrochloric acid (0.4 ml) is added to N-[5-(6-$d_{10}$-diethylamino-pyrazin-2-yl)-4-methyl-thiazol-2-yl]-acetamide (140 mg) in ethanol (9 ml) at room temperature and the mixture is heated at reflux for 40 hours. The cooled reaction mixture is evaporated, neutralized with aqueous sodium hydrogen carbonate and extracted with 10% methanol in DCM. The combined organic extracts are dried over sodium sulphate and evaporated to give the title compound. HPLC/MS: retention time 1.17 minutes, M+H 274.4.

Step 68.3: N-[5-(6-$d_{10}$-diethylamino-pyrazin-2-yl)-4-methyl-thiazol-2-yl]-acetamide

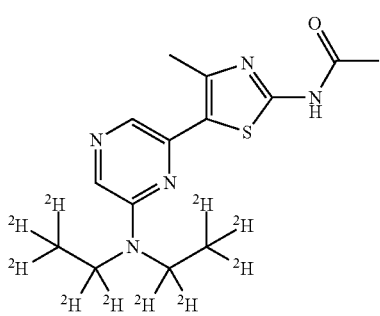 [SMILES: [2H]C([2H])([2H])C([2H])([2H])N(c1cncc(-c2sc(NC(C)=O)nc2C)n1)C([2H])([2H])C([2H])([2H])[2H]]

Argon is bubbled through a mixture of 2-$d_{10}$-diethylamino-6-chloropyrazine (293 mg), 2-acetamido-4-methylthiazole (300 mg), palladium acetate (24 mg), tri-tert-butylphosphonium tetrafluoroborate (61 mg) and cesium carbonate (1.02 g) in DMF (3 ml) at room temperature for 5 minutes. The reaction mixture is heated in a sealed vial under an argon atmosphere for 45 minutes at 150° C. in a Biotage Initiator™ microwave apparatus, filtered and purified by preparative HPLC. Fractions containing the title compound are combined and evaporated to remove acetonitrile and the title compound obtained as a beige solid by filtration. HPLC/MS: retention time 1.68 minutes, M+H 316.3.

Step 68.4: 2-$d_{10}$-diethylamino-6-chloropyrazine $d_{10}$-Diethylamine (0.5 g) is added to a stirred mixture of 2,6-dichloropyrazine (0.93 g) and potassium carbonate (1.41 g) in acetonitrile (4 ml) at room temperature. The reaction mixture is then heated at 55° C. for 60 hours, cooled, water is added and then extracted with dichloromethane. The combined organic extracts are dried over sodium sulphate, evaporated and purified by normal phase chromatography, eluent DCM, to give the title compound. HPLC/MS: retention time 2.10 minutes, M+H 196.4 and 198.4.

EXAMPLE 69

(S)-Pyrrolidine-1,2-dicarboxylic acid 2-amide 1-{[5-(6-diethylamino-pyrazin-2-yl)-4-methyl-thiazol-2-yl]-amide}

The title compound is prepared in analogy to the procedure described in Example 68, but using diethylamine in place of $d_{10}$-diethylamine. HPLC/MS: retention time 1.43 minutes, M+H 404.2 and 402.3.

EXAMPLE 70

(S)-Pyrrolidine-1,2-dicarboxylic acid 2-amide 1-{[5-(2-cyclopropylmethyl-pyrimidin-4-yl)-4-methyl-thiazol-2-yl]-amide}

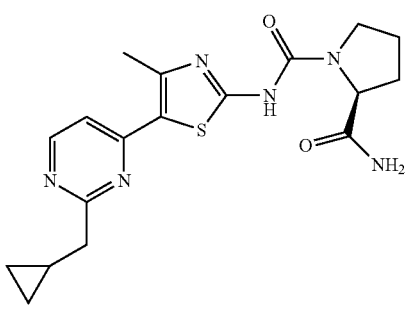 [SMILES: Cc1nc(NC(=O)N2CCC[C@H]2C(N)=O)sc1-c1ccnc(CC2CC2)n1]

The title compound is prepared in analogy to the procedure described in Example 42, but using imidazole-1-carboxylic acid [5-(2-cyclopropylmethyl-pyrimidin-4-yl)-4-methyl-thiazol-2-yl]-amide in place of imidazole-1-carboxylic acid {4-methyl-5-[2-(1-methyl-cyclopropyl)-pyrimidin-4-yl]-thiazol-2-yl}-amide. M.p. 220-222° C., ESI-MS [M+H]$^+$ 387.1, TLC: R$_f$=0.2 (DCM/EtOH 95:5)

Step 70.1: Imidazole-1-carboxylic acid [5-(2-cyclopropylmethyl-pyrimidin-4-yl)-4-methyl-thiazol-2-yl]-amide

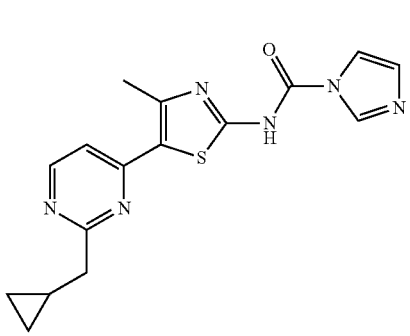 [SMILES: Cc1nc(NC(=O)n2ccnc2)sc1-c1ccnc(CC2CC2)n1]

The title compound is prepared in analogy to the procedure described in Step 42.1, but using 5-(2-cyclopropylmethyl-pyrimidin-4-yl)-4-methyl-thiazol-2-ylamine in place of 4-methyl-5-[2-(1-methyl-cyclopropyl)-pyrimidin-4-yl]-thiazol-2-ylamine and the reaction is stirred for 15 h. M.p. 240-243° C., ESI-MS [M+H]$^+$305.1, TLC: R$_f$=0.35 (DCM/EtOH 95:5).

Step 70.2: 5-(2-Cyclopropylmethyl-pyrimidin-4-yl)-4-methyl-thiazol-2-ylamine

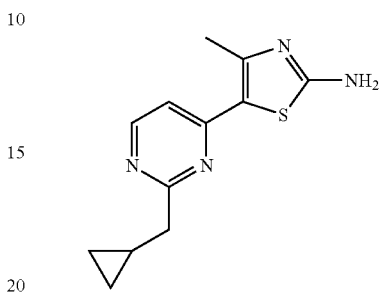

The title compound is prepared in analogy to the procedure described in Step 42.2, but using 2-cyclopropyl-acetamidine hydrochloride in place of 1-methyl-cyclopropanecarboxamidine hydrochloride. M.p. 198-200° C., ESI-MS [M+H]$^+$ 247.1, TLC: R$_f$=0.25 (DCM/EtOH 95:5).

EXAMPLE 71

(S)-Pyrrolidine-1,2-dicarboxylic acid 2-amide 1-({5-[2-(2-fluoro-1,1-dimethyl-ethyl)-pyrimidin-4-yl]-4-methyl-thiazol-2-yl}-amide)

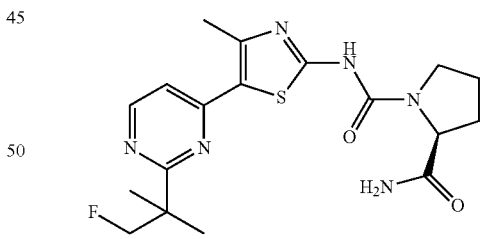

The title compound is prepared in analogy to the procedure described in Example 42, but using imidazole-1-carboxylic acid {5-[2-(2-fluoro-1,1-dimethyl-ethyl)-pyrimidin-4-yl]-4-methyl-thiazol-2-yl}-amide in place of imidazole-1-carboxylic acid {4-methyl-5-[2-(1-methyl-cyclopropyl)-pyrimidin-4-yl]-thiazol-2-yl}-amide. M.p. 187-190° C., ESI-MS [M+H]⁺407.1, TLC: $R_f$=0.3 (DCM/EtOH 95:5)

Step 71.1: Imidazole-1-carboxylic acid {5-[2-(2-fluoro-1,1-dimethyl-ethyl)-pyrimidin-4-yl]-4-methyl-thiazol-2-yl}-amide

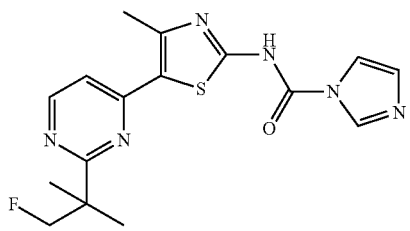 [SMILES: Cc1nc(NC(=O)n2ccnc2)sc1-c1ccnc(C(C)(C)CF)n1]

The title compound is prepared in analogy to the procedure described in Step 42.1, but using 5-[2-(2-fluoro-1,1-dimethyl-ethyl)-pyrimidin-4-yl]-4-methyl-thiazol-2-ylamine in place of 4-methyl-5-[2-(1-methyl-cyclopropyl)-pyrimidin-4-yl]-thiazol-2-ylamine and the reaction is stirred for 16 h at 80° C.

Step 71.2: 5-[2-(2-fluoro-1,1-dimethyl-ethyl)-pyrimidin-4-yl]-4-methyl-thiazol-2-ylamine

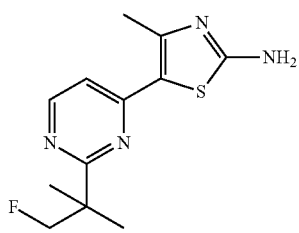 [SMILES: Cc1nc(N)sc1-c1ccnc(C(C)(C)CF)n1]

The title compound is prepared in analogy to the procedure described in Step 42.2, but using 3-fluoro-2,2-dimethyl-propionamidine hydrochloride in place of 1-methyl-cyclopropane-carboxamidine hydrochloride. ESI-MS [M+H]⁺267.1, TLC: $R_f$=0.4 (DCM/EtOH 95:5).

EXAMPLE 72

(S)-Pyrrolidine-1,2-dicarboxylic acid 2-amide 1-{[5-(2-tert-butyl-6-methyl-pyrimidin-4-yl)-4-methyl-thiazol-2-yl]-amide}

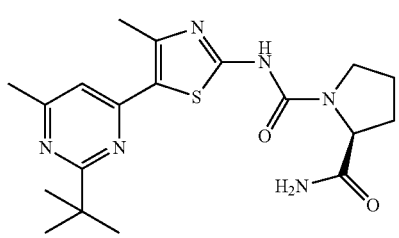 [SMILES: Cc1cc(-c2sc(NC(=O)N3CCC[C@H]3C(N)=O)nc2C)nc(C(C)(C)C)n1]

The title compound is prepared in analogy to the procedure described in Example 42, but using imidazole-1-carboxylic acid [5-(2-tert-butyl-6-methyl-pyrimidin-4-yl)-4-methyl-thiazol-2-yl]-amide in place of imidazole-1-carboxylic acid {4-methyl-5-[2-(1-methyl-cyclopropyl)-pyrimidin-4-yl]-thiazol-2-yl}-amide. M.p. 197-199° C., ESI-MS [M+H]⁺ 403.1, TLC: $R_f$=0.3 (DCM/EtOH 95:5)

Step 72.1: Imidazole-1-carboxylic acid [5-(2-tert-butyl-6-methyl-pyrimidin-4-yl)-4-methyl-thiazol-2-yl]-amide

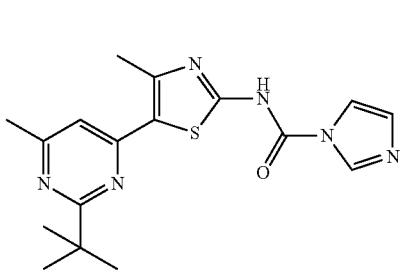 [SMILES: Cc1cc(-c2sc(NC(=O)n3ccnc3)nc2C)nc(C(C)(C)C)n1]

The title compound is prepared in analogy to the procedure described in Step 42.1, but using 5-(2-tert-butyl-6-methyl-pyrimidin-4-yl)-4-methyl-thiazol-2-ylamine in place of 4-methyl-5-[2-(1-methyl-cyclopropyl)-pyrimidin-4-yl]-thiazol-2-ylamine and the reaction is stirred for 16 h. ESI-MS [M−H]⁻, 355.2.

Step 72.2: 5-(2-tert-Butyl-6-methyl-pyrimidin-4-yl)-4-methyl-thiazol-2-ylamine

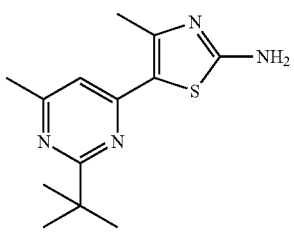 [SMILES: Cc1cc(-c2sc(N)nc2C)nc(C(C)(C)C)n1]

The title compound is prepared in analogy to the procedure described in Step 1.2, but using N-[5-(2-tert-butyl-6-methyl-pyrimidin-4-yl)-4-methyl-thiazol-2-yl]-acetamide in place of N-[5-(2-tert-butyl-pyridin-4-yl)-4-methyl-thiazol-2-yl]-acetamide and using 2 N HCl. The reaction mixture is stirred 16 h at RT and then 3 h at 90° C. ESI-MS [M+H]⁺263.1.

Step 72.3: N-[5-(2-tert-butyl-6-methyl-pyrimidin-4-yl)-4-methyl-thiazol-2-yl]-acetamide

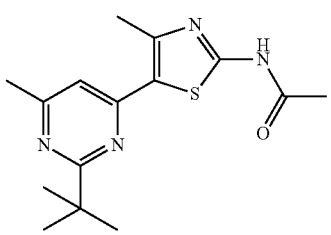 [SMILES: CC(=O)Nc1nc(C)c(-c2cc(C)nc(C(C)(C)C)n2)s1]

The title compound is prepared in analogy to the procedure described in Step 1.3, but using 4-bromo-2-tert-butyl-6-methyl-pyrimidine in place of 4-bromo-2-tert-butyl-pyridine. ESI-MS [M+H]$^+$ 305.2.

Step 72.4:
4-Bromo-2-tert-butyl-6-methyl-pyrimidine

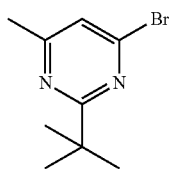

The title compound is prepared in analogy to the procedure described in Step 1.4, but using 2-tert-butyl-6-methyl-3H-pyrimidin-4-one in place of 2-tert-butyl-1H-pyridin-4-one. ESI-MS [M+H]$^+$ 229/231.0. TLC: R$_f$=0.58 (Hexanes/DCM 7:3)

EXAMPLE 73

(S)-Pyrrolidine-1,2-dicarboxylic acid 2-amide 1-({5-[2-(2-fluoro-1,1-dimethyl-ethyl)-pyridin-4-yl]-4-methyl-thiazol-2-yl}-amide)

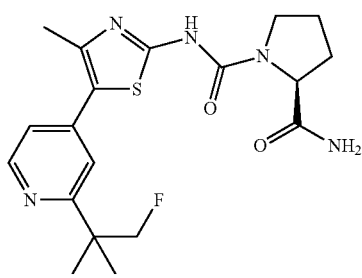 [SMILES: Cc1nc(NC(=O)N2CCC[C@H]2C(N)=O)sc1-c1ccnc(C(C)(C)CF)c1]

The title compound is prepared in analogy to the procedure described in Example 1 but with the following modifications. In Example 1, the reaction mixture is stirred for 6 h at rt. In Step 1.1, the reaction mixture is stirred for 15 h at reflux. In Step 1.2, the reaction mixture is stirred for 1 h at 100° C. and extracted with EtOAc after being quenched. In Step 1.3, the reaction mixture is stirred for 4 h at 120° C. In Step 1.4, the reaction mixture is stirred for 30 min at 85° C. and extracted with EtOAc after being quenched. In Step 1.5, the reaction mixture is stirred for 1 h at 70° C. and trituration in MeOH is not performed. In Step 1.6, the crude product is not purified. In Step 1.7, 3-fluoro-2,2-dimethyl-propionyl chloride (Step 76.1) is used.

Title compound: ESI-MS: 406.1 [M+H]$^+$; t$_R$=2.20 min (System 1); TLC: R$_f$=0.47 (DCM/MeOH, 9:1).

Step 73.1: 3-Fluoro-2,2-dimethyl-propionyl chloride

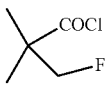

The title compound is prepared in analogy to the procedure described in Step 5.1 but using 3-fluoro-2,2-dimethyl-propionic acid (Step 73.2).

Step 73.2: 3-Fluoro-2,2-dimethyl-propionic acid

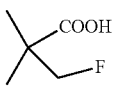

A solution of 6.9 g (38.6 mmol) 3-fluoro-2,2-dimethyl-propionic acid methyl ester in 30 mL of methanol is treated with 38.6 mL (77 mmol) 2N NaOH and the mixture heated to reflux for 3 hours. The mixture is cooled to RT and the solvent evaporated. The residue is partitioned between water and DCM. The aqueous phase is acidified by the addition of 50 mL of 2N HCl and extracted with ethyl acetate. The organic phase is washed with brine, dried with sodium sulfate and evaporated. The colorless residue is stirred with hexanes, insoluble material is removed by filtration and the filtrate is evaporated to give the title compound as a colorless solid. ESI-MS: 119.0 [M−H]$^-$.

Step 73.3: 3-Fluoro-2,2-dimethyl-propionic acid methyl ester

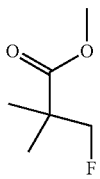

27 mL of a 1 M solution of tetrabutylammonium fluoride in THF are added slowly and under ice cooling to a solution of 7.25 g (27.4 mmol) 2,2-dimethyl-3-trifluoromethanesulfonyloxy-propionic acid methyl ester in 150 mL of THF. The resulting solution is stirred 6 h at 0° C. and then 10 h at RT. The solvent is evaporated carefully and the residue partitioned between DCM and brine. The organic phase is washed with brine, dried with sodium sulfate and evaporated carefully. The brown oil is distilled in a Kugelrohr-oven (oven temperature 120 to 150° C.) to give the title compound as a colorless liquid.

Step 73.4: 2,2-Dimethyl-3-trifluoromethanesulfonyloxy-propionic acid methyl ester

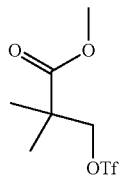

To a solution of 3.64 g (27.5 mmol) 3-hydroxy-2,2-dimethyl-propionic acid methyl ester and 4.82 mL (41.3 mmol) 2,6-lutidine in 50 mL dry DCM is slowly added trifluoromethanesulfonic acid anhydride (5.12 mL, 30.3 mmol) at −70° C. and under nitrogen. The yellow solution is stirred 5 min. at −70° C. then the cooling bath is removed and the mixture stirred 3 h at RT. Color change from yellow to orange to brown. DCM (50 mL) is added and the solution is washed twice with 2 N HCl, dried with sodium sulfate and evaporated to dryness. The brown residue is dried under vacuum and the title compound used without further purification. TLC: $R_f$=0.72 (EtOAc/hexanes 1:2).

Analytical HPLC Conditions:
Linear gradient 20-100% solvent A in 5 min+1.5 min 100% solvent A; detection at 215 nm, flow rate 1 mL/min at 30° C. Column: Nucleosil 100-3 C18 (70×4.0 mm). Solvent A=CH$_3$CN+0.1% TFA; Solvent B=H$_2$O+0.1% TFA.

MS Conditions:
Instrument: Micromass Platform II, eluent: 15% methanol in water containing 0.2% of a 25% ammonium hydroxide solution $^1$H-NMR spectra were measured on a Varian Mercury 400 Spectrometer in the indicated solvents. Abbreviations: br: broad; s: singlet; d: doublet; t: triplet; q: quartet; ppm: part per million HPLC/MS Conditions:
Instrument: Hewlett Packard Agilent 1100 series, column: XBridge™ C18 2.5 microm 3.0×30 mm, temperature: 50° C., eluent: 2 channel system: Channel A 5% acetonitrile in water, Channel B acetonitrile containing 1.0% formic acid

| Time (minutes) | % channel B | Flow (ml/minute) |
|---|---|---|
| 0 | 5 | 1.4 |
| 3.7 | 95 | 1.4 |
| 4.4 | 95 | 2.4 |
| 4.45 | 95 | 2.4 | detection: Agilent 1100 DAD 210-350 nm and Waters Micronnass ZQ 2000 ESI+ and ESI−.

Preparative HPLC:
Instrument: Gilson preparative HPLC system, column: Sunfire™ Prep C18 OBD™ 5 microm 30×100 mm, temperature: 25° C., eluent: gradient from 5-100% acetonitrile in 0.05% aqueous trifluoroacetic acid over 20 minutes, flow rate: 30 ml/minute, detection: UV 254 nm.

Abbreviations and Acronyms:
BBr$_3$ boron tribromide
$^t$BuP.HBF$_4$ tri-tert-butylphosphinium tetrafluoroborate
DCM dichloromethane
DIEA diisopropylethylamine
DMAP 4-(dimethylamino)pyridine
DME 1,2-dimethoxyethane
DMF dimethyl formamide
DMP 1,3-dimethyl-3,4,5,6-tetrahydro-2-(1H)-pyrimidinone
DMSO dimethylsulfoxide
Hex hexane
L liter(s)
LiHMDS lithium bis(trimethylsilyl)amide
m.p. melting point
MPLC medium pressure liquid chromatography
NBS N-bromosuccinimide
NMP 1-methyl-2-pyrrolidone
PdCl$_2$(dppf) [1,1'-bis(diphenylphosphino)ferrocene]dichloropalladium(II)
Pd(PPh$_3$)$_4$ tetrakis(triphenylphosphine)palladium(0)
R$_f$ ratio of fronts (TLC)
rt room temperature
TFA Trifluoroacetic acid
THF tetrahydrofuran
TLC thin layer chromatography
$t_R$ time of retention
v volume
wt. weight

EXAMPLE A

Efficiency as PI3 Kinase Inhibitors

PI3K KinaseGlo Assay:
50 mL of compound dilutions were dispensed onto black 384-well low volume Non Binding Styrene (NBS) plates (Costar Cat. No. NBS#3676). L-a-phosphatidylinositol (PI), provided as 10 mg/ml solution in methanol, was transferred into a glass tube and dried under nitrogen beam. It was then resuspended in 3% OctylGlucoside (OG) by vortexing and stored at 4° C. The KinaseGlo Luminescent Kinase Assay (Promega, Madison, Wis., USA) is a homogeneous HTS method of measuring kinase activity by quantifying the amount of ATP remaining in solution following a kinase reaction.

5 µL of a mix of PI/OG with the PI3K subtype were added (Table 1). Kinase reactions were started by addition of 5 µl of ATP-mix containing in a final volume 10 µL 10 mM TRIS-HCl pH 7.5, 3 mM MgCl$_2$, 50 mM NaCl, 0.05% CHAPS, 1 mM DTT and 1 µM ATP, and occurred at room temperature. Reactions were stopped with 10 µl of KinaseGlo and plates were read 10 mins later in a Synergy2 reader using an integration time of 0.1 seconds per well. 2.5 µM of a pan-class 1 PI3 kinase inhibitor (standard) was added to the assay plates to generate the 100% inhibition of the kinase reaction, and the 0% inhibition was given by the solvent vehicle (90% DMSO in water). The standard was used as a reference compound and included in all assay plates in the form of 16 dilution points in duplicate.

TABLE 1

PI3Ks by KinaseGlo: assay conditions and reagent protocol

| Vol (10 µL) | Enzyme (nM) | ATP (µM) | PI/OG (µM/ µg/ml) | NaCl (mM) | Mg$^{2+}$ (mM) | CHAPS (%) | DTT (mM) | time (mins) |
|---|---|---|---|---|---|---|---|---|
| PI3Kα | 10 | 1 | 11/10 | 50 | 3 | 0.05 | 1 | 30 |
| PI3Kβ | 25 | 1 | 11/10 | 50 | 3 | 0.05 | 1 | 30 |
| PI3Kγ | 150 | 1 | 22/20 | 50 | 3 | 0.05 | 1 | 90 |
| PI3Kd | 10 | 1 | 11/10 | 50 | 3 | 0.05 | 1 | 30 |

Cloning of PI3Ks

The PI3Kα, P13Kβ and PI3Kδ constructs are fusion of p85α iSH2 domain and the respective p110 isoforms. The p85α fragment and p110 isoform genes were generated by PCR from first strand cDNA generated by RT-PCR from commercial RNA from placenta, testis and brain as described below. The PI3Kγ construct was obtained from Roger Williams lab, MRC Laboratory of Molecular Biology, Cambridge, UK (November, 2003) and is described (Pacold, Michael E.; Suire, Sabine; Perisic, Olga; Lara-Gonzalez, Samuel; Davis, Colin T.; Walker, Edward H.; Hawkins, Phillip T.; Stephens, Len; Eccleston, John F.; Williams, Roger L. Crystal structure and functional analysis of Ras binding to its effector phosphoinositide 3-kinase gamma. Cell (2000), 103 (6), 931-943).

PI3Kα Constructs and Proteins

```
PI3Kα wt BV1075 p85iSH2(461-568)-GGGGGGGGGGGG-p110α(21-1068)-His
```

BV1075: The construct for Baculovirus BV-1075 was generated by a three-part ligation comprised of a p85 fragment and a p110α fragment cloned into vector pBlueBac4.5. The p85 fragment was derived from plasmid p1661-2 digested with Nhe/Spe. The p110α fragment derived from is clone was verified by sequencing and used in a LR410 as a SpeI/HindIII fragment. For the generation of the baculovirus expression vector LR410 the gateway LR reaction to transfer the insert into the Gateway adapted pBlueBac4.5 (Invitrogen) vector was used. The cloning vector pBlueBac4.5 (Invitrogen) was digested with Nhe/HindIII. This resulted in the construct PED 153.8. The p85 component (iSH2) was generated by PCR using ORF 318 (described above) as a template and one forward primer KAC1028 (5'-GCTAGCATGCGAGAATAT-GATAGAT-TATATGAAG-AATATACC) (SEQ ID NO: 1) and two reverse primers, KAC1029 (5'-GCCTCCACCAC-CTCCGCCTG-GTTTAATGCTGTTCATACGTTTGTC) (SEQ ID NO: 2) and KAC1039 (5'-TACTAGTC-CGCCTC-CAC-CACCTCCGCCTCCACCACCTCCGCC) (SEQ ID NO: 3). The two reverse primers overlap and incorporate the 12× Gly linker and the N-terminal sequence of the p110α gene to the SpeI site. The 12× Gly linker replaces the single Gly linker in the BV1052 construct. The PCR fragment was cloned into pCR2.1 TOPO (Invitrogen). Of the resulting clones, p1661-2 was determined to be correct by sequencing. This plasmid was digested with Nhe and SpeI and the resulting fragment was gel-isolated and purified for sub-cloning.

The p110α cloning fragment was generated by enzymatic digest of clone LR410 (see above) with Spe I and HindIII. The SpeI site is in the coding region of the p110α gene. The resulting fragment was gel-isolated and purified for sub-cloning. The cloning vector, pBlueBac4.5 (Invitrogen) was prepared by enzymatic digestion with Nhe and HindIII. The cut vector was purified with Qiagen column and then dephosphorylated with Calf Intestine alkaline phosphatase (CIP) (BioLabs). After completion of the CIP reaction the cut vector was again column purified to generate the final vector. A three-part ligation was performed using Roche Rapid ligase and the vendor specifications. The final plasmid was verified by sequencing. Kinase domain.

Protein Sequence of BV 1075:

(SEQ ID NO: 4)

```
  1  MREYDRLYEE YTRTSQEIQM KRTAIEAFNE TIKIFEEQCQ TQERYSKEYI EKFKREGNEK
 61  EIQRIMHNYD KLKSRISEII DSRRRLEEDL KKQAAEYREI DKRMNSIKPG GGGGGGGGGG
121  GLVECLLPNG MIVTLECLRE ATLITIKHEL FKEARKYPLH QLLQDESSYI FVSVTQEAER
181  EEFFDETRRL CDLRLFQPFL KVIEPVGNRE EKILNREIGF AIGMPVCEFD MVKDPEVQDF
241  RRNILNVCKE AVDLRDLNSP HSRAMYVYPP NVESSPELPK HIYNKLDKGQ IIVVIWVIVS
301  PNNDKQKYTL KINHDCVPEQ VIAEAIRKKT RSMLLSSEQL KLCVLEYQGK YILKVCGCDE
361  YFLEKYPLSQ YKYIRSCIML GRMPNLMLMA KESLYSQLPM DCFTMPSYSR RISTATPYMN
421  GETSTKSLWV INSALRIKIL CATYVNVNIR DIDKIYVRTG IYHGGEPLCD NVNTQRVPCS
481  NPRWNEWLNY DIYIPDLPRA ARLCLSICSV KGRKGAKEEH CPLAWGNINL FDYTDTLVSG
541  KMALNLWPVP HGLEDLLNPI GVTGSNPNKE TPCLELEFDW FSSVVKFPDM SVIEEHANWS
601  VSREAGFSYS HAGLSNRLAR DNELRENDKE QLKAISTRDP LSEITEQEKD FLWSHRHYCV
661  TIPEILPKLL LSVKWNSRDE VAQMYCLVKD WPPIKPEQAM ELLDCNYPDP MVRGFAVRCL
721  EKYLTDDKLS QYLIQLVQVL KYEQYLDNLL VRFLLKKALT NQRIGHFFFW HLKSEMHNKT
781  VSQRFGLLLE SYCRACGMYL KHLNRQVEAM EKLINLTDIL KQEKKDETQK VQMKFLVEQM
841  RRPDFMDALQ GFLSPLNPAH QLGNLRLEEC RIMSSAKRPL WLNWENPDIM SELLFQNNEI
901  IFKNGDDLRQ DMLTLQIIRI MENIWQNQGL DLRMLPYGCL SIGDCVGLIE VVRNSHTIMQ
```

```
 961  IQCKGGLKGA  LQFNSHTLHQ  WLKDKNKGEI  YDAAIDLFTR  SCAGYCVATF  ILGIGDRHNS

1021  NIMVKDDGQL  FHIDFGHFLD  HKKKKFGYKR  ERVPFVLTQD  FLIVISKGAQ  ECTKTREFER

1081  FQEMCYKAYL  AIRQHANLFI  NLFSMMLGSG  MPELQSFDDI  AYIRKTLALD  KTEQEALEYF

1141  MKQMNDAHHG  GWTTKMDWIF  HTIKQHALNE  LGGAHHHHHH
```

PI3Kβ Constructs and Proteins

```
PI3Kβ   BV949   p85iSH2(461-N58K-568)-GGGGGG-p110β
                     (2-1070)-His
```

BV949: PCR products for the inter SH2 domain (iSH2) of the p85 PI3Kα, PI3Kβ and PI3Kδ subunit and for the full-length p110β subunit were generated and fused by overlapping PCR. The iSH2 PCR product was obtained from first strand cDNA generated by RT-PCR from commercial human RNA from placenta, testis and brain (Clontech), initially using primers gwG130-p01 (5'-CGAGAATATGATAGAT-TATATGAAGAAT-3') (SEQ ID NO: 5) and gwG130-p02 (5'-TGGTTT-AATGCTGTTCATACGTTTGTCAAT-3') (SEQ ID NO: 6). Subsequently, in a secondary PCR reaction Gateway recombination AttB1 sites and linker sequences were added at the 5' end and 3' end of the p85 iSH2 fragment respectively, using primers gwG130-p03 (5'-GGGA-CAAGTT-TGTACAAAAAAGCAGGCTACGAAG-GAGATATACATATGCGAGAATATGATAGATTATAT GAAGAAT-3') (SEQ ID NO: 7) and gwG130-p05 (5'-ACT-GAAGCATCCTCCTC-CTCCTCCT-CCTGGTTTAAT-GCTGTTCATACGTTTGTC-3') (SEQ ID NO: 8). The p110β fragment was obtained by PCR using as template a p110β clone (from unknown source that was sequence veri- fied) using primers gwG130-p04 (5'-ATTAAACCAGGAG-GAGGAGGAGGAGGATGCTT-CAGTTTCATAATGC-CTCCTGCT-3') (SEQ ID NO: 9) which contains linker sequences and the 5' end of p110β and gwG130-p06 (5'-AGCTCCGTGATGGTGATGGTGATGTGCTCCAGATC-TGTAGTCTTTCCGAA-CTGTGTG-3') (SEQ ID NO: 10) which contains sequences of the 3' end of p110-β fused to a Histidine tag. The p85-iSH2/p110β fusion protein was assembled by an overlapping PCR a reaction of the linkers at the 3' end of the iSH2 fragment and the 5' end of the p110β fragment, using the above mentioned gwG130-p03 primer and a primer containing an overlapping Histidine tag and the AttB2 recombination sequences (5'-GGGACCACTTTGTA-CAAGAAAGCTGGGTTTAAGCTCCGT-GATGGTGATGGTGATGTGC TCC-3') (SEQ ID NO: 11). This final product was recombined in a Gateway (Invitrogen) OR reaction into the donor vector pDONR201 (Invitrogen) to generate the ORF253 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR280. This LR280 has an amino acid mutation in the p85 sequence.

Kinase Domain.

Protein Sequence of BV949:

```
                                                        (SEQ ID NO: 12)
   1  MREYDRLYEE  YTRTSQEIQM  KRTAIEAFNE  TIKIFEEQCQ  TQERYSKEYI  EKFKREGKEK

61  EIQRIMHNYD  KLKSRISEII  DSRRRLEEDL  KKQAAEYREI  DKRMNSIKPG  GGGGGCFSFI

121  MPPAMADILD  IWAVDSQIAS  DGSIPVDFLL  PTGIYIQLEV  PREATISYIK  QMLWKQVHNY

181  PMFNLLMDID  SYMFACVNQT  AVYEELEDET  RRLCDVRPFL  PVLKLVTRSC  DPGEKLDSKI

241  GVLIGKGLHE  FDSLKDPEVN  EFRRKMRKFS  EEKILSLVGL  SWMDWLKQTY  PPEHEPSIPE

301  NLEDKLYGGK  LIVAVHFENC  QDVFSFQVSP  NMNPIKVNEL  AIQKRLTIHG  KEDEVSPYDY

361  VLQVSGRVEY  VFGDHPLIQF  QYIRNCVMNR  ALPHFILVEC  CKIKKMYEQE  MIAIEAAINR

421  NSSNLPLPLP  PKKTRIISHV  WENNNPFQIV  LVKGNKLNTE  ETVKVHVRAG  LFHGTELLCK

481  TIVSSEVSGK  NDHIWNEPLE  FDINICDLPR  MARLCFAVYA  VLDKVKTKKS  TKTINPSKYQ

541  TIRKAGKVHY  PVAWVNTMVF  DFKGQLRTGD  IILHSWSSFP  DELEEMLNPM  GTVQTNPYTE

601  NATALHVKFP  ENKKQPYYYP  PFDKIIEKAA  EIASSDSANV  SSRGGKKFLP  VLKEILDRDP

661  LSQLCENEMD  LIWTLRQDCR  EIFPQSLPKL  LLSIKWNKLE  DVAQLQALLQ  IWPKLPPREA

721  LELLDFNYPD  QYVREYAVGC  LRQMSDEELS  QYLLQLVQVL  KYEPFLDCAL  SRFLLERALG

781  NRRIGQFLFW  HLRSEVHIPA  VSVQFGVILE  AYCRGSVGHM  KVLSKQVEAL  NKLKTLNSLI

841  KLNAVKLNRA  KGKEAMHTCL  KQSAYREALS  DLQSPLNPCV  ILSELYVEKC  KYMDSKMKPL

901  WLVYNNKVFG  EDSVGVIFKN  GDDLRQDMLT  LQMLRLMDLL  WKEAGLDLRM  LPYGCLATGD

961  RSGLIEVVST  SETIADIQLN  SSNVAAAAAF  NKDALLNWLK  EYNSGDDLDR  AIEEFTLSCA
```

```
1021  GYCVASYVLG  IGDRHSDNIM  VKKTGQLFHI  DFGHILGNFK  SKFGIKRERV  PFILTYDFIH

1081  VIQQGKTGNT  EKFGRFRQCC  EDAYLILRRH  GNLFITLFAL  MLTAGLPELT  SVKDIQYLKD

1141  SLALGKSEEE  ALKQFKQKFD  EALRESWTTK  VNWMAHTVRK  DYRSGAHHHH  HHGA
```

Kinase Domain.
PI3Kγ Construct and Protein

```
PI3Kγ    BV950    p110γ(Δ143-[Met144-1102])-His
```

Construct obtained from Roger Williams lab, MRC Laboratory of Molecular Biology, Cambridge, UK (November, 2003). Description of the construct in (Pacold, Michael E.; Suire, Sabine; Perisic, Olga; Lara-Gonzalez, Samuel; Davis, Colin T.; Walker, Edward H.; Hawkins, Phillip T.; Stephens, Len; Eccleston, John F.; Williams, Roger L. Crystal structure and functional analysis of Ras binding to its effector phosphoinositide 3-kinase gamma. Cell (2000), 103(6), 931-943). Constructs lacking the N-terminal 144 aa.
Protein Sequence of BV950:

```
                                                    (SEQ ID NO: 13)
  1  MSEESQAFQR  QLTALIGYDV  TDVSNVHDDE  LEFTRRGLVT  PRMAEVASRD  PKLYAMHPWV

61  TSKPLPEYLW  KKIANNCIFI  VIHRSTTSQT  IKVSPDDTPG  AILQSFFTKM  AKKKSLMDIP

121  ESQSEQDFVL  RVCGRDEYLV  GETPIKNFQW  VRHCLKNGEE  IHVVLDTPPD  PALDEVRKEE

181  WPLVDDCTGV  TGYHEQLTIH  GKDHESVFTV  SLWDCDRKFR  VKIRGIDIPV  LPRNTDLTVF

241  VEANIQHGQQ  VLCQRRTSPK  PFTEEVLWNV  WLEFSIKIKD  LPKGALLNLQ  IYCGKAPALS

301  SKASAESPSS  ESKGKVRLLY  YVNLLLIDHR  FLLRRGEYVL  HMWQISGKGE  DQGSFNADKL

361  TSATNPDKEN  SMSISILLDN  YCHPIALPKH  QPTPDPEGDR  VRAEMPNQLR  KQLEAIIATD

421  PLNPLTAEDK  ELLWHFRYES  LKHPKAYPKL  FSSVKWGQQE  IVAKTYQLLA  RREVWDQSAL

481  DVGLTMQLLD  CNFSDENVRA  IAVQKLESLE  DDDVLHYLLQ  LVQAVKFEPY  HDSALARFLL

541  KRGLRNKRIG  HFLFWFLRSE  IAQSRHYQQR  FAVILEAYLR  GCGTAMLHDF  TQQVQVIEML

601  QKVTLDIKSL  SAEKYDVSSQ  VISQLKQKLE  NLQNSQLPES  FRVPYDPGLK  AGALAIEKCK

661  VMASKKKPLW  LEFKCADPTA  LSNETIGIIF  KHGDDLRQDM  LILQILRIME  SIWETESLDL

721  CLLPYGCIST  GDKIGMIEIV  KDATTIAKIQ  QSTVGNTGAF  KDEVLNHWLK  EKSPTEEKFQ

781  AAVERFVYSC  AGYCVATFVL  GIGDRHNDNI  MITETGNLFH  IDFGHILGNY  KSFLGINKER

841  VPFVLTPDFL  FVMGTSGKKT  SPHFQKFQDI  CVKAYLALRH  HTNLLIILFS  MMLMTGMPQL

901  TSKEDIEYIR  DALTVGKNEE  DAKKYFLDQI  EVCRDKGWTV  QFNWFLHLVL  GIKQGEKHSA

961  HHHHHH
```

PI3Kδ Construct and Protein

```
PI3Kδ    BV1060    p85iSH2(461-568)-GGGGGG-p110δ
                    (2-1044)-His
```

BV1060: PCR products for the inter SH2 domain (iSH2) of the p85 subunit and for the full-length p110δ subunit were generated and fused by overlapping PCR. The iSH2 PCR product was generated by using as a template the ORF318 (see above) and the primers gwG130-p03 (5'-GGGACAAG-TTTGTACAAAAAAGCAGGCTACGAAG-GAGATATACATATGC-GAGAATATGATAGATTATAT-GAAGAAT-3') (SEQ ID NO: 7) and gwG154-p04 (5'-TCCTCCTCCT-CCTCCTCCTGGTTTAATGCTGTTCATACGTTTGTC-3) (SEQ ID NO: 14). The p110δ fragment was obtained from first strand cDNA generated by RT-PCR from commercial human RNA from placenta, testis and brain (Clontech), using initially primers gwG154-p01 (5'-ATGCCCCCTGGGGTG-GACTGCCCCAT-3') (SEQ ID NO: 15) and gwG154-p02 (5'-CTACTGCCTGT-TGTCTTTGGACACGT-3') (SEQ ID NO: 16). In a subsequent PCR reaction linker sequences and a Histidine tag was added at the 5' end and 3' end of the p110δ fragment respectively, using primers gw154-p03 (5'-AT-TAAACCAGGAGGAGGAGGAGGAGGAC-CCCCTGGGGTGGAC-TGCCCCATGGA-3') (SEQ ID NO: 17) and gwG154-p06 (5'-AGCTCCGTGATGGT-GATGGTGAT-GTGCT-CCCTGCCTGTTGTCTTTGGA-CACGTTGT-3') (SEQ ID NO: 18). The p85-iSH2/p110δ fusion protein was assembled in a third PCR reaction by the overlapping linkers at the 3' end of the iSH2 fragment and the 5' end of the p110δ fragment, using the above mentioned gwG130-p03 primer and a primer containing an overlapping Histidine tag and the Gateway (Invitrogen) AttB2 recombination sequences (5'-GGG-ACCACTTTGTACAA-GAAAGCTGGGTTAA-GCTCCGTGATGGTGATGGT-GAGTGCTCC-3') (SEQ ID NO: 19). This final product was recombined in a Gateway OR reaction into the donor vector pDONR201 (Invitrogen) to generate the ORF319 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR415.

Protein Sequence of BV1060:

(SEQ ID NO: 20)

```
   1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GGGGGPPGVD

121 CPMEFWTKEE NQSVVVDFLL PTGVYLNFPV SRNANLSTIK QLLWHRAQYE PLFHMLSGPE

181 AYVFTCINQT AEQQELEDEQ RRLCDVQPFL PVLRLVAREG DRVKKLINSQ ISLLIGKGLH

241 EFDSLCDPEV NDFRAKMCQF CEEAAARRQQ LGWEAWLQYS FPLQLEPSAQ TWGPGTLRLP

301 NRALLVNVKF EGSEESFTFQ VSTKDVPLAL MACALRKKAT VFRQPLVEQP EDYTLQVNGR

361 HEYLYGSYPL CQFQYICSCL HSGLTPHLTM VHSSSILAMR DEQSNPAPQV QKPRAKPPPI

421 PAKKPSSVSL WSLEQPFRIE LIQGSKVNAD ERMKLVVQAG LFHGNEMLCK TVSSSEVSVC

481 SEPVWKQRLE FDINICDLPR MARLCFALYA VIEKAKKARS TKKKSKKADC PIAWANLMLF

541 DYKDQLKTGE RCLYMWPSVP DEKGELLNPT GTVRSNPNTD SAAALLICLP EVAPHPVYYP

601 ALEKILELGR HSECVHVTEE EQLQLREILE RRGSGELYEH EKDLVWKLRH EVQEHFPEAL

661 ARLLLVTKWN KHEDVAQMLY LLCSWPELPV LSALELLDFS FPDCHVGSFA IKSLRKLTDD

721 ELFQYLLQLV QVLKYESYLD CELTKFLLDR ALANRKIGHF LFWHLRSEMH VPSVALRFGL

781 ILEAYCRGST HHMKVLMKQG EALSKLKALN DFVKLSSQKT PKPQTKELMH LCMRQEAYLE

841 ALSHLQSPLD PSTLLAEVCV EQCTFMDSKM KPLWIMYSNE EAGSGGSVGI IFKNGDDLRQ

901 DMLTLQMIQL MDVLWKQEGL DLRMTPYGCL PTGDRTGLIE VVLRSDTIAN IQLNKSNMAA

961 TAAFNKDALL NWLKSKNPGE ALDRAIEEFT LSCAGYCVAT YVLGIGDRHS DNIMIRESGQ

1021 LFHIDFGHFL GNFKTKFGIN RERVPFILTY DFVHVIQQGK TNNSEKFERF RGYCERAYTI

1081 LRRHGLLFLH LFALMRAAGL PELSCSKDIQ YLKDSLALGK TEEEALKHFR VKFNEALRES

1141 WKTKVNWLAH NVSKDNRQEL GGAHHHHHH
```

Purification of PI3Kα, PI3Kβ and PI3Kγ Constructs

PI3Kα, PI3Kβ and PI3Kγ were purified in two chromatographic steps: immobilized metal affinity chromatography (IMAC) on a Ni sepharose resin (GE Healthcare) and gel filtration utilizing a Superdex 200 26/60 column (GE Healthcare). All buffers were chilled to 4° C. and lysis was performed chilled on ice. Column fractionation was performed at room temperature. All buffers used to purify PI3Kβ contained 0.05% Triton X100 in addition to what is described below.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 ug/mL okadaic acid (OAA), 5 mM BME, 1× Complete protease inhibitor cocktail—EDTA-free (20 tablets/1 L buffer, Roche Applied Sciences), benzonase (25 U/mL buffer, EMD Biosciences) at a ratio of 1:6 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (3 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 45 mM imidazole, 1 mM NaF, 0.1 μg/mL OAA, 5 mM BME, 1× Complete protease inhibitor cocktail—EDTA-free. Protein was eluted with 20 mM Tris-Cl, pH 7.5, 0.5 M NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 26/60 column equilibrated in 20 mM Tris-Cl, pH 7.5, 0.5 M NaCl, 5% glycerol, 1 mM NaF, 5 mM DTT, 1× Complete protease inhibitor cocktail—EDTA-free. Pertinent fractions were analyzed by SDS-PAGE and pooled accordingly. An equal volume of Dialysis Buffer (20 mM Tris-Cl, pH 7.5, 500 mM NaCl, 50% glycerol, 5 mM NaF, 5 mM DTT) was added to the pool and than dialyzed against Dialysis Buffer two changes (one change overnight). Protein was stored at −20° C.

Purification of PI3Kδ

PI3Kδ was purified in three chromatographic steps: immobilized metal affinity chromatography on a Ni Sepharose resin (GE Healthcare), gel filtration utilizing a Superdex 200 26/60 column (GE Healthcare), and finally a ion exchange step on a Q-HP column (GE Healthcare). All buffers were chilled to 4° C. and lysis was performed chilled on ice. Column fractionation was performed at room temperature.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 μg/mL okadaic acid (OAA), 5 mM BME, 1× Complete protease inhibitor cocktail—EDTA-free (20 tablets/1 L buffer, Roche Applied Sciences), benzonase (25 U/mL lysis buffer, EMD Biosciences) at a ratio of 1:10 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (5 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 40 mM imidazole, 1 mM NaF, 0.1 ug/mL OAA, 5 mM BME, 1× Complete protease inhibitor cocktail—EDTA-free. Protein was eluted with 20 mM Tris-Cl, pH 7.5, 500 mM NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 equilibrated in 20 mM Tris-Cl, pH 7.5, 500 mM NaCl, 5% glycerol, 1 mM NaF, 0.1 ug/mL OAA, 5 mM DTT, 1× Complete protease inhibitor cocktail—EDTA-free. Pertinent fractions were analyzed by SDS-PAGE and pooled accordingly. These fractions were diluted 1:10 v/v pool volume to buffer ratio with "Buffer A" 20 mM Tris-Cl, pH 8.2, 5% glycerol, 1 mM NaF, 0.1 μg/mL OAA, 5 mM DTT and loaded onto a prepared Q-HP column. After sample loading is completed we wash with Buffer A and 5% "Buffer B" 20 mM Tris-Cl, pH 8.2, 1 M NaCl, 5% glycerol, 1 mM NaF, 0.1 ug/mL OAA, 5 mM DTT for 3-5 column volumes. We elute the protein using a 5%-30% gradient of Buffer B. Typically the protein elutes at ~200 mM NaCl. Pertinent fractions were analyzed by SDS-PAGE and pooled accordingly. An equal volume of Dialysis Buffer (20 mM Tris-Cl, pH 7.5, 500 mM NaCl, 50% glycerol, 1 mM NaF, 0.1 μg/mL OAA, 5 mM DTT) was added to the pool and then dialyzed against Dialysis Buffer two changes (one change overnight). Protein was stored at −20° C.

The following results were obtained using the above described assays.

| ex. | PI3Ka/IC50 [umol l−1] | PI3Kb/IC50 [umol l−1] | PI3Kd/IC50 [umol l−1] | PI3Kg/IC50 [umol l−1] |
|---|---|---|---|---|
| 1 | 0.014 | 4.428 | 0.971 | 0.680 |
| 27 | 0.081 | 5.200 | 0.271 | 1.563 |
| 12 | 0.010 | 3.874 | 0.197 | 0.352 |
| 35 | 0.006 | 0.860 | 0.029 | 0.360 |
| 15 | 0.008 | 1.212 | 0.077 | 1.097 |
| 13 | 0.013 | 4.491 | 0.161 | 0.183 |
| 3 | 0.067 | 2.301 | 0.432 | 0.362 |
| 5 | 0.044 | 3.905 | 0.648 | 2.047 |
| 37 | 0.039 | 5.521 | 0.386 | 4.447 |
| 29 | 0.056 | 6.175 | 0.804 | 0.684 |
| 18 | 0.019 | 4.137 | 0.538 | 0.612 |
| 51 | 0.113 | 8.838 | 0.690 | 3.480 |
| 47 | 0.094 | 2.903 | 0.156 | 1.875 |
| 59 | 0.064 | 3.497 | 0.881 | 0.917 |
| 64 | 0.010 | 0.692 | 0.032 | 0.451 |
| 61 | 0.072 | 6.113 | 0.901 | 1.517 |
| 66 | 0.013 | 2.740 | 0.298 | 0.435 |
| 42 | 0.012 | 3.165 | 0.289 | 0.858 |
| 63 | 0.016 | 1.2 | 0.098 | 0.79 |

Compounds of the present invention, in particular, the preferred compounds of the present invention, show an improved selectivity for PI3K alpha with respect to beta and/or delta and/or gamma subtypes e.g. as measured in a biochemical assay. Those compounds also preferably show selectivity for PI3K alpha with respect to beta and/or delta and/or gamma subtypes as measured in the cellular assay.

EXAMPLE B

Determination of In Vitro Metabolic Clearance

Abbreviations
ACN Acetonitrile
ADME Absorption, Distribution, Metabolism and Excretion
ALP Automated labware positioner
% B % of HPLC solvent B
BT Biotransformation (or metabolic stability or microsomal stability)
[C]t=0 Initial (time zero) in vitro concentration of TA
CLh Hepatic clearance (ml/min/kg)
CLint Intrinsic clearance rate (μL reaction volume/min/mg microsomal protein)
CLint,s Intrinsic clearance rate scaled for liver mass (mL reaction volume/min/g liver)
Cyno Cynomolgous
CYP(s) Cytochrome P450(s)
DiH2O Deionized water
ERh Hepatic extraction ratio
ESI Electrospray ionization
fub Free fraction of drug in blood or plasma
fum Free fraction of drug in microsomes
IS Internal standard
kmic Elimination rate in microsomes
KPi 0.05M Potassium phosphate buffer, pH 7.4
LC-MS/MS Liquid chromatography coupled tandem mass spectrometry
LOD Limit of detection
M Microsomal protein content in the incubation (mg/mL)
NADPH β-Nicotinamide adenine dinucleotide phosphate, reduced form
NCE New chemical entity
NSB Non-specific binding
Qh Portal blood flow (mL/min/kg)
RPM Rotations per minute
SD Standard deviation
S-D Sprague-Dawley
SF1 Scaling factor: mg microsomal protein per gram liver
SF2 Scaling factor: gram of liver per kg animal body weight
t½ In vitro clearance half-life (min)
TA Test article
UDPGA Uridine 5′ diphosphoglucuronic acid
UGT Uridine 5′ diphosphate glucuronosyltransferases
V Reaction incubation volume (μL)

Final test article and protein concentrations, as well as incubation duration, are shown below (Table 1). Low test article concentrations were selected to comply with the assumption that reaction kinetics are evaluated at a concentration less than (or approximately equal to) Km. DMSO is known to have an inhibitory effect on CYP activity. Therefore, the concentration of DMSO in the incubation media has been restricted to 0.01% (v/v) so that interference to the metabolic process is minimized.

TABLE 1

Final reaction components and concentrations in metabolic clearance incubations

| Reaction component | Final reaction concentration |
|---|---|
| Potassium phosphate (KPi) buffer, pH 7.4 | 50 mM |
| MgCl2 | 2.0 mM |
| NADPH | 1.0 mM |
| UDPGA[a] | 1.0 mM |
| Alamethacin[a] | 25 μg/mg liver microsomes |
| Liver microsomes | 0.5 mg/mL |
| Test article | 1.0 μM |
| CAN | 0.06% (v/v) |
| DMSO (test article solvent) | 0.01% (v/v) |

[a]Optional components required only to reconstitute UGT (Uridine 5′diphosphate glucuronosyltransferases) activity.

A typical experiment is performed in 96-well format with shaking incubation at 37° C. The in vitro metabolic clearance rate is derived from data collected at four time points (eg. 0, 5, 15 and 30 minutes) in a reaction including cofactor(s) (NADPH and/or UDPGA). A 30 minutes negative control incubation (minus cofactor) is also performed to assess CYP-unrelated stability issues (eg, chemical instability, CYP-independent metabolism).

In general, TA's in 10 mM DMSO are diluted 1:1000 into 0.6% ACN (v/v) in DiH2O to 10 µM. Immediately prior to the start of the experiment, 1.25 mg/mL of microsomal protein is suspended in 50 mM KPi. For evaluation of UGT-mediated metabolism, the suspension may be first pretreated by 5 min incubation on ice with alamethicin (25 µg/mg of microsomal protein). TA (35 µL) is added to 140 µL of the microsomal suspensions for 175 µL enzyme-substrate mixture. This enzyme-substrate mixture is preincubated for 15 min at 37° C. The 30 min negative control incubation is processed by combining 25 µL of enzyme-substrate mixture with an equal volume of 50 mM KPi containing 4 mM $MgCl_2$. Following a 30 minute incubation at 37° C., the mix is quenched by adding 50 µL of ACN containing the MS internal standard (2 µM alprenolol). The T=0 min time point is processed by combining 25 µL of enzyme-substrate mixture directly with 50 µL of ACN containing the MS internal standard (2 µM alprenolol). 25 µL of the cofactor solution is added (2 mM NADPH in 50 mM KPi plus 4 mM $MgCl_2$; optionally including 2 mM UDPGA for CYP+UGT assays) to simulate the complete quenched reaction mixture.

The bulk reactions for the remaining time points are initiated by addition of 125 µL of cofactor solution (2 mM NADPH in 50 mM KPi plus 4 mM $MgCl_2$) to the remaining 125 µL of enzyme-substrate mixture. For UGT metabolism, 2 mM UDPGA, is included in the cofactor solution, as well. At specific reaction time points (eg. 5, 15, 30 minutes), reaction aliquots (50 µL) are removed and reactions are terminated by addition of acetonitrile (50 µL) containing mass spectrometry internal standard (2 µM alprenolol). All the samples are centrifuged at ~3400×g at 4° C. for 10 min and the supernatants are analyzed by LC-MS/MS for quantitation of remaining TA. The percentage of TA remaining, relative to 0 minutes, is used to estimate in vitro elimination-rate constant (kmic) which can be used to calculate in vitro metabolic clearance rates.

Analysis of samples is performed on a high performance liquid chromatography-tandem mass spectrometry (LC/MS) system consisting of a Waters Quattro Premiere mass spectrometer, an ESI ion source, a CTC-HTS PaI autosampler, and an Agilent LC Pump. Samples are separated on an Atlantic C18 column, 2.1×30 mm, 3.5 micron using the fast mobile phase gradient outlined in Table 2. Mobile phase A consists of purified water containing 10 mM ammonium formate. Mobile phase B consists of acetonitrile containing 0.01% formic acid. The flow rate is 1 mL/min. The injection volume is 10 µL. The first 30 seconds of elute is diverted to waste for sample clean-up. Compounds are detected using the software MassLynx/QuanLynx which collects intensity data for all fragments related to the molecular weight of the test compound. After collection of the raw data, the software may combine the profiles of up to 3 quality fragments if needed. Generally, the fragment peak of strongest intensity is integrated.

TABLE 2

| Mobile phase gradient for HPLC | |
|---|---|
| Time (min) | % B |
| 0.0 | 5 |
| 0.2 | 5 |

TABLE 2-continued

| Mobile phase gradient for HPLC | |
|---|---|
| Time (min) | % B |
| 0.85 | 95 |
| 1.02 | 95 |
| 1.05 | 5 |

Each microsomal elimination rate, kmic, is based on a 4-point elimination curve tested in singlet. LC-MS/MS raw data for a reaction plate is returned as integrated analyte peak areas for the TA and IS. These values may be converted to analyte:IS peak area ratios to standardize data comparisons.

The reaction time point (eg. 0, 5, 20 or 30 min) is plotted versus the natural logarithm of percent TA remaining relative to 0 minutes (based on relative peak area ratio). The slope of this clearance plot, kmic, is used to calculate the in vitro half-life, t½, as shown in Eq. (1). In order to focus on linear reaction kinetics, whenever possible, data points representing <10% TA remaining are generally excluded from the definition of the clearance plot slope. The reaction t½ is the core experimental value used for calculating CLint (Eq. 2)

$$t\frac{1}{2} = 0.693/-k_{mic} \qquad \text{Eq. (1)}$$

$$\text{Clint} = 0.693/-k_{mic} \cdot V/M \qquad \text{Eq (2)}$$

The following results were obtained using the above described procedure:

| example | CYP MetCL-Ra/CL(int) [ul min−1 mg−1] | CYP MetCL-Hu/CL(int) [ul min−1 mg−1] |
|---|---|---|
| comparative example, | | |
| WO2004/096797, no 133 | 56 | 37 |
| examples according to this invention | | |
| 15 | 29 | 33 |
| 61 | 22 | 19 |
| 55 | 29 | 27 |

EXAMPLE C

Inhibition of PI3K Alpha Mutants E545K and H1047R Determined in a Luciferase Luminescence Assay Luminescence is a well established readout to determine ATP concentrations and can thus be used to follow the activity of many kinases regardless of their substrate. The KinaseGlo Luminescent Kinase Assay (Promega, Madison, Wis., USA) is a homogeneous HTS method of measuring kinase activity by quantifying the amount of ATP remaining in solution following a kinase reaction.

Phosphoinositide 3-kinase was incubated at room temperature in 50-µl medium containing 1 µM ATP, 5 mM $MgCl_2$, 50 mM NaCl, 5 µg/ml soybeen phosphatidylinositol (Avanti Polar lipids, Cat. Nr 840044C), 0.015% octoglucoside (Sigma, Cat. Nr 09882), 0.01% CHAPS, 1 mM DTT, 2.5% DMSO, and 10 mM Tris-HCl pH 7.5. The kinase reaction was initiated by the addition of ATP (15 min preincubation of enzyme with inhibitor) and stopped after 1 h with 50 µl KinaseGlo® (Promega, cat. Nr V6714) and luminescence was measured by a Victor II reader (0.1 s integration). Curves were fitted by non-linear regression using the logistic equation (model 205 of XLfit®, ID Business Solutions, Guildford, UK).

Assay Principle of Luminescence Assay (KinaseGlo):

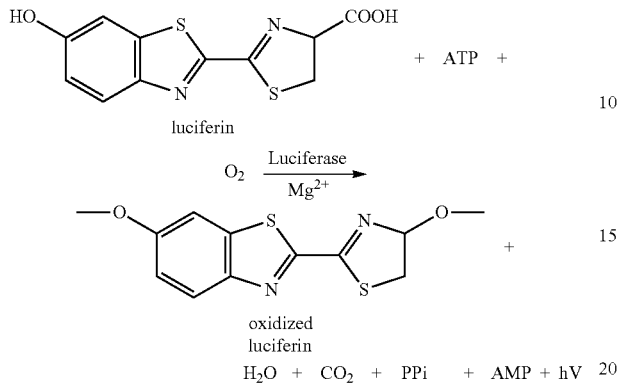

Using above assay system and using PI3K proteins obtained from constructs shown in the following table the inhibitory activity against wild type and mutant PI3Kalpha was assessed. The results are shown in the following table.

Inhibition of Wild Type and Mutant PI3Kalpha:

| Example | PI3Kalpha wild type | PI3Kalpha E545K | PI3Kalpha H1047R |
|---|---|---|---|
| | | IC50s in nM | |
| 5 | 8.2 | 6.7 | 7.7 |
| 15 | 4.6 | 4.0 | 4.8 |
| 61 | 3.9 | 2.7 | 3.6 |

BV1147: The activating mutation E545K found in many cancers was introduced into ORF318 by site directed mutagenesis with the QuickChange XL mutagenesis kit (Stratagene). Uusing the method recommended by the manufacturer and the mutagenic primers gwG152-p15 (5'-CTCTCTGAAATCACTAAGCAGGAGAAAGATTTT-3') (SEQ ID NO: 21) and gwG152-p16 (5'-AAAATCTTTCT-CCTGCTTAGTGATTTCAGAGAG-3') (SEQ ID NO: 22) ORF544 was generated. This clone was verified by sequencing and used in a Gateway LR reaction (Invitrogen) to transfer the insert into the Gateway adapted pBlueBac4.5 (Invitrogen) vector for generation of the baculovirus expression vector LR561.

| Type | Code | Construct |
|---|---|---|
| Wild type | BV1075 | p85iSH2(461-568)-GGGGGGGGGGGG-p110α(21-1068)-His |
| E545K | BV1147 | p85iSH2(461-568)-GGISGGGGGIMV-p110α(21-E542K-1068)-His |
| H1047R | BV1097 | p85iSH2(461-568)-GGISGGGGGIMV-p110α(21-H1047R-1068)-His |

Kinase Domain.

Protein Sequence of BV 1147:

(SEQ ID NO: 23)

```
  1  MREYDRLYEE YTRTSQEIQM KRTAIEAFNE TIKIFEEQCQ TQERYSKEYI EKFKREGNEK
 61  EIQRIMHNYD KLKSRISEII DSRRRLEEDL KKQAAEYREI DKRMNSIKPG GISGGGGIM
121  VLVECLLPNG MIVTLECLRE ATLITIKHEL FKEARKYPLH QLLQDESSYI FVSVTQEAER
181  EEFFDETRRL CDLRLFQPFL KVIEPVGNRE EKILNREIGF AIGMPVCEFD MVKDPEVQDF
241  RRNILNVCKE AVDLRDLNSP HSRAMYVYPP NVESSPELPK HIYNKLDKGQ IIVVIWVIVS
301  PNNDKQKYTL KINHDCVPEQ VIAEAIRKKT RSMLLSSEQL KLCVLEYQGK YILKVCGCDE
361  YFLEKYPLSQ YKYIRSCIML GRMPNLMLMA KESLYSQLPM DCFTMPSYSR RISTATPYMN
421  GETSTKSLWV INSALRIKIL CATYVNVNIR DIDKIYVRTG IYHGGEPLCD NVNTQRVPCS
481  NPRWNEWLNY DIYIPDLPRA ARLCLSICSV KGRKGAKEEH CPLAWGNINL FDYTDTLVSG
541  KMALNLWPVP HGLEDLLNPI GVTGSNPNKE TPCLELEFDW FSSVVKFPDM SVIEEHANWS
601  VSREAGFSYS HAGLSNRLAR DNELRENDKE QLKAISTRDP LSEITKQEKD FLWSHRHYCV
661  TIPEILPKLL LSVKWNSRDE VAQMYCLVKD WPPIKPEQAM ELLDCNYPDP MVRGFAVRCL
721  EKYLTDDKLS QYLIQLVQVL KYEQYLDNLL VRFLLKKALT NQRIGHFFFW HLKSEMHNKT
781  VSQRFGLLLE SYCRACGMYL KHLNRQVEAM EKLINLTDIL KQEKKDETQK VQMKFLVEQM
```

```
 841 RRPDFMDALQ GFLSPLNPAH QLGNLRLEEC RIMSSAKRPL WLNWENPDIM SELLFQNNEI

901 IFKNGDDLRQ DMLTLQIIRI MENIWQNQGL DLRMLPYGCL SIGDCVGLIE VVRNSHTIMQ

961 IQCKGGLKGA LQFNSHTLHQ WLKDKNKGEI YDAAIDLFTR SCAGYCVATF ILGIGDRHNS

1021 NIMVKDDGQL FHIDFGHFLD HKKKKFGYKR ERVPFVLTQD FLIVISKGAQ ECTKTREFER

1081 FQEMCYKAYL AIRQHANLFI NLFSMMLGSG MPELQSFDDI AYIRKTLALD KTEQEALEYF

1141 MKQMNDAHHG GWTTKMDWIF HTIKQHALNE LGGAHHHHHH.
```

BV1097: The activating mutation H1047R found in many cancers was introduced into ORF318 by site directed mutagenesis with the QuickChange XL mutagenesis kit (Stratagene).

Using the method recommended by the manufacturer and the mutagenic primers gwG152-p07 (5'-CAAATGAATGAT-GCACGTCATGGTGGCTGGACA-3') (SEQ ID NO: 24) and gwG152-p11 (5'-TGTCCAGCCA-CCATGACGTG-CATCATTCATTTG-3') (SEQ ID NO: 25) ORF396 was generated. This clone was verified by sequencing and used in a Gateway LR reaction (Invitrogen) to transfer the insert into the Gateway adapted pBlueBac4.5 vector (Invitrogen) for generation of the baculovirus expression vector LR480.

Kinase Domain.
Protein Sequence of BV 1097:

```
                                                          (SEQ ID NO: 26)
   1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GISGGGGIM

121 VLVECLLPNG MIVTLECLRE ATLITIKHEL FKEARKYPLH QLLQDESSYI FVSVTQEAER

181 EEFFDETRRL CDLRLFQPFL KVIEPVGNRE EKILNREIGF AIGMPVCEFD MVKDPEVQDF

241 RRNILNVCKE AVDLRDLNSP HSRAMYVYPP NVESSPELPK HIYNKLDKGQ IIVVIWVIVS

301 PNNDKQKYTL KINHDCVPEQ VIAEAIRKKT RSMLLSSEQL KLCVLEYQGK YILKVCGCDE

361 YFLEKYPLSQ YKYIRSCIML GRMPNLMLMA KESLYSQLPM DCFTMPSYSR RISTATPYMN

421 GETSTKSLWV INSALRIKIL CATYVNVNIR DIDKIYVRTG IYHGGEPLCD NVNTQRVPCS

481 NPRWNEWLNY DIYIPDLPRA ARLCLSICSV KGRKGAKEEH CPLAWGNINL FDYTDTLVSG

541 KMALNLWPVP HGLEDLLNPI GVTGSNPNKE TPCLELEFDW FSSVVKFPDM SVIEEHANWS

601 VSREAGFSYS HAGLSNRLAR DNELRENDKE QLKAISTRDP LSEITEQEKD FLWSHRHYCV

661 TIPEILPKLL LSVKWNSRDE VAQMYCLVKD WPPIKPEQAM ELLDCNYPDP MVRGFAVRCL

721 EKYLTDDKLS QYLIQLVQVL KYEQYLDNLL VRFLLKKALT NQRIGHFFFW HLKSEMHNKT

781 VSQRFGLLLE SYCRACGMYL KHLNRQVEAM EKLINLTDIL KQEKKDETQK VQMKFLVEQM

841 RRPDFMDALQ GFLSPLNPAH QLGNLRLEEC RIMSSAKRPL WLNWENPDIM SELLFQNNEI

901 IFKNGDDLRQ DMLTLQIIRI MENIWQNQGL DLRMLPYGCL SIGDCVGLIE VVRNSHTIMQ

961 IQCKGGLKGA LQFNSHTLHQ WLKDKNKGEI YDAAIDLFTR SCAGYCVATF ILGIGDRHNS

1021 NIMVKDDGQL FHIDFGHFLD HKKKKFGYKR ERVPFVLTQD FLIVISKGAQ ECTKTREFER

1081 FQEMCYKAYL AIRQHANLFI NLFSMMLGSG MPELQSFDDI AYIRKTLALD KTEQEALEYF

1141 MKQMNDARHG GWTTKMDWIF HTIKQHALNE LGGAHHHHHH.
```

What is claimed is:

1. A compound of formula (IA)

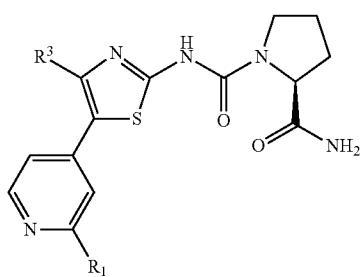

(IA)

or a salt thereof, wherein

R[1] represents one of the following substituents: (1) substituted, $C_1$-$C_7$-alkyl, wherein said substituents are independently selected from one to nine of the following moieties: deuterium and fluoro, or one to two of the following moieties: $C_3$-$C_5$-cycloalkyl; (2) optionally substituted $C_3$-$C_5$-cycloalkyl wherein said substituents are independently selected from one to four of the following moieties: deuterium, methyl, fluoro, cyano and aminocarbonyl; (3) optionally substituted phenyl wherein said substituents are independently selected from one to two of the following moieties: deuterium, halo, cyano, $C_1$-$C_7$-alkyl, $C_1$-$C_7$-alkylamino, di($C_1$-$C_7$-alkyl)amino, $C_1$-$C_7$-alkylaminocarbonyl, di($C_1$-$C_7$-alkyl)aminocarbonyl and $C_1$-$C_7$-alkoxy; (4) optionally mono- or di-substituted amine; wherein said substituents are independently selected from the following moieties: deuterium; $C_1$-$C_7$-alkyl which is unsubstituted or substituted by one or more substituents selected from deuterium, fluoro, chloro and hydroxy; phenylsulfonyl which is unsubstituted or substituted by one or more groups selected from $C_1$-$C_7$-alkyl, $C_1$-$C_7$-alkoxy and di($C_1$-$C_7$-alkyl)amino-$C_1$-$C_7$-alkoxy); (5) substituted sulfonyl; wherein said substituent is selected from the following moieties: $C_1$-$C_7$-alkyl which is unsubstituted or substituted by one or more substituents selected from deuterium and fluoro; and pyrrolidino which is unsubstituted or substituted by one or more substituents selected from deuterium, hydroxy and oxo; (6) fluoro and chloro; and R[3] is selected from: hydrogen; fluoro; chloro; and optionally substituted methyl; wherein said substituents are independently selected from one to three of the following moieties: deuterium, fluoro, chloro and dimethylamino.

2. The compound of claim 1, wherein

R[1] represents: (1) cyclopropylmethyl or substituted, branched $C_3$-$C_7$-alkyl, wherein said substituents are independently selected from one to nine of the following moieties: deuterium and fluoro; (2) optionally substituted cyclopropyl or cyclobutyl wherein said substituents are independently selected from one to four of the following moieties: methyl, deuterium, fluoro, cyano and aminocarbonyl; (3) optionally substituted phenyl wherein said substituents are independently selected from one to two of the following moieties: deuterium, halo, cyano, $C_1$-$C_7$-alkyl, $C_1$-$C_7$-alkylamino, di($C_1$-$C_7$-alkyl)amino, $C_1$-$C_7$-alkylaminocarbonyl, di($C_1$-$C_7$-alkyl)aminocarbonyl and $C_1$-$C_7$-alkoxy; (4) optionally mono- or di-substituted amine; wherein said substituents are independently selected from the following moieties: deuterium; $C_1$-$C_7$-alkyl which is unsubstituted or substituted by one or more substituents selected from the group of deuterium, fluoro, chloro and hydroxy; phenylsulfonyl which is unsubstituted or substituted by a group selected from $C_1$-$C_7$-alkyl, $C_1$-$C_7$-alkoxy and di($C_1$-$C_7$-alkyl)amino-$C_1$-$C_7$-alkoxy); (5) substituted sulfonyl wherein said substituent is selected from the following moieties: $C_1$-$C_7$-alkyl which is unsubstituted or substituted by deuterium or fluoro; pyrrolidino which is unsubstituted or substituted by a group selected from deuterium, hydroxy and oxo; or (6) fluoro, chloro; and R[3] is selected from hydrogen, methyl, $CD_3$, $CH_2Cl$ and $CH_2F$, $CH_2N(CH_3)_3$.

3. A compound, in free form or in pharmaceutically acceptable salt form, selected from, (S)-Pyrrolidine-1,2-dicarboxylic acid 2-amide 1-{[5-(2-cyclopropyl-pyridin-4-yl)-4-methyl-thiazol-2-yl]-amide};

(S)-Pyrrolidine-1,2-dicarboxylic acid 2-amide 1-({5-[2-(2-fluoro-phenyl)-pyridin-4-yl]-4-methyl-thiazol-2-yl}-amide);

(S)-Pyrrolidine-1,2-dicarboxylic acid 2-amide 1-{[5-(2-cyclobutyl-pyridin-4-yl)-4-methyl-thiazol-2-yl]-amide};

(S)-Pyrrolidine-1,2-dicarboxylic acid 2-amide 1-({4-methyl-5-[2-(1-methyl-cyclopropyl)-pyridin-4-yl]-thiazol-2-yl}-amide);

(S)-Pyrrolidine-1,2-dicarboxylic acid 2-amide 1-({4-methyl-5-[2-(1-methyl-cyclobutyl)-pyridin-4-yl]-thiazol-2-yl}-amide);

(S)-Pyrrolidine-1,2-dicarboxylic acid 2-amide 1-{[5-(2-cyclobutyl-pyridin-4-yl)-thiazol-2-yl]-amide};

(S)-Pyrrolidine-1,2-dicarboxylic acid 2-amide 1-({5-[2-(1-methyl-cyclopropyl)-pyridin-4-yl]-thiazol-2-yl}-amide);

(S)-Pyrrolidine-1,2-dicarboxylic acid 2-amide 1-({5-[2-(1-trifluoromethyl-cyclopropyl)-pyridin-4-yl]-thiazol-2-yl}-amide);

(S)-Pyrrolidine-1,2-dicarboxylic acid 2-amide 1-({5-[2-(2,2,2-trifluoro-1,1-dimethyl-ethyl)-pyridin-4-yl]-thiazol-2-yl}-amide);

(S)-Pyrrolidine-1,2-dicarboxylic acid 2-amide 1-({5-[2-(1-trifluoromethyl-cyclobutyl)-pyridin-4-yl]-thiazol-2-yl}-amide);

(S)-Pyrrolidine-1,2-dicarboxylic acid 2-amide 1-({4-methyl-5-[2-(1-trifluoromethyl-cyclopropyl)-pyridin-4-yl]-thiazol-2-yl}-amide);

(S)-Pyrrolidine-1,2-dicarboxylic acid 2-amide 1-({4-methyl-5-[2-(1-trifluoromethyl-cyclobutyl)-pyridin-4-yl]-thiazol-2-yl}-amide);

(S)-Pyrrolidine-1,2-dicarboxylic acid 2-amide 1-({5-[2-(1-methyl-cyclobutyl)-pyridin-4-yl]-thiazol-2-yl}-amide);

(S)-Pyrrolidine-1,2-dicarboxylic acid 2-amide 1-({5-[2-(1-cyano-cyclopropyl)-pyridin-4-yl]-4-methyl-thiazol-2-yl}-amide);

(S)-Pyrrolidine-1,2-dicarboxylic acid 2-amide 1-({5-[2-(1-cyano-cyclobutyl)-pyridin-4-yl]-4-methyl-thiazol-2-yl}-amide);

(S)-Pyrrolidine-1,2-dicarboxylic acid 2-amide 1-({5-[2-(1-carbamoyl-cyclobutyl)-pyridin-4-yl]-4-methyl-thiazol-2-yl}-amide);

(S)-Pyrrolidine-1,2-dicarboxylic acid 2-amide 1-({5-[2-(2-dimethylamino-1,1-dimethyl-ethyl)-pyridin-4-yl]-4-methyl-thiazol-2-yl}-amide);

(S)-Pyrrolidine-1,2-dicarboxylic acid 2-amide 1-{[5-(2-diethylamino-pyridin-4-yl)-4-methyl-thiazol-2-yl]-amide};

(S)-Pyrrolidine-1,2-dicarboxylic acid 2-amide 1-{[5-(2-diethylamino-pyridin-4-yl)-thiazol-2-yl]-amide};

(S)-Pyrrolidine-1,2-dicarboxylic acid 2-amide 1-[(5-{2-[1-(4-methoxy-phenyl)-1-methyl-ethyl]-pyridin-4-yl}-4-methyl-thiazol-2-yl)-amide];

(S)-Pyrrolidine-1,2-dicarboxylic acid 2-amide 1-[(5-{2-[1-(4-methoxy-phenyl)-1-methyl-ethyl]-pyridin-4-yl}-thiazol-2-yl)-amide];

(S)-Pyrrolidine-1,2-dicarboxylic acid 2-amide 1-[(5-{2-[1-(4-methoxy-phenyl)-cyclopropyl]-pyridin-4-yl}-4-methyl-thiazol-2-yl)-amide];

(S)-Pyrrolidine-1,2-dicarboxylic acid 2-amide 1-[(5-{2-[1-(4-methoxy-phenyl)-cyclopropyl]-pyridin-4-yl}-thiazol-2-yl)-amide];

(S)-Pyrrolidine-1,2-dicarboxylic acid 2-amide 1-{[5-(2-{1-[4-(3-dimethylamino-propoxy)-phenyl]-1-methyl-ethyl}-pyridin-4-yl)-4-methyl-thiazol-2-yl}-amide} (Example 31);

(S)-Pyrrolidine-1,2-dicarboxylic acid 2-amide 1-({4-methyl-5-[2-(1-$d_3$-methyl-cyclobutyl)-pyridin-4-yl]-thiazol-2-yl}-amide);

(S)-Pyrrolidine-1,2-dicarboxylic acid 2-amide 1-({5-[2-(1-$d_3$-methyl-cyclobutyl)-pyridin-4-yl]-thiazol-2-yl}-amide);

(S)-Pyrrolidine-1,2-dicarboxylic acid 2-amide 1-({4-$d_3$-methyl-5-[2-(1-methyl-cyclopropyl)-pyridin-4-yl]-thiazol-2-yl}-amide);

(S)-Pyrrolidine-1,2-dicarboxylic acid 2-amide 1-({4-$d_3$-methyl-5-[2-(2,2,2-trifluoro-1,1-dimethyl-ethyl)-pyridin-4-yl]-thiazol-2-yl}-amide);

(S)-Pyrrolidine-1,2-dicarboxylic acid 2-amide 1-({4-dimethylaminomethyl-5-[2-(1-$d_3$-methyl-cyclobutyl)-pyridin-4-yl]-thiazol-2-yl}-amide);

(S)-Pyrrolidine-1,2-dicarboxylic acid 2-amide 1-({4-chloro-5-[2-(2,2,2-trifluoro-1,1-dimethyl-ethyl)-pyridin-4-yl]-thiazol-2-yl}-amide); and (S)-Pyrrolidine-1,2-dicarboxylic acid 2-amide 1-({4-fluoromethyl-5-[2-(2,2,2-trifluoro-1,1-dimethyl-ethyl)-pyridin-4-yl]-thiazol-2-yl}-amide);

(S)-Pyrrolidine-1,2-dicarboxylic acid 2-amide 1-({5-[2-(2-fluoro-1,1-dimethyl-ethyl)-pyridin-4-yl]-4-methyl-thiazol-2-yl}-amide); and (S)-Pyrrolidine-1,2-dicarboxylic acid 2-amide 1-({5-[2-(2-fluoro-1-fluoromethyl-1-methyl-ethyl)-pyridin-4-yl]-4-methyl-thiazol-2-yl}-amide.

4. A method of treatment of a proliferative disease, comprising the step of administering to a subject in need thereof a therapeutically effective amount of a compound of claim 3 in free form or in pharmaceutically acceptable salt form, wherein the proliferative disease is selected from the group consisting of melanoma, colorectal adenoma and cancers of the breast, and pancreas.

5. A pharmaceutical composition comprising a therapeutically effective amount of a compound of claim 1 in free form or in pharmaceutically acceptable salt form and one or more pharmaceutically acceptable carrier.

* * * * *

SEQUENCE LISTING

<160> NUMBER OF SEQ ID NOS: 26

<210> SEQ ID NO 1
<211> LENGTH: 42
<212> TYPE: DNA
<213> ORGANISM: Artificial
<220> FEATURE:
<223> OTHER INFORMATION: PCR Primer

<400> SEQUENCE: 1
gctagcatgc gagaatatga tagattatat gaagaatata cc                42

<210> SEQ ID NO 2
<211> LENGTH: 45
<212> TYPE: DNA
<213> ORGANISM: Artificial
<220> FEATURE:
<223> OTHER INFORMATION: PCR primer

<400> SEQUENCE: 2
gcctccacca cctccgcctg gtttaatgct gttcatacgt ttgtc             45

<210> SEQ ID NO 3
<211> LENGTH: 42
<212> TYPE: DNA
<213> ORGANISM: Artificial
<220> FEATURE:
<223> OTHER INFORMATION: PCR primer

<400> SEQUENCE: 3
tactagtccg cctccaccac ctccgcctcc accacctccg cc                42

<210> SEQ ID NO 4
<211> LENGTH: 1180
<212> TYPE: PRT
<213> ORGANISM: Artificial
<220> FEATURE:
<223> OTHER INFORMATION: PI3K kinase construct

<400> SEQUENCE: 4

Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Gly Gly Gly Gly Gly Leu Val Glu Cys Leu Leu Pro
        115                 120                 125

Asn Gly Met Ile Val Thr Leu Glu Cys Leu Arg Glu Ala Thr Leu Ile
    130                 135                 140

Thr Ile Lys His Glu Leu Phe Lys Glu Ala Arg Lys Tyr Pro Leu His
145                 150                 155                 160

```
Gln Leu Leu Gln Asp Glu Ser Ser Tyr Ile Phe Val Ser Val Thr Gln
            165                 170                 175

Glu Ala Glu Arg Glu Phe Phe Asp Glu Thr Arg Arg Leu Cys Asp
        180                 185                 190

Leu Arg Leu Phe Gln Pro Phe Leu Lys Val Ile Glu Pro Val Gly Asn
            195                 200                 205

Arg Glu Glu Lys Ile Leu Asn Arg Glu Ile Gly Phe Ala Ile Gly Met
        210                 215                 220

Pro Val Cys Glu Phe Asp Met Val Lys Asp Pro Glu Val Gln Asp Phe
225                 230                 235                 240

Arg Arg Asn Ile Leu Asn Val Cys Lys Glu Ala Val Asp Leu Arg Asp
                245                 250                 255

Leu Asn Ser Pro His Ser Arg Ala Met Tyr Val Tyr Pro Pro Asn Val
            260                 265                 270

Glu Ser Ser Pro Glu Leu Pro Lys His Ile Tyr Asn Lys Leu Asp Lys
        275                 280                 285

Gly Gln Ile Ile Val Val Ile Trp Val Ile Val Ser Pro Asn Asn Asp
            290                 295                 300

Lys Gln Lys Tyr Thr Leu Lys Ile Asn His Asp Cys Val Pro Glu Gln
305                 310                 315                 320

Val Ile Ala Glu Ala Ile Arg Lys Lys Thr Arg Ser Met Leu Leu Ser
                325                 330                 335

Ser Glu Gln Leu Lys Leu Cys Val Leu Glu Tyr Gln Gly Lys Tyr Ile
            340                 345                 350

Leu Lys Val Cys Gly Cys Asp Tyr Phe Leu Glu Lys Tyr Pro Leu
            355                 360                 365

Ser Gln Tyr Lys Tyr Ile Arg Ser Cys Ile Met Leu Gly Arg Met Pro
        370                 375                 380

Asn Leu Met Leu Met Ala Lys Glu Ser Leu Tyr Ser Gln Leu Pro Met
385                 390                 395                 400

Asp Cys Phe Thr Met Pro Ser Tyr Ser Arg Arg Ile Ser Thr Ala Thr
                405                 410                 415

Pro Tyr Met Asn Gly Glu Thr Ser Thr Lys Ser Leu Trp Val Ile Asn
            420                 425                 430

Ser Ala Leu Arg Ile Lys Ile Leu Cys Ala Thr Tyr Val Asn Val Asn
        435                 440                 445

Ile Arg Asp Ile Asp Lys Ile Tyr Val Arg Thr Gly Ile Tyr His Gly
    450                 455                 460

Gly Glu Pro Leu Cys Asp Asn Val Asn Thr Gln Arg Val Pro Cys Ser
465                 470                 475                 480

Asn Pro Arg Trp Asn Glu Trp Leu Asn Tyr Asp Ile Tyr Ile Pro Asp
            485                 490                 495

Leu Pro Arg Ala Ala Arg Leu Cys Leu Ser Ile Cys Ser Val Lys Gly
        500                 505                 510

Arg Lys Gly Ala Lys Glu Glu His Cys Pro Leu Ala Trp Gly Asn Ile
    515                 520                 525

Asn Leu Phe Asp Tyr Thr Asp Thr Leu Val Ser Gly Lys Met Ala Leu
        530                 535                 540

Asn Leu Trp Pro Val Pro His Gly Leu Glu Asp Leu Leu Asn Pro Ile
545                 550                 555                 560

Gly Val Thr Gly Ser Asn Pro Asn Lys Glu Thr Pro Cys Leu Glu Leu
                565                 570                 575

Glu Phe Asp Trp Phe Ser Ser Val Val Lys Phe Pro Asp Met Ser Val
            580                 585                 590
```

```
Ile Glu Glu His Ala Asn Trp Ser Val Ser Arg Glu Ala Gly Phe Ser
            595                 600                 605

Tyr Ser His Ala Gly Leu Ser Asn Arg Leu Ala Arg Asp Asn Glu Leu
        610                 615                 620

Arg Glu Asn Asp Lys Glu Gln Leu Lys Ala Ile Ser Thr Arg Asp Pro
625                 630                 635                 640

Leu Ser Glu Ile Thr Glu Gln Glu Lys Asp Phe Leu Trp Ser His Arg
                645                 650                 655

His Tyr Cys Val Thr Ile Pro Glu Ile Leu Pro Lys Leu Leu Leu Ser
            660                 665                 670

Val Lys Trp Asn Ser Arg Asp Glu Val Ala Gln Met Tyr Cys Leu Val
        675                 680                 685

Lys Asp Trp Pro Pro Ile Lys Pro Glu Gln Ala Met Glu Leu Leu Asp
690                 695                 700

Cys Asn Tyr Pro Asp Pro Met Val Arg Gly Phe Ala Val Arg Cys Leu
705                 710                 715                 720

Glu Lys Tyr Leu Thr Asp Asp Lys Leu Ser Gln Tyr Leu Ile Gln Leu
                725                 730                 735

Val Gln Val Leu Lys Tyr Glu Gln Tyr Leu Asp Asn Leu Leu Val Arg
            740                 745                 750

Phe Leu Leu Lys Lys Ala Leu Thr Asn Gln Arg Ile Gly His Phe Phe
        755                 760                 765

Phe Trp His Leu Lys Ser Glu Met His Asn Lys Thr Val Ser Gln Arg
770                 775                 780

Phe Gly Leu Leu Leu Glu Ser Tyr Cys Arg Ala Cys Gly Met Tyr Leu
785                 790                 795                 800

Lys His Leu Asn Arg Gln Val Glu Ala Met Glu Lys Leu Ile Asn Leu
                805                 810                 815

Thr Asp Ile Leu Lys Gln Glu Lys Lys Asp Glu Thr Gln Lys Val Gln
            820                 825                 830

Met Lys Phe Leu Val Glu Gln Met Arg Arg Pro Asp Phe Met Asp Ala
        835                 840                 845

Leu Gln Gly Phe Leu Ser Pro Leu Asn Pro Ala His Gln Leu Gly Asn
850                 855                 860

Leu Arg Leu Glu Glu Cys Arg Ile Met Ser Ser Ala Lys Arg Pro Leu
865                 870                 875                 880

Trp Leu Asn Trp Glu Asn Pro Asp Ile Met Ser Glu Leu Leu Phe Gln
                885                 890                 895

Asn Asn Glu Ile Ile Phe Lys Asn Gly Asp Asp Leu Arg Gln Asp Met
            900                 905                 910

Leu Thr Leu Gln Ile Ile Arg Ile Met Glu Asn Ile Trp Gln Asn Gln
        915                 920                 925

Gly Leu Asp Leu Arg Met Leu Pro Tyr Gly Cys Leu Ser Ile Gly Asp
930                 935                 940

Cys Val Gly Leu Ile Glu Val Val Arg Asn Ser His Thr Ile Met Gln
945                 950                 955                 960

Ile Gln Cys Lys Gly Gly Leu Lys Gly Ala Leu Gln Phe Asn Ser His
                965                 970                 975

Thr Leu His Gln Trp Leu Lys Asp Lys Asn Lys Gly Glu Ile Tyr Asp
            980                 985                 990

Ala Ala Ile Asp Leu Phe Thr Arg  Ser Cys Ala Gly Tyr  Cys Val Ala
        995                 1000                 1005

Thr Phe  Ile Leu Gly Ile Gly  Asp Arg His Asn Ser  Asn Ile Met
```

```
            1010                1015                1020

Val Lys Asp Asp Gly Gln Leu Phe His Ile Asp Phe Gly His Phe
    1025                1030                1035

Leu Asp His Lys Lys Lys Phe Gly Tyr Lys Arg Glu Arg Val
    1040                1045                1050

Pro Phe Val Leu Thr Gln Asp Phe Leu Ile Val Ile Ser Lys Gly
    1055                1060                1065

Ala Gln Glu Cys Thr Lys Thr Arg Glu Phe Glu Arg Phe Gln Glu
    1070                1075                1080

Met Cys Tyr Lys Ala Tyr Leu Ala Ile Arg Gln His Ala Asn Leu
    1085                1090                1095

Phe Ile Asn Leu Phe Ser Met Met Leu Gly Ser Gly Met Pro Glu
    1100                1105                1110

Leu Gln Ser Phe Asp Asp Ile Ala Tyr Ile Arg Lys Thr Leu Ala
    1115                1120                1125

Leu Asp Lys Thr Glu Gln Glu Ala Leu Glu Tyr Phe Met Lys Gln
    1130                1135                1140

Met Asn Asp Ala His His Gly Gly Trp Thr Thr Lys Met Asp Trp
    1145                1150                1155

Ile Phe His Thr Ile Lys Gln His Ala Leu Asn Glu Leu Gly Gly
    1160                1165                1170

Ala His His His His His His
    1175                1180

<210> SEQ ID NO 5
<211> LENGTH: 28
<212> TYPE: DNA
<213> ORGANISM: Artificial
<220> FEATURE:
<223> OTHER INFORMATION: PCR primer

<400> SEQUENCE: 5
cgagaatatg atagattata tgaagaat                                       28

<210> SEQ ID NO 6
<211> LENGTH: 30
<212> TYPE: DNA
<213> ORGANISM: Artificial
<220> FEATURE:
<223> OTHER INFORMATION: PCR primer

<400> SEQUENCE: 6
tggtttaatg ctgttcatac gtttgtcaat                                     30

<210> SEQ ID NO 7
<211> LENGTH: 76
<212> TYPE: DNA
<213> ORGANISM: Artificial
<220> FEATURE:
<223> OTHER INFORMATION: PCR primer

<400> SEQUENCE: 7
gggacaagtt tgtacaaaaa agcaggctac gaaggagata tacatatgcg agaatatgat   60
agattatatg aagaat                                                    76

<210> SEQ ID NO 8
<211> LENGTH: 54
<212> TYPE: DNA
<213> ORGANISM: Artificial
<220> FEATURE:
<223> OTHER INFORMATION: PCR primer
```

<400> SEQUENCE: 8

```
actgaagcat cctcctcctc ctcctcctgg tttaatgctg ttcatacgtt tgtc          54
```

<210> SEQ ID NO 9
<211> LENGTH: 54
<212> TYPE: DNA
<213> ORGANISM: Artificial
<220> FEATURE:
<223> OTHER INFORMATION: PCR primer

<400> SEQUENCE: 9

```
attaaaccag gaggaggagg aggaggatgc ttcagtttca taatgcctcc tgct          54
```

<210> SEQ ID NO 10
<211> LENGTH: 57
<212> TYPE: DNA
<213> ORGANISM: Artificial
<220> FEATURE:
<223> OTHER INFORMATION: PCR primer

<400> SEQUENCE: 10

```
agctccgtga tggtgatggt gatgtgctcc agatctgtag tctttccgaa ctgtgtg      57
```

<210> SEQ ID NO 11
<211> LENGTH: 61
<212> TYPE: DNA
<213> ORGANISM: Artificial
<220> FEATURE:
<223> OTHER INFORMATION: PCR primer

<400> SEQUENCE: 11

```
gggaccactt tgtacaagaa agctgggttt aagctccgtg atggtgatgg tgatgtgctc   60
c                                                                  61
```

<210> SEQ ID NO 12
<211> LENGTH: 1194
<212> TYPE: PRT
<213> ORGANISM: Artificial
<220> FEATURE:
<223> OTHER INFORMATION: PI3K kinase construct

<400> SEQUENCE: 12

```
Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Lys Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Cys Phe Ser Phe Ile Met Pro Pro Ala Met Ala Asp Ile
        115                 120                 125

Leu Asp Ile Trp Ala Val Asp Ser Gln Ile Ala Ser Asp Gly Ser Ile
    130                 135                 140
```

```
Pro Val Asp Phe Leu Leu Pro Thr Gly Ile Tyr Ile Gln Leu Glu Val
145                 150                 155                 160

Pro Arg Glu Ala Thr Ile Ser Tyr Ile Lys Gln Met Leu Trp Lys Gln
                165                 170                 175

Val His Asn Tyr Pro Met Phe Asn Leu Leu Met Asp Ile Asp Ser Tyr
            180                 185                 190

Met Phe Ala Cys Val Asn Gln Thr Ala Val Tyr Glu Glu Leu Glu Asp
        195                 200                 205

Glu Thr Arg Arg Leu Cys Asp Val Arg Pro Phe Leu Pro Val Leu Lys
    210                 215                 220

Leu Val Thr Arg Ser Cys Asp Pro Gly Glu Lys Leu Asp Ser Lys Ile
225                 230                 235                 240

Gly Val Leu Ile Gly Lys Gly Leu His Glu Phe Asp Ser Leu Lys Asp
                245                 250                 255

Pro Glu Val Asn Glu Phe Arg Arg Lys Met Arg Lys Phe Ser Glu Glu
            260                 265                 270

Lys Ile Leu Ser Leu Val Gly Leu Ser Trp Met Asp Trp Leu Lys Gln
        275                 280                 285

Thr Tyr Pro Pro Glu His Glu Pro Ser Ile Pro Glu Asn Leu Glu Asp
    290                 295                 300

Lys Leu Tyr Gly Gly Lys Leu Ile Val Ala Val His Phe Glu Asn Cys
305                 310                 315                 320

Gln Asp Val Phe Ser Phe Val Ser Pro Asn Met Asn Pro Ile Lys
                325                 330                 335

Val Asn Glu Leu Ala Ile Gln Lys Arg Leu Thr Ile His Gly Lys Glu
            340                 345                 350

Asp Glu Val Ser Pro Tyr Asp Tyr Val Leu Gln Val Ser Gly Arg Val
        355                 360                 365

Glu Tyr Val Phe Gly Asp His Pro Leu Ile Gln Phe Gln Tyr Ile Arg
    370                 375                 380

Asn Cys Val Met Asn Arg Ala Leu Pro His Phe Ile Leu Val Glu Cys
385                 390                 395                 400

Cys Lys Ile Lys Lys Met Tyr Glu Gln Glu Met Ile Ala Ile Glu Ala
                405                 410                 415

Ala Ile Asn Arg Asn Ser Ser Asn Leu Pro Leu Pro Leu Pro Pro Lys
            420                 425                 430

Lys Thr Arg Ile Ile Ser His Val Trp Glu Asn Asn Pro Phe Gln
        435                 440                 445

Ile Val Leu Val Lys Gly Asn Lys Leu Asn Thr Glu Thr Val Lys
450                 455                 460

Val His Val Arg Ala Gly Leu Phe His Gly Thr Glu Leu Leu Cys Lys
465                 470                 475                 480

Thr Ile Val Ser Ser Glu Val Ser Gly Lys Asn Asp His Ile Trp Asn
                485                 490                 495

Glu Pro Leu Glu Phe Asp Ile Asn Ile Cys Asp Leu Pro Arg Met Ala
            500                 505                 510

Arg Leu Cys Phe Ala Val Tyr Ala Val Leu Asp Lys Val Lys Thr Lys
        515                 520                 525

Lys Ser Thr Lys Thr Ile Asn Pro Ser Lys Tyr Gln Thr Ile Arg Lys
    530                 535                 540

Ala Gly Lys Val His Tyr Pro Val Ala Trp Val Asn Thr Met Val Phe
545                 550                 555                 560

Asp Phe Lys Gly Gln Leu Arg Thr Gly Asp Ile Ile Leu His Ser Trp
                565                 570                 575
```

```
Ser Ser Phe Pro Asp Glu Leu Glu Met Leu Asn Pro Met Gly Thr
            580                 585                 590
Val Gln Thr Asn Pro Tyr Thr Glu Asn Ala Thr Ala Leu His Val Lys
        595                 600                 605
Phe Pro Glu Asn Lys Lys Gln Pro Tyr Tyr Pro Pro Phe Asp Lys
    610                 615                 620
Ile Ile Glu Lys Ala Ala Glu Ile Ala Ser Ser Asp Ser Ala Asn Val
625                 630                 635                 640
Ser Ser Arg Gly Gly Lys Lys Phe Leu Pro Val Leu Lys Glu Ile Leu
                645                 650                 655
Asp Arg Asp Pro Leu Ser Gln Leu Cys Glu Asn Glu Met Asp Leu Ile
                660                 665                 670
Trp Thr Leu Arg Gln Asp Cys Arg Glu Ile Phe Pro Gln Ser Leu Pro
            675                 680                 685
Lys Leu Leu Leu Ser Ile Lys Trp Asn Lys Leu Glu Asp Val Ala Gln
        690                 695                 700
Leu Gln Ala Leu Leu Gln Ile Trp Pro Lys Leu Pro Pro Arg Glu Ala
705                 710                 715                 720
Leu Glu Leu Leu Asp Phe Asn Tyr Pro Asp Gln Tyr Val Arg Glu Tyr
                725                 730                 735
Ala Val Gly Cys Leu Arg Gln Met Ser Asp Glu Glu Leu Ser Gln Tyr
            740                 745                 750
Leu Leu Gln Leu Val Gln Val Leu Lys Tyr Glu Pro Phe Leu Asp Cys
        755                 760                 765
Ala Leu Ser Arg Phe Leu Leu Glu Arg Ala Leu Gly Asn Arg Arg Ile
    770                 775                 780
Gly Gln Phe Leu Phe Trp His Leu Arg Ser Glu Val His Ile Pro Ala
785                 790                 795                 800
Val Ser Val Gln Phe Gly Val Ile Leu Glu Ala Tyr Cys Arg Gly Ser
                805                 810                 815
Val Gly His Met Lys Val Leu Ser Lys Gln Val Glu Ala Leu Asn Lys
            820                 825                 830
Leu Lys Thr Leu Asn Ser Leu Ile Lys Leu Asn Ala Val Lys Leu Asn
        835                 840                 845
Arg Ala Lys Gly Lys Glu Ala Met His Thr Cys Leu Lys Gln Ser Ala
    850                 855                 860
Tyr Arg Glu Ala Leu Ser Asp Leu Gln Ser Pro Leu Asn Pro Cys Val
865                 870                 875                 880
Ile Leu Ser Glu Leu Tyr Val Glu Lys Cys Lys Tyr Met Asp Ser Lys
                885                 890                 895
Met Lys Pro Leu Trp Leu Val Tyr Asn Asn Lys Val Phe Gly Glu Asp
            900                 905                 910
Ser Val Gly Val Ile Phe Lys Asn Gly Asp Asp Leu Arg Gln Asp Met
        915                 920                 925
Leu Thr Leu Gln Met Leu Arg Leu Met Asp Leu Leu Trp Lys Glu Ala
    930                 935                 940
Gly Leu Asp Leu Arg Met Leu Pro Tyr Gly Cys Leu Ala Thr Gly Asp
945                 950                 955                 960
Arg Ser Gly Leu Ile Glu Val Val Ser Thr Ser Glu Thr Ile Ala Asp
                965                 970                 975
Ile Gln Leu Asn Ser Ser Asn Val Ala Ala Ala Ala Phe Asn Lys
            980                 985                 990
Asp Ala Leu Leu Asn Trp Leu Lys  Glu Tyr Asn Ser Gly  Asp Asp Leu
```

```
                     995                1000               1005
Asp Arg Ala Ile Glu Glu Phe Thr Leu Ser Cys Ala Gly Tyr Cys
    1010                1015               1020

Val Ala Ser Tyr Val Leu Gly Ile Gly Asp Arg His Ser Asp Asn
    1025                1030               1035

Ile Met Val Lys Lys Thr Gly Gln Leu Phe His Ile Asp Phe Gly
    1040                1045               1050

His Ile Leu Gly Asn Phe Lys Ser Lys Phe Gly Ile Lys Arg Glu
    1055                1060               1065

Arg Val Pro Phe Ile Leu Thr Tyr Asp Phe Ile His Val Ile Gln
    1070                1075               1080

Gln Gly Lys Thr Gly Asn Thr Glu Lys Phe Gly Arg Phe Arg Gln
    1085                1090               1095

Cys Cys Glu Asp Ala Tyr Leu Ile Leu Arg Arg His Gly Asn Leu
    1100                1105               1110

Phe Ile Thr Leu Phe Ala Leu Met Leu Thr Ala Gly Leu Pro Glu
    1115                1120               1125

Leu Thr Ser Val Lys Asp Ile Gln Tyr Leu Lys Asp Ser Leu Ala
    1130                1135               1140

Leu Gly Lys Ser Glu Glu Ala Leu Lys Gln Phe Lys Gln Lys
    1145                1150               1155

Phe Asp Glu Ala Leu Arg Glu Ser Trp Thr Thr Lys Val Asn Trp
    1160                1165               1170

Met Ala His Thr Val Arg Lys Asp Tyr Arg Ser Gly Ala His His
    1175                1180               1185

His His His His Gly Ala
    1190

<210> SEQ ID NO 13
<211> LENGTH: 966
<212> TYPE: PRT
<213> ORGANISM: Artificial
<220> FEATURE:
<223> OTHER INFORMATION: PI3K kinase construct

<400> SEQUENCE: 13

Met Ser Glu Glu Ser Gln Ala Phe Gln Arg Gln Leu Thr Ala Leu Ile
1               5                   10                  15

Gly Tyr Asp Val Thr Asp Val Ser Asn Val His Asp Asp Glu Leu Glu
                20                  25                  30

Phe Thr Arg Arg Gly Leu Val Thr Pro Arg Met Ala Glu Val Ala Ser
            35                  40                  45

Arg Asp Pro Lys Leu Tyr Ala Met His Pro Trp Val Thr Ser Lys Pro
        50                  55                  60

Leu Pro Glu Tyr Leu Trp Lys Lys Ile Ala Asn Asn Cys Ile Phe Ile
65                  70                  75                  80

Val Ile His Arg Ser Thr Thr Ser Gln Thr Ile Lys Val Ser Pro Asp
                85                  90                  95

Asp Thr Pro Gly Ala Ile Leu Gln Ser Phe Thr Lys Met Ala Lys
            100                 105                 110

Lys Lys Ser Leu Met Asp Ile Pro Glu Ser Gln Ser Glu Gln Asp Phe
        115                 120                 125

Val Leu Arg Val Cys Gly Arg Asp Glu Tyr Leu Val Gly Glu Thr Pro
    130                 135                 140

Ile Lys Asn Phe Gln Trp Val Arg His Cys Leu Lys Asn Gly Glu Glu
145                 150                 155                 160
```

```
Ile His Val Val Leu Asp Thr Pro Pro Asp Pro Ala Leu Asp Glu Val
            165                 170                 175

Arg Lys Glu Glu Trp Pro Leu Val Asp Asp Cys Thr Gly Val Thr Gly
            180                 185                 190

Tyr His Glu Gln Leu Thr Ile His Gly Lys Asp His Glu Ser Val Phe
            195                 200                 205

Thr Val Ser Leu Trp Asp Cys Asp Arg Lys Phe Arg Val Lys Ile Arg
            210                 215                 220

Gly Ile Asp Ile Pro Val Leu Pro Arg Asn Thr Asp Leu Thr Val Phe
225                 230                 235                 240

Val Glu Ala Asn Ile Gln His Gly Gln Gln Val Leu Cys Gln Arg Arg
                245                 250                 255

Thr Ser Pro Lys Pro Phe Thr Glu Glu Val Leu Trp Asn Val Trp Leu
            260                 265                 270

Glu Phe Ser Ile Lys Ile Lys Asp Leu Pro Lys Gly Ala Leu Leu Asn
            275                 280                 285

Leu Gln Ile Tyr Cys Gly Lys Ala Pro Ala Leu Ser Ser Lys Ala Ser
            290                 295                 300

Ala Glu Ser Pro Ser Ser Glu Ser Lys Gly Lys Val Arg Leu Leu Tyr
305                 310                 315                 320

Tyr Val Asn Leu Leu Ile Asp His Arg Phe Leu Leu Arg Arg Gly
            325                 330                 335

Glu Tyr Val Leu His Met Trp Gln Ile Ser Gly Lys Gly Glu Asp Gln
            340                 345                 350

Gly Ser Phe Asn Ala Asp Lys Leu Thr Ser Ala Thr Asn Pro Asp Lys
            355                 360                 365

Glu Asn Ser Met Ser Ile Ser Ile Leu Leu Asp Asn Tyr Cys His Pro
            370                 375                 380

Ile Ala Leu Pro Lys His Gln Pro Thr Pro Asp Pro Glu Gly Asp Arg
385                 390                 395                 400

Val Arg Ala Glu Met Pro Asn Gln Leu Arg Lys Gln Leu Glu Ala Ile
            405                 410                 415

Ile Ala Thr Asp Pro Leu Asn Pro Leu Thr Ala Glu Asp Lys Glu Leu
            420                 425                 430

Leu Trp His Phe Arg Tyr Glu Ser Leu Lys His Pro Lys Ala Tyr Pro
            435                 440                 445

Lys Leu Phe Ser Ser Val Lys Trp Gly Gln Gln Glu Ile Val Ala Lys
            450                 455                 460

Thr Tyr Gln Leu Leu Ala Arg Arg Glu Val Trp Asp Gln Ser Ala Leu
465                 470                 475                 480

Asp Val Gly Leu Thr Met Gln Leu Leu Asp Cys Asn Phe Ser Asp Glu
                485                 490                 495

Asn Val Arg Ala Ile Ala Val Gln Lys Leu Glu Ser Leu Glu Asp Asp
            500                 505                 510

Asp Val Leu His Tyr Leu Leu Gln Leu Val Gln Ala Val Lys Phe Glu
            515                 520                 525

Pro Tyr His Asp Ser Ala Leu Ala Arg Phe Leu Leu Lys Arg Gly Leu
            530                 535                 540

Arg Asn Lys Arg Ile Gly His Phe Leu Phe Trp Phe Leu Arg Ser Glu
545                 550                 555                 560

Ile Ala Gln Ser Arg His Tyr Gln Gln Arg Phe Ala Val Ile Leu Glu
                565                 570                 575

Ala Tyr Leu Arg Gly Cys Gly Thr Ala Met Leu His Asp Phe Thr Gln
```

```
                    580                 585                 590
Gln Val Gln Val Ile Glu Met Leu Gln Lys Val Thr Leu Asp Ile Lys
                595                 600                 605

Ser Leu Ser Ala Glu Lys Tyr Asp Val Ser Ser Gln Val Ile Ser Gln
610                 615                 620

Leu Lys Gln Lys Leu Glu Asn Leu Gln Asn Ser Gln Leu Pro Glu Ser
625                 630                 635                 640

Phe Arg Val Pro Tyr Asp Pro Gly Leu Lys Ala Gly Ala Leu Ala Ile
                645                 650                 655

Glu Lys Cys Lys Val Met Ala Ser Lys Lys Pro Leu Trp Leu Glu
                660                 665                 670

Phe Lys Cys Ala Asp Pro Thr Ala Leu Ser Asn Glu Thr Ile Gly Ile
                675                 680                 685

Ile Phe Lys His Gly Asp Asp Leu Arg Gln Asp Met Leu Ile Leu Gln
                690                 695                 700

Ile Leu Arg Ile Met Glu Ser Ile Trp Glu Thr Glu Ser Leu Asp Leu
705                 710                 715                 720

Cys Leu Leu Pro Tyr Gly Cys Ile Ser Thr Gly Asp Lys Ile Gly Met
                725                 730                 735

Ile Glu Ile Val Lys Asp Ala Thr Thr Ile Ala Lys Ile Gln Gln Ser
                740                 745                 750

Thr Val Gly Asn Thr Gly Ala Phe Lys Asp Glu Val Leu Asn His Trp
                755                 760                 765

Leu Lys Glu Lys Ser Pro Thr Glu Glu Lys Phe Gln Ala Ala Val Glu
770                 775                 780

Arg Phe Val Tyr Ser Cys Ala Gly Tyr Cys Val Ala Thr Phe Val Leu
785                 790                 795                 800

Gly Ile Gly Asp Arg His Asn Asp Asn Ile Met Ile Thr Glu Thr Gly
                805                 810                 815

Asn Leu Phe His Ile Asp Phe Gly His Ile Leu Gly Asn Tyr Lys Ser
                820                 825                 830

Phe Leu Gly Ile Asn Lys Glu Arg Val Pro Phe Val Leu Thr Pro Asp
                835                 840                 845

Phe Leu Phe Val Met Gly Thr Ser Gly Lys Lys Thr Ser Pro His Phe
                850                 855                 860

Gln Lys Phe Gln Asp Ile Cys Val Lys Ala Tyr Leu Ala Leu Arg His
865                 870                 875                 880

His Thr Asn Leu Leu Ile Ile Leu Phe Ser Met Met Leu Met Thr Gly
                885                 890                 895

Met Pro Gln Leu Thr Ser Lys Glu Asp Ile Glu Tyr Ile Arg Asp Ala
                900                 905                 910

Leu Thr Val Gly Lys Asn Glu Glu Asp Ala Lys Lys Tyr Phe Leu Asp
                915                 920                 925

Gln Ile Glu Val Cys Arg Asp Lys Gly Trp Thr Val Gln Phe Asn Trp
                930                 935                 940

Phe Leu His Leu Val Leu Gly Ile Lys Gln Gly Glu Lys His Ser Ala
945                 950                 955                 960

His His His His His His
                965

<210> SEQ ID NO 14
<211> LENGTH: 45
<212> TYPE: DNA
<213> ORGANISM: Artificial
<220> FEATURE:
```

-continued

<223> OTHER INFORMATION: PCR primer

<400> SEQUENCE: 14
tcctcctcct cctcctcctg gtttaatgct gttcatacgt ttgtc        45

<210> SEQ ID NO 15
<211> LENGTH: 26
<212> TYPE: DNA
<213> ORGANISM: Artificial
<220> FEATURE:
<223> OTHER INFORMATION: PCR primer

<400> SEQUENCE: 15
atgccccctg gggtggactg ccccat        26

<210> SEQ ID NO 16
<211> LENGTH: 26
<212> TYPE: DNA
<213> ORGANISM: Artificial
<220> FEATURE:
<223> OTHER INFORMATION: PCR primer

<400> SEQUENCE: 16
ctactgcctg ttgtctttgg acacgt        26

<210> SEQ ID NO 17
<211> LENGTH: 53
<212> TYPE: DNA
<213> ORGANISM: Artificial
<220> FEATURE:
<223> OTHER INFORMATION: PCR primer

<400> SEQUENCE: 17
attaaaccag gaggaggagg aggaggaccc cctggggtgg actgccccat gga        53

<210> SEQ ID NO 18
<211> LENGTH: 56
<212> TYPE: DNA
<213> ORGANISM: Artificial
<220> FEATURE:
<223> OTHER INFORMATION: PCR primer

<400> SEQUENCE: 18
agctccgtga tggtgatggt gatgtgctcc ctgcctgttg tctttggaca cgttgt        56

<210> SEQ ID NO 19
<211> LENGTH: 60
<212> TYPE: DNA
<213> ORGANISM: Artificial
<220> FEATURE:
<223> OTHER INFORMATION: PCR primer

<400> SEQUENCE: 19
gggaccactt tgtacaagaa agctgggttt aagctccgtg atggtgatgg tgagtgctcc        60

<210> SEQ ID NO 20
<211> LENGTH: 1169
<212> TYPE: PRT
<213> ORGANISM: Artificial
<220> FEATURE:
<223> OTHER INFORMATION: PI3K kinase construct

<400> SEQUENCE: 20

Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile

```
                  20                  25                  30
Lys Ile Phe Glu Glu Gln Cys Gln Thr Gln Glu Arg Tyr Ser Lys Glu
            35                  40                  45

Tyr Ile Glu Lys Phe Lys Arg Glu Gly Asn Glu Lys Glu Ile Gln Arg
        50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Pro Pro Gly Val Asp Cys Pro Met Glu Phe Trp Thr Lys
        115                 120                 125

Glu Glu Asn Gln Ser Val Val Asp Phe Leu Leu Pro Thr Gly Val
            130                 135                 140

Tyr Leu Asn Phe Pro Val Ser Arg Asn Ala Asn Leu Ser Thr Ile Lys
145                 150                 155                 160

Gln Leu Leu Trp His Arg Ala Gln Tyr Glu Pro Leu Phe His Met Leu
                165                 170                 175

Ser Gly Pro Glu Ala Tyr Val Phe Thr Cys Ile Asn Gln Thr Ala Glu
            180                 185                 190

Gln Gln Glu Leu Glu Asp Glu Arg Arg Leu Cys Asp Val Gln Pro
        195                 200                 205

Phe Leu Pro Val Leu Arg Leu Val Ala Arg Glu Gly Asp Arg Val Lys
        210                 215                 220

Lys Leu Ile Asn Ser Gln Ile Ser Leu Leu Ile Gly Lys Gly Leu His
225                 230                 235                 240

Glu Phe Asp Ser Leu Cys Asp Pro Glu Val Asn Asp Phe Arg Ala Lys
                245                 250                 255

Met Cys Gln Phe Cys Glu Glu Ala Ala Arg Arg Gln Gln Leu Gly
            260                 265                 270

Trp Glu Ala Trp Leu Gln Tyr Ser Phe Pro Leu Gln Leu Glu Pro Ser
        275                 280                 285

Ala Gln Thr Trp Gly Pro Gly Thr Leu Arg Leu Pro Asn Arg Ala Leu
            290                 295                 300

Leu Val Asn Val Lys Phe Glu Gly Ser Glu Glu Ser Phe Thr Phe Gln
305                 310                 315                 320

Val Ser Thr Lys Asp Val Pro Leu Ala Leu Met Ala Cys Ala Leu Arg
                325                 330                 335

Lys Lys Ala Thr Val Phe Arg Gln Pro Leu Val Glu Gln Pro Glu Asp
            340                 345                 350

Tyr Thr Leu Gln Val Asn Gly Arg His Glu Tyr Leu Tyr Gly Ser Tyr
        355                 360                 365

Pro Leu Cys Gln Phe Gln Tyr Ile Cys Ser Cys Leu His Ser Gly Leu
        370                 375                 380

Thr Pro His Leu Thr Met Val His Ser Ser Ile Leu Ala Met Arg
385                 390                 395                 400

Asp Glu Gln Ser Asn Pro Ala Pro Gln Val Gln Lys Pro Arg Ala Lys
                405                 410                 415

Pro Pro Pro Ile Pro Ala Lys Lys Pro Ser Ser Val Ser Leu Trp Ser
            420                 425                 430

Leu Glu Gln Pro Phe Arg Ile Glu Leu Ile Gln Gly Ser Lys Val Asn
        435                 440                 445
```

-continued

```
Ala Asp Glu Arg Met Lys Leu Val Gln Ala Gly Leu Phe His Gly
450                 455                 460

Asn Glu Met Leu Cys Lys Thr Val Ser Ser Glu Val Ser Val Cys
465                 470                 475                 480

Ser Glu Pro Val Trp Lys Gln Arg Leu Glu Phe Asp Ile Asn Ile Cys
                485                 490                 495

Asp Leu Pro Arg Met Ala Arg Leu Cys Phe Ala Leu Tyr Ala Val Ile
            500                 505                 510

Glu Lys Ala Lys Lys Ala Arg Ser Thr Lys Lys Ser Lys Lys Ala
            515                 520                 525

Asp Cys Pro Ile Ala Trp Ala Asn Leu Met Leu Phe Asp Tyr Lys Asp
            530                 535                 540

Gln Leu Lys Thr Gly Glu Arg Cys Leu Tyr Met Trp Pro Ser Val Pro
545                 550                 555                 560

Asp Glu Lys Gly Glu Leu Leu Asn Pro Thr Gly Thr Val Arg Ser Asn
                565                 570                 575

Pro Asn Thr Asp Ser Ala Ala Leu Leu Ile Cys Leu Pro Glu Val
            580                 585                 590

Ala Pro His Pro Val Tyr Tyr Pro Ala Leu Glu Lys Ile Leu Glu Leu
            595                 600                 605

Gly Arg His Ser Glu Cys Val His Val Thr Glu Glu Glu Gln Leu Gln
610                 615                 620

Leu Arg Glu Ile Leu Glu Arg Arg Gly Ser Gly Glu Leu Tyr Glu His
625                 630                 635                 640

Glu Lys Asp Leu Val Trp Lys Leu Arg His Glu Val Gln Glu His Phe
                645                 650                 655

Pro Glu Ala Leu Ala Arg Leu Leu Leu Val Thr Lys Trp Asn Lys His
            660                 665                 670

Glu Asp Val Ala Gln Met Leu Tyr Leu Leu Cys Ser Trp Pro Glu Leu
            675                 680                 685

Pro Val Leu Ser Ala Leu Glu Leu Leu Asp Phe Ser Phe Pro Asp Cys
690                 695                 700

His Val Gly Ser Phe Ala Ile Lys Ser Leu Arg Lys Leu Thr Asp Asp
705                 710                 715                 720

Glu Leu Phe Gln Tyr Leu Leu Gln Leu Val Gln Val Leu Lys Tyr Glu
                725                 730                 735

Ser Tyr Leu Asp Cys Glu Leu Thr Lys Phe Leu Leu Asp Arg Ala Leu
            740                 745                 750

Ala Asn Arg Lys Ile Gly His Phe Leu Phe Trp His Leu Arg Ser Glu
            755                 760                 765

Met His Val Pro Ser Val Ala Leu Arg Phe Gly Leu Ile Leu Glu Ala
770                 775                 780

Tyr Cys Arg Gly Ser Thr His Met Lys Val Leu Met Lys Gln Gly
785                 790                 795                 800

Glu Ala Leu Ser Lys Leu Lys Ala Leu Asn Asp Phe Val Lys Leu Ser
                805                 810                 815

Ser Gln Lys Thr Pro Lys Pro Gln Thr Lys Glu Leu Met His Leu Cys
            820                 825                 830

Met Arg Gln Glu Ala Tyr Leu Glu Ala Leu Ser His Leu Gln Ser Pro
            835                 840                 845

Leu Asp Pro Ser Thr Leu Leu Ala Glu Val Cys Val Glu Gln Cys Thr
850                 855                 860

Phe Met Asp Ser Lys Met Lys Pro Leu Trp Ile Met Tyr Ser Asn Glu
865                 870                 875                 880
```

Glu Ala Gly Ser Gly Gly Ser Val Gly Ile Ile Phe Lys Asn Gly Asp
            885                 890                 895

Asp Leu Arg Gln Asp Met Leu Thr Leu Gln Met Ile Gln Leu Met Asp
            900                 905                 910

Val Leu Trp Lys Gln Glu Gly Leu Asp Leu Arg Met Thr Pro Tyr Gly
        915                 920                 925

Cys Leu Pro Thr Gly Asp Arg Thr Gly Leu Ile Glu Val Val Leu Arg
        930                 935                 940

Ser Asp Thr Ile Ala Asn Ile Gln Leu Asn Lys Ser Asn Met Ala Ala
945                 950                 955                 960

Thr Ala Ala Phe Asn Lys Asp Ala Leu Leu Asn Trp Leu Lys Ser Lys
            965                 970                 975

Asn Pro Gly Glu Ala Leu Asp Arg Ala Ile Glu Glu Phe Thr Leu Ser
            980                 985                 990

Cys Ala Gly Tyr Cys Val Ala Thr Tyr Val Leu Gly Ile Gly Asp Arg
            995                 1000                1005

His Ser Asp Asn Ile Met Ile Arg Glu Ser Gly Gln Leu Phe His
        1010                1015                1020

Ile Asp Phe Gly His Phe Leu Gly Asn Phe Lys Thr Lys Phe Gly
        1025                1030                1035

Ile Asn Arg Glu Arg Val Pro Phe Ile Leu Thr Tyr Asp Phe Val
        1040                1045                1050

His Val Ile Gln Gln Gly Lys Thr Asn Asn Ser Glu Lys Phe Glu
        1055                1060                1065

Arg Phe Arg Gly Tyr Cys Glu Arg Ala Tyr Thr Ile Leu Arg Arg
        1070                1075                1080

His Gly Leu Leu Phe Leu His Leu Phe Ala Leu Met Arg Ala Ala
        1085                1090                1095

Gly Leu Pro Glu Leu Ser Cys Ser Lys Asp Ile Gln Tyr Leu Lys
        1100                1105                1110

Asp Ser Leu Ala Leu Gly Lys Thr Glu Glu Ala Leu Lys His
        1115                1120                1125

Phe Arg Val Lys Phe Asn Glu Ala Leu Arg Glu Ser Trp Lys Thr
        1130                1135                1140

Lys Val Asn Trp Leu Ala His Asn Val Ser Lys Asp Asn Arg Gln
        1145                1150                1155

Glu Leu Gly Gly Ala His His His His His
        1160                1165

<210> SEQ ID NO 21
<211> LENGTH: 33
<212> TYPE: DNA
<213> ORGANISM: Artificial
<220> FEATURE:
<223> OTHER INFORMATION: PCR primer

<400> SEQUENCE: 21
ctctctgaaa tcactaagca ggagaaagat ttt                                    33

<210> SEQ ID NO 22
<211> LENGTH: 33
<212> TYPE: DNA
<213> ORGANISM: Artificial
<220> FEATURE:
<223> OTHER INFORMATION: PCR primer

<400> SEQUENCE: 22

```
aaaatctttc tcctgcttag tgatttcaga gag                                    33
```

<210> SEQ ID NO 23
<211> LENGTH: 1180
<212> TYPE: PRT
<213> ORGANISM: Artificial
<220> FEATURE:
<223> OTHER INFORMATION: PI3K kinase construct

<400> SEQUENCE: 23

```
Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Ile
            100                 105                 110

Ser Gly Gly Gly Gly Ile Met Val Leu Val Glu Cys Leu Leu Pro
        115                 120                 125

Asn Gly Met Ile Val Thr Leu Glu Cys Leu Arg Glu Ala Thr Leu Ile
    130                 135                 140

Thr Ile Lys His Glu Leu Phe Lys Glu Ala Arg Lys Tyr Pro Leu His
145                 150                 155                 160

Gln Leu Leu Gln Asp Glu Ser Ser Tyr Ile Phe Val Ser Val Thr Gln
                165                 170                 175

Glu Ala Glu Arg Glu Glu Phe Phe Asp Glu Thr Arg Arg Leu Cys Asp
            180                 185                 190

Leu Arg Leu Phe Gln Pro Phe Leu Lys Val Ile Glu Pro Val Gly Asn
        195                 200                 205

Arg Glu Glu Lys Ile Leu Asn Arg Glu Ile Gly Phe Ala Ile Gly Met
    210                 215                 220

Pro Val Cys Glu Phe Asp Met Val Lys Asp Pro Glu Val Gln Asp Phe
225                 230                 235                 240

Arg Arg Asn Ile Leu Asn Val Cys Lys Glu Ala Val Asp Leu Arg Asp
                245                 250                 255

Leu Asn Ser Pro His Ser Arg Ala Met Tyr Val Tyr Pro Pro Asn Val
            260                 265                 270

Glu Ser Ser Pro Glu Leu Pro Lys His Ile Tyr Asn Lys Leu Asp Lys
        275                 280                 285

Gly Gln Ile Ile Val Val Ile Trp Val Ile Val Ser Pro Asn Asn Asp
    290                 295                 300

Lys Gln Lys Tyr Thr Leu Lys Ile Asn His Asp Cys Val Pro Glu Gln
305                 310                 315                 320

Val Ile Ala Glu Ala Ile Arg Lys Lys Thr Arg Ser Met Leu Leu Ser
                325                 330                 335

Ser Glu Gln Leu Lys Leu Cys Val Leu Glu Tyr Gln Gly Lys Tyr Ile
            340                 345                 350

Leu Lys Val Cys Gly Cys Asp Glu Tyr Phe Leu Glu Lys Tyr Pro Leu
        355                 360                 365
```

```
Ser Gln Tyr Lys Tyr Ile Arg Ser Cys Ile Met Leu Gly Arg Met Pro
    370                 375                 380

Asn Leu Met Leu Met Ala Lys Glu Ser Leu Tyr Ser Gln Leu Pro Met
385                 390                 395                 400

Asp Cys Phe Thr Met Pro Ser Tyr Ser Arg Arg Ile Ser Thr Ala Thr
                405                 410                 415

Pro Tyr Met Asn Gly Glu Thr Ser Thr Lys Ser Leu Trp Val Ile Asn
            420                 425                 430

Ser Ala Leu Arg Ile Lys Ile Leu Cys Ala Thr Tyr Val Asn Val Asn
        435                 440                 445

Ile Arg Asp Ile Asp Lys Ile Tyr Val Arg Thr Gly Ile Tyr His Gly
    450                 455                 460

Gly Glu Pro Leu Cys Asp Asn Val Asn Thr Gln Arg Val Pro Cys Ser
465                 470                 475                 480

Asn Pro Arg Trp Asn Glu Trp Leu Asn Tyr Asp Ile Tyr Ile Pro Asp
                485                 490                 495

Leu Pro Arg Ala Ala Arg Leu Cys Leu Ser Ile Cys Ser Val Lys Gly
            500                 505                 510

Arg Lys Gly Ala Lys Glu Glu His Cys Pro Leu Ala Trp Gly Asn Ile
        515                 520                 525

Asn Leu Phe Asp Tyr Thr Asp Thr Leu Val Ser Gly Lys Met Ala Leu
    530                 535                 540

Asn Leu Trp Pro Val Pro His Gly Leu Glu Asp Leu Leu Asn Pro Ile
545                 550                 555                 560

Gly Val Thr Gly Ser Asn Pro Asn Lys Glu Thr Pro Cys Leu Glu Leu
                565                 570                 575

Glu Phe Asp Trp Phe Ser Ser Val Val Lys Phe Pro Asp Met Ser Val
            580                 585                 590

Ile Glu Glu His Ala Asn Trp Ser Val Ser Arg Glu Ala Gly Phe Ser
        595                 600                 605

Tyr Ser His Ala Gly Leu Ser Asn Arg Leu Ala Arg Asp Asn Glu Leu
    610                 615                 620

Arg Glu Asn Asp Lys Glu Gln Leu Lys Ala Ile Ser Thr Arg Asp Pro
625                 630                 635                 640

Leu Ser Glu Ile Thr Lys Gln Glu Lys Asp Phe Leu Trp Ser His Arg
                645                 650                 655

His Tyr Cys Val Thr Ile Pro Glu Ile Leu Pro Lys Leu Leu Leu Ser
            660                 665                 670

Val Lys Trp Asn Ser Arg Asp Glu Val Ala Gln Met Tyr Cys Leu Val
        675                 680                 685

Lys Asp Trp Pro Pro Ile Lys Pro Glu Gln Ala Met Glu Leu Leu Asp
    690                 695                 700

Cys Asn Tyr Pro Asp Pro Met Val Arg Gly Phe Ala Val Arg Cys Leu
705                 710                 715                 720

Glu Lys Tyr Leu Thr Asp Asp Lys Leu Ser Gln Tyr Leu Ile Gln Leu
                725                 730                 735

Val Gln Val Leu Lys Tyr Glu Gln Tyr Leu Asp Asn Leu Leu Val Arg
            740                 745                 750

Phe Leu Leu Lys Lys Ala Leu Thr Asn Gln Arg Ile Gly His Phe Phe
        755                 760                 765

Phe Trp His Leu Lys Ser Glu Met His Asn Lys Thr Val Ser Gln Arg
    770                 775                 780

Phe Gly Leu Leu Leu Glu Ser Tyr Cys Arg Ala Cys Gly Met Tyr Leu
```

```
                785                 790                 795                 800
Lys His Leu Asn Arg Gln Val Glu Ala Met Glu Lys Leu Ile Asn Leu
                    805                 810                 815

Thr Asp Ile Leu Lys Gln Glu Lys Asp Glu Thr Gln Lys Val Gln
        820                 825                 830

Met Lys Phe Leu Val Glu Gln Met Arg Arg Pro Asp Phe Met Asp Ala
        835                 840                 845

Leu Gln Gly Phe Leu Ser Pro Leu Asn Pro Ala His Gln Leu Gly Asn
        850                 855                 860

Leu Arg Leu Glu Glu Cys Arg Ile Met Ser Ser Ala Lys Arg Pro Leu
865                 870                 875                 880

Trp Leu Asn Trp Glu Asn Pro Asp Ile Met Ser Glu Leu Leu Phe Gln
                    885                 890                 895

Asn Asn Glu Ile Ile Phe Lys Asn Gly Asp Asp Leu Arg Gln Asp Met
                    900                 905                 910

Leu Thr Leu Gln Ile Ile Arg Ile Met Glu Asn Ile Trp Gln Asn Gln
        915                 920                 925

Gly Leu Asp Leu Arg Met Leu Pro Tyr Gly Cys Leu Ser Ile Gly Asp
        930                 935                 940

Cys Val Gly Leu Ile Glu Val Val Arg Asn Ser His Thr Ile Met Gln
945                 950                 955                 960

Ile Gln Cys Lys Gly Gly Leu Lys Gly Ala Leu Gln Phe Asn Ser His
                    965                 970                 975

Thr Leu His Gln Trp Leu Lys Asp Lys Asn Lys Gly Glu Ile Tyr Asp
                    980                 985                 990

Ala Ala Ile Asp Leu Phe Thr Arg Ser Cys Ala Gly Tyr Cys Val Ala
        995                 1000                1005

Thr Phe Ile Leu Gly Ile Gly Asp Arg His Asn Ser Asn Ile Met
1010                1015                1020

Val Lys Asp Asp Gly Gln Leu Phe His Ile Asp Phe Gly His Phe
1025                1030                1035

Leu Asp His Lys Lys Lys Phe Gly Tyr Lys Arg Glu Arg Val
1040                1045                1050

Pro Phe Val Leu Thr Gln Asp Phe Leu Ile Val Ile Ser Lys Gly
1055                1060                1065

Ala Gln Glu Cys Thr Lys Thr Arg Glu Phe Glu Arg Phe Gln Glu
1070                1075                1080

Met Cys Tyr Lys Ala Tyr Leu Ala Ile Arg Gln His Ala Asn Leu
1085                1090                1095

Phe Ile Asn Leu Phe Ser Met Met Leu Gly Ser Gly Met Pro Glu
1100                1105                1110

Leu Gln Ser Phe Asp Asp Ile Ala Tyr Ile Arg Lys Thr Leu Ala
1115                1120                1125

Leu Asp Lys Thr Glu Gln Glu Ala Leu Glu Tyr Phe Met Lys Gln
1130                1135                1140

Met Asn Asp Ala His His Gly Gly Trp Thr Thr Lys Met Asp Trp
1145                1150                1155

Ile Phe His Thr Ile Lys Gln His Ala Leu Asn Glu Leu Gly Gly
1160                1165                1170

Ala His His His His His His
1175                1180

<210> SEQ ID NO 24
<211> LENGTH: 33
```

<212> TYPE: DNA
<213> ORGANISM: Artificial
<220> FEATURE:
<223> OTHER INFORMATION: PCR primer

<400> SEQUENCE: 24
caaatgaatg atgcacgtca tggtggctgg aca        33

<210> SEQ ID NO 25
<211> LENGTH: 33
<212> TYPE: DNA
<213> ORGANISM: Artificial
<220> FEATURE:
<223> OTHER INFORMATION: PCR primer

<400> SEQUENCE: 25
tgtccagcca ccatgacgtg catcattcat ttg        33

<210> SEQ ID NO 26
<211> LENGTH: 1180
<212> TYPE: PRT
<213> ORGANISM: Artificial
<220> FEATURE:
<223> OTHER INFORMATION: PI3K kinase construct

<400> SEQUENCE: 26

```
Met Arg Glu Tyr Asp Arg Leu Tyr Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Ile
            100                 105                 110

Ser Gly Gly Gly Gly Gly Ile Met Val Leu Val Glu Cys Leu Leu Pro
        115                 120                 125

Asn Gly Met Ile Val Thr Leu Glu Cys Leu Arg Glu Ala Thr Leu Ile
    130                 135                 140

Thr Ile Lys His Glu Leu Phe Lys Glu Ala Arg Lys Tyr Pro Leu His
145                 150                 155                 160

Gln Leu Leu Gln Asp Glu Ser Ser Tyr Ile Phe Val Ser Val Thr Gln
                165                 170                 175

Glu Ala Glu Arg Glu Glu Phe Phe Asp Glu Thr Arg Arg Leu Cys Asp
            180                 185                 190

Leu Arg Leu Phe Gln Pro Phe Leu Lys Val Ile Glu Pro Val Gly Asn
        195                 200                 205

Arg Glu Glu Lys Ile Leu Asn Arg Glu Ile Gly Phe Ala Ile Gly Met
    210                 215                 220

Pro Val Cys Glu Phe Asp Met Val Lys Asp Pro Glu Val Gln Asp Phe
225                 230                 235                 240

Arg Arg Asn Ile Leu Asn Val Cys Lys Glu Ala Val Asp Leu Arg Asp
                245                 250                 255

Leu Asn Ser Pro His Ser Arg Ala Met Tyr Val Tyr Pro Pro Asn Val
```

```
              260             265             270
Glu Ser Ser Pro Glu Leu Pro Lys His Ile Tyr Asn Lys Leu Asp Lys
            275             280             285
Gly Gln Ile Ile Val Val Ile Trp Val Ile Val Ser Pro Asn Asn Asp
            290             295             300
Lys Gln Lys Tyr Thr Leu Lys Ile Asn His Asp Cys Val Pro Glu Gln
305             310             315             320
Val Ile Ala Glu Ala Ile Arg Lys Lys Thr Arg Ser Met Leu Leu Ser
            325             330             335
Ser Glu Gln Leu Lys Leu Cys Val Leu Glu Tyr Gln Gly Lys Tyr Ile
            340             345             350
Leu Lys Val Cys Gly Cys Asp Glu Tyr Phe Leu Glu Lys Tyr Pro Leu
            355             360             365
Ser Gln Tyr Lys Tyr Ile Arg Ser Cys Ile Met Leu Gly Arg Met Pro
            370             375             380
Asn Leu Met Leu Met Ala Lys Glu Ser Leu Tyr Ser Gln Leu Pro Met
385             390             395             400
Asp Cys Phe Thr Met Pro Ser Tyr Ser Arg Arg Ile Ser Thr Ala Thr
                405             410             415
Pro Tyr Met Asn Gly Glu Thr Ser Thr Lys Ser Leu Trp Val Ile Asn
                420             425             430
Ser Ala Leu Arg Ile Lys Ile Leu Cys Ala Thr Tyr Val Asn Val Asn
            435             440             445
Ile Arg Asp Ile Asp Lys Ile Tyr Val Arg Thr Gly Ile Tyr His Gly
            450             455             460
Gly Glu Pro Leu Cys Asp Asn Val Asn Thr Gln Arg Val Pro Cys Ser
465             470             475             480
Asn Pro Arg Trp Asn Glu Trp Leu Asn Tyr Asp Ile Tyr Ile Pro Asp
                485             490             495
Leu Pro Arg Ala Ala Arg Leu Cys Leu Ser Ile Cys Ser Val Lys Gly
                500             505             510
Arg Lys Gly Ala Lys Glu Glu His Cys Pro Leu Ala Trp Gly Asn Ile
            515             520             525
Asn Leu Phe Asp Tyr Thr Asp Thr Leu Val Ser Gly Lys Met Ala Leu
            530             535             540
Asn Leu Trp Pro Val Pro His Gly Leu Glu Asp Leu Leu Asn Pro Ile
545             550             555             560
Gly Val Thr Gly Ser Asn Pro Asn Lys Glu Thr Pro Cys Leu Glu Leu
                565             570             575
Glu Phe Asp Trp Phe Ser Ser Val Val Lys Phe Pro Asp Met Ser Val
                580             585             590
Ile Glu Glu His Ala Asn Trp Ser Val Ser Arg Glu Ala Gly Phe Ser
            595             600             605
Tyr Ser His Ala Gly Leu Ser Asn Arg Leu Ala Arg Asp Asn Glu Leu
            610             615             620
Arg Glu Asn Asp Lys Glu Gln Leu Lys Ala Ile Ser Thr Arg Asp Pro
625             630             635             640
Leu Ser Glu Ile Thr Glu Gln Glu Lys Asp Phe Leu Trp Ser His Arg
                645             650             655
His Tyr Cys Val Thr Ile Pro Glu Ile Leu Pro Lys Leu Leu Leu Ser
                660             665             670
Val Lys Trp Asn Ser Arg Asp Glu Val Ala Gln Met Tyr Cys Leu Val
            675             680             685
```

```
Lys Asp Trp Pro Pro Ile Lys Pro Glu Gln Ala Met Glu Leu Leu Asp
    690             695             700

Cys Asn Tyr Pro Asp Pro Met Val Arg Gly Phe Ala Val Arg Cys Leu
705             710             715             720

Glu Lys Tyr Leu Thr Asp Asp Lys Leu Ser Gln Tyr Leu Ile Gln Leu
            725             730             735

Val Gln Val Leu Lys Tyr Glu Gln Tyr Leu Asp Asn Leu Leu Val Arg
        740             745             750

Phe Leu Leu Lys Lys Ala Leu Thr Asn Gln Arg Ile Gly His Phe Phe
    755             760             765

Phe Trp His Leu Lys Ser Glu Met His Asn Lys Thr Val Ser Gln Arg
770             775             780

Phe Gly Leu Leu Leu Glu Ser Tyr Cys Arg Ala Cys Gly Met Tyr Leu
785             790             795             800

Lys His Leu Asn Arg Gln Val Glu Ala Met Glu Lys Leu Ile Asn Leu
            805             810             815

Thr Asp Ile Leu Lys Gln Glu Lys Lys Asp Glu Thr Gln Lys Val Gln
            820             825             830

Met Lys Phe Leu Val Gln Met Arg Arg Pro Asp Phe Met Asp Ala
    835             840             845

Leu Gln Gly Phe Leu Ser Pro Leu Asn Pro Ala His Gln Leu Gly Asn
    850             855             860

Leu Arg Leu Glu Glu Cys Arg Ile Met Ser Ser Ala Lys Arg Pro Leu
865             870             875             880

Trp Leu Asn Trp Glu Asn Pro Asp Ile Met Ser Glu Leu Leu Phe Gln
                885             890             895

Asn Asn Glu Ile Ile Phe Lys Asn Gly Asp Asp Leu Arg Gln Asp Met
            900             905             910

Leu Thr Leu Gln Ile Ile Arg Ile Met Glu Asn Ile Trp Gln Asn Gln
            915             920             925

Gly Leu Asp Leu Arg Met Leu Pro Tyr Gly Cys Leu Ser Ile Gly Asp
    930             935             940

Cys Val Gly Leu Ile Glu Val Val Arg Asn Ser His Thr Ile Met Gln
945             950             955             960

Ile Gln Cys Lys Gly Gly Leu Lys Gly Ala Leu Gln Phe Asn Ser His
            965             970             975

Thr Leu His Gln Trp Leu Lys Asp Lys Asn Lys Gly Glu Ile Tyr Asp
    980             985             990

Ala Ala Ile Asp Leu Phe Thr Arg Ser Cys Ala Gly Tyr Cys Val Ala
        995             1000            1005

Thr Phe Ile Leu Gly Ile Gly Asp Arg His Asn Ser Asn Ile Met
    1010            1015            1020

Val Lys Asp Asp Gly Gln Leu Phe His Ile Asp Phe Gly His Phe
    1025            1030            1035

Leu Asp His Lys Lys Lys Lys Phe Gly Tyr Lys Arg Glu Arg Val
    1040            1045            1050

Pro Phe Val Leu Thr Gln Asp Phe Leu Ile Val Ile Ser Lys Gly
    1055            1060            1065

Ala Gln Glu Cys Thr Lys Thr Arg Glu Phe Glu Arg Phe Gln Glu
    1070            1075            1080

Met Cys Tyr Lys Ala Tyr Leu Ala Ile Arg Gln His Ala Asn Leu
    1085            1090            1095

Phe Ile Asn Leu Phe Ser Met Met Leu Gly Ser Gly Met Pro Glu
    1100            1105            1110
```

```
Leu Gln Ser Phe Asp Asp Ile Ala Tyr Ile Arg Lys Thr Leu Ala
    1115                1120                1125

Leu Asp Lys Thr Glu Gln Glu Ala Leu Glu Tyr Phe Met Lys Gln
    1130                1135                1140

Met Asn Asp Ala Arg His Gly Gly Trp Thr Thr Lys Met Asp Trp
    1145                1150                1155

Ile Phe His Thr Ile Lys Gln His Ala Leu Asn Glu Leu Gly Gly
    1160                1165                1170

Ala His His His His His His
    1175            1180
```